US011041151B2

(12) United States Patent
Smith et al.

(10) Patent No.: US 11,041,151 B2
(45) Date of Patent: Jun. 22, 2021

(54) RNA ARRAY COMPOSITIONS AND METHODS

(71) Applicant: Wisconsin Alumni Research Foundation, Madison, WI (US)

(72) Inventors: Lloyd Smith, Madison, WI (US); Cheng-Hsien Wu, Burlingame, CA (US)

(73) Assignee: Wisconsin Alumni Research Foundation, Madison, WI (US)

( * ) Notice: Subject to any disclaimer, the term of this patent is extended or adjusted under 35 U.S.C. 154(b) by 636 days.

(21) Appl. No.: 15/834,138

(22) Filed: Dec. 7, 2017

(65) Prior Publication Data

US 2018/0112211 A1 Apr. 26, 2018

Related U.S. Application Data

(62) Division of application No. 14/073,350, filed on Nov. 6, 2013, now abandoned.

(60) Provisional application No. 61/723,011, filed on Nov. 6, 2012.

(51) Int. Cl.

| | |
|---|---|
| ***C12N 15/10*** | (2006.01) |
| ***C12Q 1/6837*** | (2018.01) |
| ***B01J 19/00*** | (2006.01) |
| *C40B 50/18* | (2006.01) |

(52) U.S. Cl.

CPC ...... *C12N 15/1068* (2013.01); *B01J 19/0046* (2013.01); *C12Q 1/6837* (2013.01); *B01J 2219/005* (2013.01); *B01J 2219/00529* (2013.01); *B01J 2219/00585* (2013.01); *B01J 2219/00596* (2013.01); *B01J 2219/00605* (2013.01); *B01J 2219/00711* (2013.01); *B01J 2219/00722* (2013.01); *C40B 50/18* (2013.01)

(58) Field of Classification Search

CPC ............. B01J 19/0046; B01J 2219/005; B01J 2219/00529; B01J 2219/00585; B01J 2219/00596; B01J 2219/00711; B01J 2219/00722; C12N 15/1068; C12Q 1/6837; C40B 50/18

See application file for complete search history.

*Primary Examiner* — Jeremy C Flinders

(74) *Attorney, Agent, or Firm* — Boyle Fredrickson S.C.

(57) ABSTRACT

Described herein are RNA arrays, and compositions and methods for generating RNA arrays, particularly high density RNA arrays. The disclosed methods for generating RNA arrays utilize template DNA arrays and RNA polymerase to generate RNA arrays. In some embodiments, the disclosed methods use an RNA polymerase and modified ribonucleosides to generate modified RNA arrays for various applications, e.g. RNA arrays having higher nuclease resistance, more conformationally stable RNA arrays, and higher binding affinity RNA aptamer arrays. In some embodiments, the disclosed methods are used to generate RNA bead arrays.

5 Claims, 6 Drawing Sheets
(6 of 6 Drawing Sheet(s) Filed in Color)

Specification includes a Sequence Listing.

A

B

2A

2B

SEQUENCE LISTING

```
<160> NUMBER OF SEQ ID NOS: 342

<210> SEQ ID NO 1
<211> LENGTH: 12
<212> TYPE: DNA
<213> ORGANISM: ARTIFICIAL SEQUENCE
<220> FEATURE:
<223> OTHER INFORMATION: SYNTHETIC

<400> SEQUENCE: 1

ttcgccgtgt cc                                                          12


<210> SEQ ID NO 2
<211> LENGTH: 12
<212> TYPE: RNA
<213> ORGANISM: ARTIFICIAL SEQUENCE
<220> FEATURE:
<223> OTHER INFORMATION: SYNTHETIC

<400> SEQUENCE: 2

ggacacggcg aa                                                          12


<210> SEQ ID NO 3
<211> LENGTH: 180
<212> TYPE: DNA
<213> ORGANISM: MOUSE

<400> SEQUENCE: 3

ttagctcctg tcccagtcca tcaccacggg acaaacatag tagaaaacct gatcccttta      60

ccccttcca cccacggttt gtgtagagct cacaagcaaa acaaacttat tttgaacact      120

ggggtcctag cacgctgccc tgacaatcat taacctgtgc cgcacagcca gcccttcata      180


<210> SEQ ID NO 4
<211> LENGTH: 21
<212> TYPE: DNA
<213> ORGANISM: ARTIFICIAL SEQUENCE
<220> FEATURE:
<223> OTHER INFORMATION: SYNTHETIC

<400> SEQUENCE: 4

ttagctcctg tcccagtcca t                                                21
```

<210> SEQ ID NO 5
<211> LENGTH: 19
<212> TYPE: DNA
<213> ORGANISM: ARTIFICIAL SEQUENCE
<220> FEATURE:
<223> OTHER INFORMATION: SYNTHETIC

<400> SEQUENCE: 5
tatgaagggc tggctgtgc 19

<210> SEQ ID NO 6
<211> LENGTH: 21
<212> TYPE: DNA
<213> ORGANISM: ARTIFICIAL SEQUENCE
<220> FEATURE:
<223> OTHER INFORMATION: SYNTHETIC

<400> SEQUENCE: 6
ttagctcctg tcccagtcca t 21

<210> SEQ ID NO 7
<211> LENGTH: 32
<212> TYPE: DNA
<213> ORGANISM: ARTIFICIAL SEQUENCE
<220> FEATURE:
<223> OTHER INFORMATION: SYNTHETIC

<400> SEQUENCE: 7
ttagctcctg tcccagtcca ttcgccgtgt cc 32

<210> SEQ ID NO 8
<211> LENGTH: 19
<212> TYPE: DNA
<213> ORGANISM: ARTIFICIAL SEQUENCE
<220> FEATURE:
<223> OTHER INFORMATION: SYNTHETIC

<400> SEQUENCE: 8
actcttgcag gtcatcggc 19

<210> SEQ ID NO 9
<211> LENGTH: 18
<212> TYPE: DNA
<213> ORGANISM: ARTIFICIAL SEQUENCE
<220> FEATURE:
<223> OTHER INFORMATION: SYNTHETIC

<400> SEQUENCE: 9
ccactgttgc aaagttat 18

<210> SEQ ID NO 10
<211> LENGTH: 19
<212> TYPE: DNA
<213> ORGANISM: ARTIFICIAL SEQUENCE
<220> FEATURE:
<223> OTHER INFORMATION: SYNTHETIC

<400> SEQUENCE: 10
gccgatgacc tgcaagagt 19

<210> SEQ ID NO 11
<211> LENGTH: 18
<212> TYPE: DNA
<213> ORGANISM: ARTIFICIAL SEQUENCE
<220> FEATURE:
<223> OTHER INFORMATION: SYNTHETIC

<400> SEQUENCE: 11
ataactttgc aacagtgg 18

<210> SEQ ID NO 12
<211> LENGTH: 20
<212> TYPE: DNA
<213> ORGANISM: ARTIFICIAL SEQUENCE
<220> FEATURE:
<223> OTHER INFORMATION: SYNTHETIC

<400> SEQUENCE: 12
cgcacagcca gcccttcata 20

<210> SEQ ID NO 13
<211> LENGTH: 20
<212> TYPE: DNA
<213> ORGANISM: ARTIFICIAL SEQUENCE
<220> FEATURE:
<223> OTHER INFORMATION: SYNTHETIC

<400> SEQUENCE: 13
ccgcacagcc agcccttcat 20

<210> SEQ ID NO 14
<211> LENGTH: 20
<212> TYPE: DNA
<213> ORGANISM: ARTIFICIAL SEQUENCE
<220> FEATURE:
<223> OTHER INFORMATION: SYNTHETIC

<400> SEQUENCE: 14
gccgcacagc cagcccttca 20

<210> SEQ ID NO 15
<211> LENGTH: 20
<212> TYPE: DNA
<213> ORGANISM: ARTIFICIAL SEQUENCE
<220> FEATURE:
<223> OTHER INFORMATION: SYNTHETIC

<400> SEQUENCE: 15
tgccgcacag ccagcccttc 20

<210> SEQ ID NO 16
<211> LENGTH: 20
<212> TYPE: DNA
<213> ORGANISM: ARTIFICIAL SEQUENCE
<220> FEATURE:
<223> OTHER INFORMATION: SYNTHETIC

<400> SEQUENCE: 16
gtgccgcaca gccagccctt 20

<210> SEQ ID NO 17
<211> LENGTH: 20
<212> TYPE: DNA
<213> ORGANISM: ARTIFICIAL SEQUENCE
<220> FEATURE:
<223> OTHER INFORMATION: SYNTHETIC

<400> SEQUENCE: 17
tgtgccgcac agccagccct 20

<210> SEQ ID NO 18
<211> LENGTH: 20

<212> TYPE: DNA
<213> ORGANISM: ARTIFICIAL SEQUENCE
<220> FEATURE:
<223> OTHER INFORMATION: SYNTHETIC

<400> SEQUENCE: 18
ctgtgccgca cagccagccc 20

<210> SEQ ID NO 19
<211> LENGTH: 20
<212> TYPE: DNA
<213> ORGANISM: ARTIFICIAL SEQUENCE
<220> FEATURE:
<223> OTHER INFORMATION: SYNTHETIC

<400> SEQUENCE: 19
cctgtgccgc acagccagcc 20

<210> SEQ ID NO 20
<211> LENGTH: 20
<212> TYPE: DNA
<213> ORGANISM: ARTIFICIAL SEQUENCE
<220> FEATURE:
<223> OTHER INFORMATION: SYNTHETIC

<400> SEQUENCE: 20
acctgtgccg cacagccagc 20

<210> SEQ ID NO 21
<211> LENGTH: 20
<212> TYPE: DNA
<213> ORGANISM: ARTIFICIAL SEQUENCE
<220> FEATURE:
<223> OTHER INFORMATION: SYNTHETIC

<400> SEQUENCE: 21
aacctgtgcc gcacagccag 20

<210> SEQ ID NO 22
<211> LENGTH: 20
<212> TYPE: DNA
<213> ORGANISM: ARTIFICIAL SEQUENCE
<220> FEATURE:
<223> OTHER INFORMATION: SYNTHETIC

<400> SEQUENCE: 22
taacctgtgc cgcacagcca 20

<210> SEQ ID NO 23
<211> LENGTH: 20
<212> TYPE: DNA
<213> ORGANISM: ARTIFICIAL SEQUENCE
<220> FEATURE:
<223> OTHER INFORMATION: SYNTHETIC

<400> SEQUENCE: 23
ttaacctgtg ccgcacagcc 20

<210> SEQ ID NO 24
<211> LENGTH: 20
<212> TYPE: DNA
<213> ORGANISM: ARTIFICIAL SEQUENCE
<220> FEATURE:
<223> OTHER INFORMATION: SYNTHETIC

<400> SEQUENCE: 24
attaacctgt gccgcacagc 20

<210> SEQ ID NO 25
<211> LENGTH: 20
<212> TYPE: DNA
<213> ORGANISM: ARTIFICIAL SEQUENCE
<220> FEATURE:
<223> OTHER INFORMATION: SYNTHETIC

<400> SEQUENCE: 25
cattaacctg tgccgcacag 20

<210> SEQ ID NO 26
<211> LENGTH: 20
<212> TYPE: DNA
<213> ORGANISM: ARTIFICIAL SEQUENCE
<220> FEATURE:
<223> OTHER INFORMATION: SYNTHETIC

<400> SEQUENCE: 26
tcattaacct gtgccgcaca 20

<210> SEQ ID NO 27
<211> LENGTH: 20
<212> TYPE: DNA
<213> ORGANISM: ARTIFICIAL SEQUENCE
<220> FEATURE:
<223> OTHER INFORMATION: SYNTHETIC

<400> SEQUENCE: 27
atcattaacc tgtgccgcac 20

<210> SEQ ID NO 28
<211> LENGTH: 20
<212> TYPE: DNA
<213> ORGANISM: ARTIFICIAL SEQUENCE
<220> FEATURE:
<223> OTHER INFORMATION: SYNTHETIC

<400> SEQUENCE: 28
aatcattaac ctgtgccgca 20

<210> SEQ ID NO 29
<211> LENGTH: 20
<212> TYPE: DNA
<213> ORGANISM: ARTIFICIAL SEQUENCE
<220> FEATURE:
<223> OTHER INFORMATION: SYNTHETIC

<400> SEQUENCE: 29
caatcattaa cctgtgccgc 20

<210> SEQ ID NO 30
<211> LENGTH: 20
<212> TYPE: DNA
<213> ORGANISM: ARTIFICIAL SEQUENCE
<220> FEATURE:
<223> OTHER INFORMATION: SYNTHETIC

<400> SEQUENCE: 30
acaatcatta acctgtgccg 20

<210> SEQ ID NO 31
<211> LENGTH: 20
<212> TYPE: DNA
<213> ORGANISM: ARTIFICIAL SEQUENCE

<220> FEATURE:
<223> OTHER INFORMATION: SYNTHETIC

<400> SEQUENCE: 31
gacaatcatt aacctgtgcc 20

<210> SEQ ID NO 32
<211> LENGTH: 20
<212> TYPE: DNA
<213> ORGANISM: ARTIFICIAL SEQUENCE
<220> FEATURE:
<223> OTHER INFORMATION: SYNTHETIC

<400> SEQUENCE: 32
tgacaatcat taacctgtgc 20

<210> SEQ ID NO 33
<211> LENGTH: 20
<212> TYPE: DNA
<213> ORGANISM: ARTIFICIAL SEQUENCE
<220> FEATURE:
<223> OTHER INFORMATION: SYNTHETIC

<400> SEQUENCE: 33
ctgacaatca ttaacctgtg 20

<210> SEQ ID NO 34
<211> LENGTH: 20
<212> TYPE: DNA
<213> ORGANISM: ARTIFICIAL SEQUENCE
<220> FEATURE:
<223> OTHER INFORMATION: SYNTHETIC

<400> SEQUENCE: 34
cctgacaatc attaacctgt 20

<210> SEQ ID NO 35
<211> LENGTH: 20
<212> TYPE: DNA
<213> ORGANISM: ARTIFICIAL SEQUENCE
<220> FEATURE:
<223> OTHER INFORMATION: SYNTHETIC

<400> SEQUENCE: 35
ccctgacaat cattaacctg 20

<210> SEQ ID NO 36
<211> LENGTH: 20
<212> TYPE: DNA
<213> ORGANISM: ARTIFICIAL SEQUENCE
<220> FEATURE:
<223> OTHER INFORMATION: SYNTHETIC

<400> SEQUENCE: 36
gccctgacaa tcattaacct 20

<210> SEQ ID NO 37
<211> LENGTH: 20
<212> TYPE: DNA
<213> ORGANISM: ARTIFICIAL SEQUENCE
<220> FEATURE:
<223> OTHER INFORMATION: SYNTHETIC

<400> SEQUENCE: 37
tgccctgaca atcattaacc 20

<210> SEQ ID NO 38
<211> LENGTH: 20
<212> TYPE: DNA
<213> ORGANISM: ARTIFICIAL SEQUENCE
<220> FEATURE:
<223> OTHER INFORMATION: SYNTHETIC

<400> SEQUENCE: 38
ctgccctgac aatcattaac 20

<210> SEQ ID NO 39
<211> LENGTH: 20
<212> TYPE: DNA
<213> ORGANISM: ARTIFICIAL SEQUENCE
<220> FEATURE:
<223> OTHER INFORMATION: SYNTHETIC

<400> SEQUENCE: 39
gctgccctga caatcattaa 20

<210> SEQ ID NO 40
<211> LENGTH: 20
<212> TYPE: DNA
<213> ORGANISM: ARTIFICIAL SEQUENCE
<220> FEATURE:
<223> OTHER INFORMATION: SYNTHETIC

<400> SEQUENCE: 40
cgctgccctg acaatcatta 20

<210> SEQ ID NO 41
<211> LENGTH: 20
<212> TYPE: DNA
<213> ORGANISM: ARTIFICIAL SEQUENCE
<220> FEATURE:
<223> OTHER INFORMATION: SYNTHETIC

<400> SEQUENCE: 41
acgctgccct gacaatcatt 20

<210> SEQ ID NO 42
<211> LENGTH: 20
<212> TYPE: DNA
<213> ORGANISM: ARTIFICIAL SEQUENCE
<220> FEATURE:
<223> OTHER INFORMATION: SYNTHETIC

<400> SEQUENCE: 42
cacgctgccc tgacaatcat 20

<210> SEQ ID NO 43
<211> LENGTH: 20
<212> TYPE: DNA
<213> ORGANISM: ARTIFICIAL SEQUENCE
<220> FEATURE:
<223> OTHER INFORMATION: SYNTHETIC

<400> SEQUENCE: 43
gcacgctgcc ctgacaatca 20

<210> SEQ ID NO 44
<211> LENGTH: 20
<212> TYPE: DNA
<213> ORGANISM: ARTIFICIAL SEQUENCE
<220> FEATURE:
<223> OTHER INFORMATION: SYNTHETIC

<400> SEQUENCE: 44
agcacgctgc cctgacaatc 20

<210> SEQ ID NO 45
<211> LENGTH: 20
<212> TYPE: DNA
<213> ORGANISM: ARTIFICIAL SEQUENCE
<220> FEATURE:
<223> OTHER INFORMATION: SYNTHETIC

<400> SEQUENCE: 45
tagcacgctg ccctgacaat 20

<210> SEQ ID NO 46
<211> LENGTH: 20
<212> TYPE: DNA
<213> ORGANISM: ARTIFICIAL SEQUENCE
<220> FEATURE:
<223> OTHER INFORMATION: SYNTHETIC

<400> SEQUENCE: 46
ctagcacgct gccctgacaa 20

<210> SEQ ID NO 47
<211> LENGTH: 20
<212> TYPE: DNA
<213> ORGANISM: ARTIFICIAL SEQUENCE
<220> FEATURE:
<223> OTHER INFORMATION: SYNTHETIC

<400> SEQUENCE: 47
cctagcacgc tgccctgaca 20

<210> SEQ ID NO 48
<211> LENGTH: 20
<212> TYPE: DNA
<213> ORGANISM: ARTIFICIAL SEQUENCE
<220> FEATURE:
<223> OTHER INFORMATION: SYNTHETIC

<400> SEQUENCE: 48
tcctagcacg ctgccctgac 20

<210> SEQ ID NO 49
<211> LENGTH: 20
<212> TYPE: DNA
<213> ORGANISM: ARTIFICIAL SEQUENCE
<220> FEATURE:
<223> OTHER INFORMATION: SYNTHETIC

<400> SEQUENCE: 49
gtcctagcac gctgccctga 20

<210> SEQ ID NO 50
<211> LENGTH: 20
<212> TYPE: DNA
<213> ORGANISM: ARTIFICIAL SEQUENCE
<220> FEATURE:
<223> OTHER INFORMATION: SYNTHETIC

<400> SEQUENCE: 50
ggtcctagca cgctgccctg 20

<210> SEQ ID NO 51

<211> LENGTH: 20
<212> TYPE: DNA
<213> ORGANISM: ARTIFICIAL SEQUENCE
<220> FEATURE:
<223> OTHER INFORMATION: SYNTHETIC

<400> SEQUENCE: 51
gggtcctagc acgctgccct 20

<210> SEQ ID NO 52
<211> LENGTH: 20
<212> TYPE: DNA
<213> ORGANISM: ARTIFICIAL SEQUENCE
<220> FEATURE:
<223> OTHER INFORMATION: SYNTHETIC

<400> SEQUENCE: 52
ggggtcctag cacgctgccc 20

<210> SEQ ID NO 53
<211> LENGTH: 20
<212> TYPE: DNA
<213> ORGANISM: ARTIFICIAL SEQUENCE
<220> FEATURE:
<223> OTHER INFORMATION: SYNTHETIC

<400> SEQUENCE: 53
tggggtccta gcacgctgcc 20

<210> SEQ ID NO 54
<211> LENGTH: 20
<212> TYPE: DNA
<213> ORGANISM: ARTIFICIAL SEQUENCE
<220> FEATURE:
<223> OTHER INFORMATION: SYNTHETIC

<400> SEQUENCE: 54
ctggggtcct agcacgctgc 20

<210> SEQ ID NO 55
<211> LENGTH: 20
<212> TYPE: DNA
<213> ORGANISM: ARTIFICIAL SEQUENCE
<220> FEATURE:
<223> OTHER INFORMATION: SYNTHETIC

<400> SEQUENCE: 55
actggggtcc tagcacgctg 20

<210> SEQ ID NO 56
<211> LENGTH: 20
<212> TYPE: DNA
<213> ORGANISM: ARTIFICIAL SEQUENCE
<220> FEATURE:
<223> OTHER INFORMATION: SYNTHETIC

<400> SEQUENCE: 56
cactggggtc ctagcacgct 20

<210> SEQ ID NO 57
<211> LENGTH: 20
<212> TYPE: DNA
<213> ORGANISM: ARTIFICIAL SEQUENCE
<220> FEATURE:
<223> OTHER INFORMATION: SYNTHETIC

<400> SEQUENCE: 57
acactggggt cctagcacgc 20

<210> SEQ ID NO 58
<211> LENGTH: 20
<212> TYPE: DNA
<213> ORGANISM: ARTIFICIAL SEQUENCE
<220> FEATURE:
<223> OTHER INFORMATION: SYNTHETIC

<400> SEQUENCE: 58
aacactgggg tcctagcacg 20

<210> SEQ ID NO 59
<211> LENGTH: 20
<212> TYPE: DNA
<213> ORGANISM: ARTIFICIAL SEQUENCE
<220> FEATURE:
<223> OTHER INFORMATION: SYNTHETIC

<400> SEQUENCE: 59
gaacactggg gtcctagcac 20

<210> SEQ ID NO 60
<211> LENGTH: 20
<212> TYPE: DNA
<213> ORGANISM: ARTIFICIAL SEQUENCE
<220> FEATURE:
<223> OTHER INFORMATION: SYNTHETIC

<400> SEQUENCE: 60
tgaacactgg ggtcctagca 20

<210> SEQ ID NO 61
<211> LENGTH: 20
<212> TYPE: DNA
<213> ORGANISM: ARTIFICIAL SEQUENCE
<220> FEATURE:
<223> OTHER INFORMATION: SYNTHETIC

<400> SEQUENCE: 61
ttgaacactg gggtcctagc 20

<210> SEQ ID NO 62
<211> LENGTH: 20
<212> TYPE: DNA
<213> ORGANISM: ARTIFICIAL SEQUENCE
<220> FEATURE:
<223> OTHER INFORMATION: SYNTHETIC

<400> SEQUENCE: 62
tttgaacact ggggtcctag 20

<210> SEQ ID NO 63
<211> LENGTH: 20
<212> TYPE: DNA
<213> ORGANISM: ARTIFICIAL SEQUENCE
<220> FEATURE:
<223> OTHER INFORMATION: SYNTHETIC

<400> SEQUENCE: 63
ttttgaacac tggggtccta 20

<210> SEQ ID NO 64
<211> LENGTH: 20
<212> TYPE: DNA

<213> ORGANISM: ARTIFICIAL SEQUENCE
<220> FEATURE:
<223> OTHER INFORMATION: SYNTHETIC

<400> SEQUENCE: 64
attttgaaca ctggggtcct 20

<210> SEQ ID NO 65
<211> LENGTH: 20
<212> TYPE: DNA
<213> ORGANISM: ARTIFICIAL SEQUENCE
<220> FEATURE:
<223> OTHER INFORMATION: SYNTHETIC

<400> SEQUENCE: 65
tattttgaac actggggtcc 20

<210> SEQ ID NO 66
<211> LENGTH: 20
<212> TYPE: DNA
<213> ORGANISM: ARTIFICIAL SEQUENCE
<220> FEATURE:
<223> OTHER INFORMATION: SYNTHETIC

<400> SEQUENCE: 66
ttattttgaa cactggggtc 20

<210> SEQ ID NO 67
<211> LENGTH: 20
<212> TYPE: DNA
<213> ORGANISM: ARTIFICIAL SEQUENCE
<220> FEATURE:
<223> OTHER INFORMATION: SYNTHETIC

<400> SEQUENCE: 67
cttattttga acactggggt 20

<210> SEQ ID NO 68
<211> LENGTH: 20
<212> TYPE: DNA
<213> ORGANISM: ARTIFICIAL SEQUENCE
<220> FEATURE:
<223> OTHER INFORMATION: SYNTHETIC

<400> SEQUENCE: 68
acttattttg aacactgggg 20

<210> SEQ ID NO 69
<211> LENGTH: 20
<212> TYPE: DNA
<213> ORGANISM: ARTIFICIAL SEQUENCE
<220> FEATURE:
<223> OTHER INFORMATION: SYNTHETIC

<400> SEQUENCE: 69
aacttatttt gaacactggg 20

<210> SEQ ID NO 70
<211> LENGTH: 20
<212> TYPE: DNA
<213> ORGANISM: ARTIFICIAL SEQUENCE
<220> FEATURE:
<223> OTHER INFORMATION: SYNTHETIC

<400> SEQUENCE: 70
aaacttattt tgaacactgg 20

<210> SEQ ID NO 71
<211> LENGTH: 20
<212> TYPE: DNA
<213> ORGANISM: ARTIFICIAL SEQUENCE
<220> FEATURE:
<223> OTHER INFORMATION: SYNTHETIC

<400> SEQUENCE: 71
caaacttatt ttgaacactg 20

<210> SEQ ID NO 72
<211> LENGTH: 20
<212> TYPE: DNA
<213> ORGANISM: ARTIFICIAL SEQUENCE
<220> FEATURE:
<223> OTHER INFORMATION: SYNTHETIC

<400> SEQUENCE: 72
acaaacttat tttgaacact 20

<210> SEQ ID NO 73
<211> LENGTH: 20
<212> TYPE: DNA
<213> ORGANISM: ARTIFICIAL SEQUENCE
<220> FEATURE:
<223> OTHER INFORMATION: SYNTHETIC

<400> SEQUENCE: 73
aacaaactta ttttgaacac 20

<210> SEQ ID NO 74
<211> LENGTH: 20
<212> TYPE: DNA
<213> ORGANISM: ARTIFICIAL SEQUENCE
<220> FEATURE:
<223> OTHER INFORMATION: SYNTHETIC

<400> SEQUENCE: 74
aaacaaactt attttgaaca 20

<210> SEQ ID NO 75
<211> LENGTH: 20
<212> TYPE: DNA
<213> ORGANISM: ARTIFICIAL SEQUENCE
<220> FEATURE:
<223> OTHER INFORMATION: SYNTHETIC

<400> SEQUENCE: 75
aaaacaaact tattttgaac 20

<210> SEQ ID NO 76
<211> LENGTH: 20
<212> TYPE: DNA
<213> ORGANISM: ARTIFICIAL SEQUENCE
<220> FEATURE:
<223> OTHER INFORMATION: SYNTHETIC

<400> SEQUENCE: 76
caaaacaaac ttattttgaa 20

<210> SEQ ID NO 77
<211> LENGTH: 20
<212> TYPE: DNA
<213> ORGANISM: ARTIFICIAL SEQUENCE
<220> FEATURE:

<223> OTHER INFORMATION: SYNTHETIC

<400> SEQUENCE: 77
gcaaaacaaa cttattttga 20

<210> SEQ ID NO 78
<211> LENGTH: 20
<212> TYPE: DNA
<213> ORGANISM: ARTIFICIAL SEQUENCE
<220> FEATURE:
<223> OTHER INFORMATION: SYNTHETIC

<400> SEQUENCE: 78
agcaaaacaa acttattttg 20

<210> SEQ ID NO 79
<211> LENGTH: 20
<212> TYPE: DNA
<213> ORGANISM: ARTIFICIAL SEQUENCE
<220> FEATURE:
<223> OTHER INFORMATION: SYNTHETIC

<400> SEQUENCE: 79
aagcaaaaca aacttatttt 20

<210> SEQ ID NO 80
<211> LENGTH: 20
<212> TYPE: DNA
<213> ORGANISM: ARTIFICIAL SEQUENCE
<220> FEATURE:
<223> OTHER INFORMATION: SYNTHETIC

<400> SEQUENCE: 80
caagcaaaac aaacttattt 20

<210> SEQ ID NO 81
<211> LENGTH: 20
<212> TYPE: DNA
<213> ORGANISM: ARTIFICIAL SEQUENCE
<220> FEATURE:
<223> OTHER INFORMATION: SYNTHETIC

<400> SEQUENCE: 81
acaagcaaaa caaacttatt 20

<210> SEQ ID NO 82
<211> LENGTH: 20
<212> TYPE: DNA
<213> ORGANISM: ARTIFICIAL SEQUENCE
<220> FEATURE:
<223> OTHER INFORMATION: SYNTHETIC

<400> SEQUENCE: 82
cacaagcaaa acaaacttat 20

<210> SEQ ID NO 83
<211> LENGTH: 20
<212> TYPE: DNA
<213> ORGANISM: ARTIFICIAL SEQUENCE
<220> FEATURE:
<223> OTHER INFORMATION: SYNTHETIC

<400> SEQUENCE: 83
tcacaagcaa aacaaactta 20

<210> SEQ ID NO 84
<211> LENGTH: 20
<212> TYPE: DNA
<213> ORGANISM: ARTIFICIAL SEQUENCE
<220> FEATURE:
<223> OTHER INFORMATION: SYNTHETIC

<400> SEQUENCE: 84
ctcacaagca aaacaaactt 20

<210> SEQ ID NO 85
<211> LENGTH: 20
<212> TYPE: DNA
<213> ORGANISM: ARTIFICIAL SEQUENCE
<220> FEATURE:
<223> OTHER INFORMATION: SYNTHETIC

<400> SEQUENCE: 85
gctcacaagc aaaacaaact 20

<210> SEQ ID NO 86
<211> LENGTH: 20
<212> TYPE: DNA
<213> ORGANISM: ARTIFICIAL SEQUENCE
<220> FEATURE:
<223> OTHER INFORMATION: SYNTHETIC

<400> SEQUENCE: 86
agctcacaag caaaacaaac 20

<210> SEQ ID NO 87
<211> LENGTH: 20
<212> TYPE: DNA
<213> ORGANISM: ARTIFICIAL SEQUENCE
<220> FEATURE:
<223> OTHER INFORMATION: SYNTHETIC

<400> SEQUENCE: 87
gagctcacaa gcaaaacaaa 20

<210> SEQ ID NO 88
<211> LENGTH: 20
<212> TYPE: DNA
<213> ORGANISM: ARTIFICIAL SEQUENCE
<220> FEATURE:
<223> OTHER INFORMATION: SYNTHETIC

<400> SEQUENCE: 88
agagctcaca agcaaaacaa 20

<210> SEQ ID NO 89
<211> LENGTH: 20
<212> TYPE: DNA
<213> ORGANISM: ARTIFICIAL SEQUENCE
<220> FEATURE:
<223> OTHER INFORMATION: SYNTHETIC

<400> SEQUENCE: 89
tagagctcac aagcaaaaca 20

<210> SEQ ID NO 90
<211> LENGTH: 20
<212> TYPE: DNA
<213> ORGANISM: ARTIFICIAL SEQUENCE
<220> FEATURE:
<223> OTHER INFORMATION: SYNTHETIC

<400> SEQUENCE: 90
gtagagctca caagcaaaac 20

<210> SEQ ID NO 91
<211> LENGTH: 20
<212> TYPE: DNA
<213> ORGANISM: ARTIFICIAL SEQUENCE
<220> FEATURE:
<223> OTHER INFORMATION: SYNTHETIC

<400> SEQUENCE: 91
tgtagagctc acaagcaaaa 20

<210> SEQ ID NO 92
<211> LENGTH: 20
<212> TYPE: DNA
<213> ORGANISM: ARTIFICIAL SEQUENCE
<220> FEATURE:
<223> OTHER INFORMATION: SYNTHETIC

<400> SEQUENCE: 92
gtgtagagct cacaagcaaa 20

<210> SEQ ID NO 93
<211> LENGTH: 20
<212> TYPE: DNA
<213> ORGANISM: ARTIFICIAL SEQUENCE
<220> FEATURE:
<223> OTHER INFORMATION: SYNTHETIC

<400> SEQUENCE: 93
tgtgtagagc tcacaagcaa 20

<210> SEQ ID NO 94
<211> LENGTH: 20
<212> TYPE: DNA
<213> ORGANISM: ARTIFICIAL SEQUENCE
<220> FEATURE:
<223> OTHER INFORMATION: SYNTHETIC

<400> SEQUENCE: 94
ttgtgtagag ctcacaagca 20

<210> SEQ ID NO 95
<211> LENGTH: 20
<212> TYPE: DNA
<213> ORGANISM: ARTIFICIAL SEQUENCE
<220> FEATURE:
<223> OTHER INFORMATION: SYNTHETIC

<400> SEQUENCE: 95
tttgtgtaga gctcacaagc 20

<210> SEQ ID NO 96
<211> LENGTH: 20
<212> TYPE: DNA
<213> ORGANISM: ARTIFICIAL SEQUENCE
<220> FEATURE:
<223> OTHER INFORMATION: SYNTHETIC

<400> SEQUENCE: 96
gtttgtgtag agctcacaag 20

<210> SEQ ID NO 97
<211> LENGTH: 20

```
<212> TYPE: DNA
<213> ORGANISM: ARTIFICIAL SEQUENCE
<220> FEATURE:
<223> OTHER INFORMATION: SYNTHETIC

<400> SEQUENCE: 97

ggtttgtgta gagctcacaa                                              20


<210> SEQ ID NO 98
<211> LENGTH: 20
<212> TYPE: DNA
<213> ORGANISM: ARTIFICIAL SEQUENCE
<220> FEATURE:
<223> OTHER INFORMATION: SYNTHETIC

<400> SEQUENCE: 98

cggtttgtgt agagctcaca                                              20


<210> SEQ ID NO 99
<211> LENGTH: 20
<212> TYPE: DNA
<213> ORGANISM: ARTIFICIAL SEQUENCE
<220> FEATURE:
<223> OTHER INFORMATION: SYNTHETIC

<400> SEQUENCE: 99

acggtttgtg tagagctcac                                              20


<210> SEQ ID NO 100
<211> LENGTH: 20
<212> TYPE: DNA
<213> ORGANISM: ARTIFICIAL SEQUENCE
<220> FEATURE:
<223> OTHER INFORMATION: SYNTHETIC

<400> SEQUENCE: 100

cacggtttgt gtagagctca                                              20


<210> SEQ ID NO 101
<211> LENGTH: 20
<212> TYPE: DNA
<213> ORGANISM: ARTIFICIAL SEQUENCE
<220> FEATURE:
<223> OTHER INFORMATION: SYNTHETIC

<400> SEQUENCE: 101

ccacggtttg tgtagagctc                                              20


<210> SEQ ID NO 102
<211> LENGTH: 20
<212> TYPE: DNA
<213> ORGANISM: ARTIFICIAL SEQUENCE
<220> FEATURE:
<223> OTHER INFORMATION: SYNTHETIC

<400> SEQUENCE: 102

cccacggttt gtgtagagct                                              20


<210> SEQ ID NO 103
<211> LENGTH: 20
<212> TYPE: DNA
<213> ORGANISM: ARTIFICIAL SEQUENCE
<220> FEATURE:
<223> OTHER INFORMATION: SYNTHETIC

<400> SEQUENCE: 103
```

acccacggtt tgtgtagagc 20

<210> SEQ ID NO 104
<211> LENGTH: 20
<212> TYPE: DNA
<213> ORGANISM: ARTIFICIAL SEQUENCE
<220> FEATURE:
<223> OTHER INFORMATION: SYNTHETIC

<400> SEQUENCE: 104
cacccacggt ttgtgtagag 20

<210> SEQ ID NO 105
<211> LENGTH: 20
<212> TYPE: DNA
<213> ORGANISM: ARTIFICIAL SEQUENCE
<220> FEATURE:
<223> OTHER INFORMATION: SYNTHETIC

<400> SEQUENCE: 105
ccacccacgg tttgtgtaga 20

<210> SEQ ID NO 106
<211> LENGTH: 20
<212> TYPE: DNA
<213> ORGANISM: ARTIFICIAL SEQUENCE
<220> FEATURE:
<223> OTHER INFORMATION: SYNTHETIC

<400> SEQUENCE: 106
tccacccacg gtttgtgtag 20

<210> SEQ ID NO 107
<211> LENGTH: 20
<212> TYPE: DNA
<213> ORGANISM: ARTIFICIAL SEQUENCE
<220> FEATURE:
<223> OTHER INFORMATION: SYNTHETIC

<400> SEQUENCE: 107
ttccacccac ggtttgtgta 20

<210> SEQ ID NO 108
<211> LENGTH: 20
<212> TYPE: DNA
<213> ORGANISM: ARTIFICIAL SEQUENCE
<220> FEATURE:
<223> OTHER INFORMATION: SYNTHETIC

<400> SEQUENCE: 108
cttccaccca cggtttgtgt 20

<210> SEQ ID NO 109
<211> LENGTH: 20
<212> TYPE: DNA
<213> ORGANISM: ARTIFICIAL SEQUENCE
<220> FEATURE:
<223> OTHER INFORMATION: SYNTHETIC

<400> SEQUENCE: 109
ccttccaccc acggtttgtg 20

<210> SEQ ID NO 110
<211> LENGTH: 20
<212> TYPE: DNA
<213> ORGANISM: ARTIFICIAL SEQUENCE

<220> FEATURE:
<223> OTHER INFORMATION: SYNTHETIC

<400> SEQUENCE: 110
cccttccacc cacggtttgt 20

<210> SEQ ID NO 111
<211> LENGTH: 20
<212> TYPE: DNA
<213> ORGANISM: ARTIFICIAL SEQUENCE
<220> FEATURE:
<223> OTHER INFORMATION: SYNTHETIC

<400> SEQUENCE: 111
ccccttccac ccacggtttg 20

<210> SEQ ID NO 112
<211> LENGTH: 20
<212> TYPE: DNA
<213> ORGANISM: ARTIFICIAL SEQUENCE
<220> FEATURE:
<223> OTHER INFORMATION: SYNTHETIC

<400> SEQUENCE: 112
cccccttcca cccacggttt 20

<210> SEQ ID NO 113
<211> LENGTH: 20
<212> TYPE: DNA
<213> ORGANISM: ARTIFICIAL SEQUENCE
<220> FEATURE:
<223> OTHER INFORMATION: SYNTHETIC

<400> SEQUENCE: 113
acccccttcc acccacggtt 20

<210> SEQ ID NO 114
<211> LENGTH: 20
<212> TYPE: DNA
<213> ORGANISM: ARTIFICIAL SEQUENCE
<220> FEATURE:
<223> OTHER INFORMATION: SYNTHETIC

<400> SEQUENCE: 114 taccccottc cacccacggt 20

<210> SEQ ID NO 115
<211> LENGTH: 20
<212> TYPE: DNA
<213> ORGANISM: ARTIFICIAL SEQUENCE
<220> FEATURE:
<223> OTHER INFORMATION: SYNTHETIC

<400> SEQUENCE: 115
ttaccccctt ccacccacgg 20

<210> SEQ ID NO 116
<211> LENGTH: 20
<212> TYPE: DNA
<213> ORGANISM: ARTIFICIAL SEQUENCE
<220> FEATURE:
<223> OTHER INFORMATION: SYNTHETIC

<400> SEQUENCE: 116 tttacccccct tccacccacg 20

<210> SEQ ID NO 117
<211> LENGTH: 20
<212> TYPE: DNA
<213> ORGANISM: ARTIFICIAL SEQUENCE
<220> FEATURE:
<223> OTHER INFORMATION: SYNTHETIC

<400> SEQUENCE: 117
ctttaccccc ttccacccac 20

<210> SEQ ID NO 118
<211> LENGTH: 20
<212> TYPE: DNA
<213> ORGANISM: ARTIFICIAL SEQUENCE
<220> FEATURE:
<223> OTHER INFORMATION: SYNTHETIC

<400> SEQUENCE: 118
cctttacccc cttccaccca 20

<210> SEQ ID NO 119
<211> LENGTH: 20
<212> TYPE: DNA
<213> ORGANISM: ARTIFICIAL SEQUENCE
<220> FEATURE:
<223> OTHER INFORMATION: SYNTHETIC

<400> SEQUENCE: 119
ccctttaccc ccttccaccc 20

<210> SEQ ID NO 120
<211> LENGTH: 20
<212> TYPE: DNA
<213> ORGANISM: ARTIFICIAL SEQUENCE
<220> FEATURE:
<223> OTHER INFORMATION: SYNTHETIC

<400> SEQUENCE: 120
tccctttacc cccttccacc 20

<210> SEQ ID NO 121
<211> LENGTH: 20
<212> TYPE: DNA
<213> ORGANISM: ARTIFICIAL SEQUENCE
<220> FEATURE:
<223> OTHER INFORMATION: SYNTHETIC

<400> SEQUENCE: 121
atccctttac ccccttccac 20

<210> SEQ ID NO 122
<211> LENGTH: 20
<212> TYPE: DNA
<213> ORGANISM: ARTIFICIAL SEQUENCE
<220> FEATURE:
<223> OTHER INFORMATION: SYNTHETIC

<400> SEQUENCE: 122
gatcccttta cccccttcca 20

<210> SEQ ID NO 123
<211> LENGTH: 20
<212> TYPE: DNA
<213> ORGANISM: ARTIFICIAL SEQUENCE
<220> FEATURE:
<223> OTHER INFORMATION: SYNTHETIC

<400> SEQUENCE: 123
tgatcccttt acccccttcc 20

<210> SEQ ID NO 124
<211> LENGTH: 20
<212> TYPE: DNA
<213> ORGANISM: ARTIFICIAL SEQUENCE
<220> FEATURE:
<223> OTHER INFORMATION: SYNTHETIC

<400> SEQUENCE: 124
ctgatccctt tacccccttc 20

<210> SEQ ID NO 125
<211> LENGTH: 19
<212> TYPE: DNA
<213> ORGANISM: ARTIFICIAL SEQUENCE
<220> FEATURE:
<223> OTHER INFORMATION: SYNTHETIC

<400> SEQUENCE: 125
cctgatccct ttccccctt 19

<210> SEQ ID NO 126
<211> LENGTH: 20
<212> TYPE: DNA
<213> ORGANISM: ARTIFICIAL SEQUENCE
<220> FEATURE:
<223> OTHER INFORMATION: SYNTHETIC

<400> SEQUENCE: 126
acctgatccc tttaccccct 20

<210> SEQ ID NO 127
<211> LENGTH: 20
<212> TYPE: DNA
<213> ORGANISM: ARTIFICIAL SEQUENCE
<220> FEATURE:
<223> OTHER INFORMATION: SYNTHETIC

<400> SEQUENCE: 127
aacctgatcc ctttaccccc 20

<210> SEQ ID NO 128
<211> LENGTH: 20
<212> TYPE: DNA
<213> ORGANISM: ARTIFICIAL SEQUENCE
<220> FEATURE:
<223> OTHER INFORMATION: SYNTHETIC

<400> SEQUENCE: 128
aaacctgatc cctttacccc 20

<210> SEQ ID NO 129
<211> LENGTH: 20
<212> TYPE: DNA
<213> ORGANISM: ARTIFICIAL SEQUENCE
<220> FEATURE:
<223> OTHER INFORMATION: SYNTHETIC

<400> SEQUENCE: 129
aaaacctgat ccctttaccc 20

<210> SEQ ID NO 130

<211> LENGTH: 20
<212> TYPE: DNA
<213> ORGANISM: ARTIFICIAL SEQUENCE
<220> FEATURE:
<223> OTHER INFORMATION: SYNTHETIC

<400> SEQUENCE: 130
gaaaacctga tccctttacc 20

<210> SEQ ID NO 131
<211> LENGTH: 20
<212> TYPE: DNA
<213> ORGANISM: ARTIFICIAL SEQUENCE
<220> FEATURE:
<223> OTHER INFORMATION: SYNTHETIC

<400> SEQUENCE: 131
agaaaacctg atccctttac 20

<210> SEQ ID NO 132
<211> LENGTH: 20
<212> TYPE: DNA
<213> ORGANISM: ARTIFICIAL SEQUENCE
<220> FEATURE:
<223> OTHER INFORMATION: SYNTHETIC

<400> SEQUENCE: 132
tagaaaacct gatcccttta 20

<210> SEQ ID NO 133
<211> LENGTH: 20
<212> TYPE: DNA
<213> ORGANISM: ARTIFICIAL SEQUENCE
<220> FEATURE:
<223> OTHER INFORMATION: SYNTHETIC

<400> SEQUENCE: 133
gtagaaaacc tgatcccttt 20

<210> SEQ ID NO 134
<211> LENGTH: 20
<212> TYPE: DNA
<213> ORGANISM: ARTIFICIAL SEQUENCE
<220> FEATURE:
<223> OTHER INFORMATION: SYNTHETIC

<400> SEQUENCE: 134
agtagaaaac ctgatccctt 20

<210> SEQ ID NO 135
<211> LENGTH: 20
<212> TYPE: DNA
<213> ORGANISM: ARTIFICIAL SEQUENCE
<220> FEATURE:
<223> OTHER INFORMATION: SYNTHETIC

<400> SEQUENCE: 135
tagtagaaaa cctgatccct 20

<210> SEQ ID NO 136
<211> LENGTH: 20
<212> TYPE: DNA
<213> ORGANISM: ARTIFICIAL SEQUENCE
<220> FEATURE:
<223> OTHER INFORMATION: SYNTHETIC

<400> SEQUENCE: 136
atagtagaaa acctgatccc 20

<210> SEQ ID NO 137
<211> LENGTH: 20
<212> TYPE: DNA
<213> ORGANISM: ARTIFICIAL SEQUENCE
<220> FEATURE:
<223> OTHER INFORMATION: SYNTHETIC

<400> SEQUENCE: 137
catagtagaa aacctgatcc 20

<210> SEQ ID NO 138
<211> LENGTH: 20
<212> TYPE: DNA
<213> ORGANISM: ARTIFICIAL SEQUENCE
<220> FEATURE:
<223> OTHER INFORMATION: SYNTHETIC

<400> SEQUENCE: 138
acatagtaga aaacctgatc 20

<210> SEQ ID NO 139
<211> LENGTH: 20
<212> TYPE: DNA
<213> ORGANISM: ARTIFICIAL SEQUENCE
<220> FEATURE:
<223> OTHER INFORMATION: SYNTHETIC

<400> SEQUENCE: 139
aacatagtag aaaacctgat 20

<210> SEQ ID NO 140
<211> LENGTH: 20
<212> TYPE: DNA
<213> ORGANISM: ARTIFICIAL SEQUENCE
<220> FEATURE:
<223> OTHER INFORMATION: SYNTHETIC

<400> SEQUENCE: 140
aaacatagta gaaaacctga 20

<210> SEQ ID NO 141
<211> LENGTH: 20
<212> TYPE: DNA
<213> ORGANISM: ARTIFICIAL SEQUENCE
<220> FEATURE:
<223> OTHER INFORMATION: SYNTHETIC

<400> SEQUENCE: 141
caaacatagt agaaaacctg 20

<210> SEQ ID NO 142
<211> LENGTH: 20
<212> TYPE: DNA
<213> ORGANISM: ARTIFICIAL SEQUENCE
<220> FEATURE:
<223> OTHER INFORMATION: SYNTHETIC

<400> SEQUENCE: 142
acaaacatag tagaaaacct 20

<210> SEQ ID NO 143
<211> LENGTH: 20
<212> TYPE: DNA

<213> ORGANISM: ARTIFICIAL SEQUENCE
<220> FEATURE:
<223> OTHER INFORMATION: SYNTHETIC

<400> SEQUENCE: 143
gacaaacata gtagaaaacc 20

<210> SEQ ID NO 144
<211> LENGTH: 20
<212> TYPE: DNA
<213> ORGANISM: ARTIFICIAL SEQUENCE
<220> FEATURE:
<223> OTHER INFORMATION: SYNTHETIC

<400> SEQUENCE: 144
ggacaaacat agtagaaaac 20

<210> SEQ ID NO 145
<211> LENGTH: 20
<212> TYPE: DNA
<213> ORGANISM: ARTIFICIAL SEQUENCE
<220> FEATURE:
<223> OTHER INFORMATION: SYNTHETIC

<400> SEQUENCE: 145
gggacaaaca tagtagaaaa 20

<210> SEQ ID NO 146
<211> LENGTH: 20
<212> TYPE: DNA
<213> ORGANISM: ARTIFICIAL SEQUENCE
<220> FEATURE:
<223> OTHER INFORMATION: SYNTHETIC

<400> SEQUENCE: 146
cgggacaaac atagtagaaa 20

<210> SEQ ID NO 147
<211> LENGTH: 20
<212> TYPE: DNA
<213> ORGANISM: ARTIFICIAL SEQUENCE
<220> FEATURE:
<223> OTHER INFORMATION: SYNTHETIC

<400> SEQUENCE: 147
acgggacaaa catagtagaa 20

<210> SEQ ID NO 148
<211> LENGTH: 20
<212> TYPE: DNA
<213> ORGANISM: ARTIFICIAL SEQUENCE
<220> FEATURE:
<223> OTHER INFORMATION: SYNTHETIC

<400> SEQUENCE: 148
cacgggacaa acatagtaga 20

<210> SEQ ID NO 149
<211> LENGTH: 20
<212> TYPE: DNA
<213> ORGANISM: ARTIFICIAL SEQUENCE
<220> FEATURE:
<223> OTHER INFORMATION: SYNTHETIC

<400> SEQUENCE: 149
ccacgggaca aacatagtag 20

<210> SEQ ID NO 150
<211> LENGTH: 20
<212> TYPE: DNA
<213> ORGANISM: ARTIFICIAL SEQUENCE
<220> FEATURE:
<223> OTHER INFORMATION: SEQUENCE

<400> SEQUENCE: 150
accacgggac aaacatagta 20

<210> SEQ ID NO 151
<211> LENGTH: 20
<212> TYPE: DNA
<213> ORGANISM: ARTIFICIAL SEQUENCE
<220> FEATURE:
<223> OTHER INFORMATION: SYNTHETIC

<400> SEQUENCE: 151
caccacggga caaacatagt 20

<210> SEQ ID NO 152
<211> LENGTH: 20
<212> TYPE: DNA
<213> ORGANISM: ARTIFICIAL SEQUENCE
<220> FEATURE:
<223> OTHER INFORMATION: SYNTHETIC

<400> SEQUENCE: 152
tcaccacggg acaaacatag 20

<210> SEQ ID NO 153
<211> LENGTH: 20
<212> TYPE: DNA
<213> ORGANISM: ARTIFICIAL SEQUENCE
<220> FEATURE:
<223> OTHER INFORMATION: SYNTHETIC

<400> SEQUENCE: 153
atcaccacgg gacaaacata 20

<210> SEQ ID NO 154
<211> LENGTH: 20
<212> TYPE: DNA
<213> ORGANISM: ARTIFICIAL SEQUENCE
<220> FEATURE:
<223> OTHER INFORMATION: SYNTHETIC

<400> SEQUENCE: 154
catcaccacg ggacaaacat 20

<210> SEQ ID NO 155
<211> LENGTH: 20
<212> TYPE: DNA
<213> ORGANISM: ARTIFICIAL SEQUENCE
<220> FEATURE:
<223> OTHER INFORMATION: SYNTHETIC

<400> SEQUENCE: 155
ccatcaccac gggacaaaca 20

<210> SEQ ID NO 156
<211> LENGTH: 20
<212> TYPE: DNA
<213> ORGANISM: ARTIFICIAL SEQUENCE
<220> FEATURE:

<223> OTHER INFORMATION: SYNTHETIC

<400> SEQUENCE: 156
tccatcacca cgggacaaac 20

<210> SEQ ID NO 157
<211> LENGTH: 20
<212> TYPE: DNA
<213> ORGANISM: ARTIFICIAL SEQUENCE
<220> FEATURE:
<223> OTHER INFORMATION: SYNTHETIC

<400> SEQUENCE: 157
gtccatcacc acgggacaaa 20

<210> SEQ ID NO 158
<211> LENGTH: 20
<212> TYPE: DNA
<213> ORGANISM: ARTIFICIAL SEQUENCE
<220> FEATURE:
<223> OTHER INFORMATION: SYNTHETIC

<400> SEQUENCE: 158
agtccatcac cacgggacaa 20

<210> SEQ ID NO 159
<211> LENGTH: 20
<212> TYPE: DNA
<213> ORGANISM: ARTIFICIAL SEQUENCE
<220> FEATURE:
<223> OTHER INFORMATION: SYNTHETIC

<400> SEQUENCE: 159
cagtccatca ccacgggaca 20

<210> SEQ ID NO 160
<211> LENGTH: 20
<212> TYPE: DNA
<213> ORGANISM: ARTIFICIAL SEQUENCE
<220> FEATURE:
<223> OTHER INFORMATION: SYNTHETIC

<400> SEQUENCE: 160
ccagtccatc accacgggac 20

<210> SEQ ID NO 161
<211> LENGTH: 20
<212> TYPE: DNA
<213> ORGANISM: ARTIFICIAL SEQUENCE
<220> FEATURE:
<223> OTHER INFORMATION: SYNTHETIC

<400> SEQUENCE: 161
cccagtccat caccacggga 20

<210> SEQ ID NO 162
<211> LENGTH: 20
<212> TYPE: DNA
<213> ORGANISM: ARTIFICIAL SEQUENCE
<220> FEATURE:
<223> OTHER INFORMATION: SYNTHETIC

<400> SEQUENCE: 162
tcccagtcca tcaccacggg 20

<210> SEQ ID NO 163
<211> LENGTH: 20
<212> TYPE: DNA
<213> ORGANISM: ARTIFICIAL SEQUENCE
<220> FEATURE:
<223> OTHER INFORMATION: SYNTHETIC

<400> SEQUENCE: 163
gtcccagtcc atcaccacgg 20

<210> SEQ ID NO 164
<211> LENGTH: 20
<212> TYPE: DNA
<213> ORGANISM: ARTIFICIAL SEQUENCE
<220> FEATURE:
<223> OTHER INFORMATION: SYNTHETIC

<400> SEQUENCE: 164
tgtcccagtc catcaccacg 20

<210> SEQ ID NO 165
<211> LENGTH: 20
<212> TYPE: DNA
<213> ORGANISM: ARTIFICIAL SEQUENCE
<220> FEATURE:
<223> OTHER INFORMATION: SYNTHETIC

<400> SEQUENCE: 165
ctgtcccagt ccatcaccac 20

<210> SEQ ID NO 166
<211> LENGTH: 20
<212> TYPE: DNA
<213> ORGANISM: ARTIFICIAL SEQUENCE
<220> FEATURE:
<223> OTHER INFORMATION: SYNTHETIC

<400> SEQUENCE: 166
cctgtcccag tccatcacca 20

<210> SEQ ID NO 167
<211> LENGTH: 20
<212> TYPE: DNA
<213> ORGANISM: ARTIFICIAL SEQUENCE
<220> FEATURE:
<223> OTHER INFORMATION: SYNTHETIC

<400> SEQUENCE: 167
tcctgtccca gtccatcacc 20

<210> SEQ ID NO 168
<211> LENGTH: 20
<212> TYPE: DNA
<213> ORGANISM: ARTIFICIAL SEQUENCE
<220> FEATURE:
<223> OTHER INFORMATION: SYNTHETIC

<400> SEQUENCE: 168
ctcctgtccc agtccatcac 20

<210> SEQ ID NO 169
<211> LENGTH: 20
<212> TYPE: DNA
<213> ORGANISM: ARTIFICIAL SEQUENCE
<220> FEATURE:
<223> OTHER INFORMATION: SYNTHETIC

<400> SEQUENCE: 169
gctcctgtcc cagtccatca 20

<210> SEQ ID NO 170
<211> LENGTH: 20
<212> TYPE: DNA
<213> ORGANISM: ARTIFICIAL SEQUENCE
<220> FEATURE:
<223> OTHER INFORMATION: SYNTHETIC

<400> SEQUENCE: 170
agctcctgtc ccagtccatc 20

<210> SEQ ID NO 171
<211> LENGTH: 20
<212> TYPE: DNA
<213> ORGANISM: ARTIFICIAL SEQUENCE
<220> FEATURE:
<223> OTHER INFORMATION: SYNTHETIC

<400> SEQUENCE: 171
tagctcctgt cccagtccat 20

<210> SEQ ID NO 172
<211> LENGTH: 20
<212> TYPE: DNA
<213> ORGANISM: ARTIFICIAL SEQUENCE
<220> FEATURE:
<223> OTHER INFORMATION: SYNTHETIC

<400> SEQUENCE: 172
ttagctcctg tcccagtcca 20

<210> SEQ ID NO 173
<211> LENGTH: 19
<212> TYPE: RNA
<213> ORGANISM: ARTIFICIAL SEQUENCE
<220> FEATURE:
<223> OTHER INFORMATION: SYNTHETIC

<400> SEQUENCE: 173
gccgaugacc ugcaagagu 19

<210> SEQ ID NO 174
<211> LENGTH: 18
<212> TYPE: RNA
<213> ORGANISM: ARTIFICIAL SEQUENCE
<220> FEATURE:
<223> OTHER INFORMATION: SYNTHETIC

<400> SEQUENCE: 174
auaacuuugc aacagugg 18

<210> SEQ ID NO 175
<211> LENGTH: 19
<212> TYPE: RNA
<213> ORGANISM: ARTIFICIAL SEQUENCE
<220> FEATURE:
<223> OTHER INFORMATION: SYNTHETIC

<400> SEQUENCE: 175
acucuugcag gucaucggc 19

<210> SEQ ID NO 176
<211> LENGTH: 18

<212> TYPE: RNA
<213> ORGANISM: ARTIFICIAL SEQUENCE
<220> FEATURE:
<223> OTHER INFORMATION: SYNTHETIC

<400> SEQUENCE: 176
ccacuguugc aaaguuau 18

<210> SEQ ID NO 177
<211> LENGTH: 20
<212> TYPE: RNA
<213> ORGANISM: ARTIFICIAL SEQUENCE
<220> FEATURE:
<223> OTHER INFORMATION: SYNTHETIC

<400> SEQUENCE: 177
uaugaagggc uggcugugcg 20

<210> SEQ ID NO 178
<211> LENGTH: 20
<212> TYPE: RNA
<213> ORGANISM: ARTIFICIAL SEQUENCE
<220> FEATURE:
<223> OTHER INFORMATION: SYNTHETIC

<400> SEQUENCE: 178
augaagggcu ggcugugcgg 20

<210> SEQ ID NO 179
<211> LENGTH: 20
<212> TYPE: RNA
<213> ORGANISM: ARTIFICIAL SEQUENCE
<220> FEATURE:
<223> OTHER INFORMATION: SYNTHETIC

<400> SEQUENCE: 179
augaagggcu ggcugugcgg 20

<210> SEQ ID NO 180
<211> LENGTH: 20
<212> TYPE: RNA
<213> ORGANISM: ARTIFICIAL SEQUENCE
<220> FEATURE:
<223> OTHER INFORMATION: SYNTHETIC

<400> SEQUENCE: 180
gaagggcugg cugugcggca 20

<210> SEQ ID NO 181
<211> LENGTH: 20
<212> TYPE: RNA
<213> ORGANISM: ARTIFICIAL SEQUENCE
<220> FEATURE:
<223> OTHER INFORMATION: SYNTHETIC

<400> SEQUENCE: 181
aagggcuggc ugugcggcac 20

<210> SEQ ID NO 182
<211> LENGTH: 20
<212> TYPE: RNA
<213> ORGANISM: ARTIFICIAL SEQUENCE
<220> FEATURE:
<223> OTHER INFORMATION: SYNTHETIC

<400> SEQUENCE: 182
agggcuggcu gugcggcaca 20

<210> SEQ ID NO 183
<211> LENGTH: 20
<212> TYPE: RNA
<213> ORGANISM: ARTIFICIAL SEQUENCE
<220> FEATURE:
<223> OTHER INFORMATION: SYNTHETIC

<400> SEQUENCE: 183
gggcuggcug ugcggcacag 20

<210> SEQ ID NO 184
<211> LENGTH: 20
<212> TYPE: RNA
<213> ORGANISM: ARTIFICIAL SEQUENCE
<220> FEATURE:
<223> OTHER INFORMATION: SYNTHETIC

<400> SEQUENCE: 184
ggcuggcugu gcggcacagg 20

<210> SEQ ID NO 185
<211> LENGTH: 20
<212> TYPE: RNA
<213> ORGANISM: ARTIFICIAL SEQUENCE
<220> FEATURE:
<223> OTHER INFORMATION: SYNTHETIC

<400> SEQUENCE: 185
gcuggcugug cggcacaggu 20

<210> SEQ ID NO 186
<211> LENGTH: 20
<212> TYPE: RNA
<213> ORGANISM: ARTIFICIAL SEQUENCE
<220> FEATURE:
<223> OTHER INFORMATION: SYNTHETIC

<400> SEQUENCE: 186
cuggcugugc ggcacagguu 20

<210> SEQ ID NO 187
<211> LENGTH: 20
<212> TYPE: RNA
<213> ORGANISM: ARTIFICIAL SEQUENCE
<220> FEATURE:
<223> OTHER INFORMATION: SYNTHETIC

<400> SEQUENCE: 187
uggcugugcg gcacagguua 20

<210> SEQ ID NO 188
<211> LENGTH: 20
<212> TYPE: RNA
<213> ORGANISM: ARTIFICIAL SEQUENCE
<220> FEATURE:
<223> OTHER INFORMATION: SYNTHETIC

<400> SEQUENCE: 188
ggcugugcgg cacagguuaa 20

<210> SEQ ID NO 189
<211> LENGTH: 20
<212> TYPE: RNA
<213> ORGANISM: ARTIFICIAL SEQUENCE

<220> FEATURE:
<223> OTHER INFORMATION: SYNTHETIC

<400> SEQUENCE: 189
gcugugcggc acagguuaau 20

<210> SEQ ID NO 190
<211> LENGTH: 20
<212> TYPE: RNA
<213> ORGANISM: ARTIFICIAL SEQUENCE
<220> FEATURE:
<223> OTHER INFORMATION: SYNTHETIC

<400> SEQUENCE: 190
cugugcggca cagguuaaug 20

<210> SEQ ID NO 191
<211> LENGTH: 20
<212> TYPE: RNA
<213> ORGANISM: ARTIFICIAL SEQUENCE
<220> FEATURE:
<223> OTHER INFORMATION: SYNTHETIC

<400> SEQUENCE: 191
ugugcggcac agguuaauga 20

<210> SEQ ID NO 192
<211> LENGTH: 20
<212> TYPE: RNA
<213> ORGANISM: ARTIFICIAL SEQUENCE
<220> FEATURE:
<223> OTHER INFORMATION: SYNTHETIC

<400> SEQUENCE: 192
gugcggcaca gguuaaugau 20

<210> SEQ ID NO 193
<211> LENGTH: 20
<212> TYPE: RNA
<213> ORGANISM: ARTIFICIAL SEQUENCE
<220> FEATURE:
<223> OTHER INFORMATION: SYNTHETIC

<400> SEQUENCE: 193
ugcggcacag guuaaugauu 20

<210> SEQ ID NO 194
<211> LENGTH: 20
<212> TYPE: RNA
<213> ORGANISM: ARTIFICIAL SEQUENCE
<220> FEATURE:
<223> OTHER INFORMATION: SYNTHETIC

<400> SEQUENCE: 194
gcggcacagg uuaaugauug 20

<210> SEQ ID NO 195
<211> LENGTH: 20
<212> TYPE: RNA
<213> ORGANISM: ARTIFICIAL SEQUENCE
<220> FEATURE:
<223> OTHER INFORMATION: SYNTHETIC

<400> SEQUENCE: 195
cggcacaggu uaaugauugu 20

<210> SEQ ID NO 196
<211> LENGTH: 20
<212> TYPE: RNA
<213> ORGANISM: ARTIFICIAL SEQUENCE
<220> FEATURE:
<223> OTHER INFORMATION: SYNTHETIC

<400> SEQUENCE: 196
ggcacagguu aaugauuguc 20

<210> SEQ ID NO 197
<211> LENGTH: 20
<212> TYPE: RNA
<213> ORGANISM: ARTIFICIAL SEQUENCE
<220> FEATURE:
<223> OTHER INFORMATION: SYNTHETIC

<400> SEQUENCE: 197
gcacagguua augauuguca 20

<210> SEQ ID NO 198
<211> LENGTH: 20
<212> TYPE: RNA
<213> ORGANISM: ARTIFICIAL SEQUENCE
<220> FEATURE:
<223> OTHER INFORMATION: SYNTHETIC

<400> SEQUENCE: 198
cacagguuaa ugauugucag 20

<210> SEQ ID NO 199
<211> LENGTH: 20
<212> TYPE: RNA
<213> ORGANISM: ARTIFICIAL SEQUENCE
<220> FEATURE:
<223> OTHER INFORMATION: SYNTHETIC

<400> SEQUENCE: 199
acagguuaau gauugucagg 20

<210> SEQ ID NO 200
<211> LENGTH: 20
<212> TYPE: RNA
<213> ORGANISM: ARTIFICIAL SEQUENCE
<220> FEATURE:
<223> OTHER INFORMATION: SYNTHETIC

<400> SEQUENCE: 200
cagguuaaug auugucaggg 20

<210> SEQ ID NO 201
<211> LENGTH: 20
<212> TYPE: RNA
<213> ORGANISM: ARTIFICIAL SEQUENCE
<220> FEATURE:
<223> OTHER INFORMATION: SYNTHETIC

<400> SEQUENCE: 201
agguuaauga uugucagggc 20

<210> SEQ ID NO 202
<211> LENGTH: 20
<212> TYPE: RNA
<213> ORGANISM: ARTIFICIAL SEQUENCE
<220> FEATURE:
<223> OTHER INFORMATION: SYNTHETIC

<400> SEQUENCE: 202
gguuaaugau ugucagggca 20

<210> SEQ ID NO 203
<211> LENGTH: 20
<212> TYPE: RNA
<213> ORGANISM: ARTIFICIAL SEQUENCE
<220> FEATURE:
<223> OTHER INFORMATION: SYNTHETIC

<400> SEQUENCE: 203
guuaaugauu gucagggcag 20

<210> SEQ ID NO 204
<211> LENGTH: 20
<212> TYPE: RNA
<213> ORGANISM: ARTIFICIAL SEQUENCE
<220> FEATURE:
<223> OTHER INFORMATION: SYNTHETIC

<400> SEQUENCE: 204
uuaaugauug ucagggcagc 20

<210> SEQ ID NO 205
<211> LENGTH: 20
<212> TYPE: RNA
<213> ORGANISM: ARTIFICIAL SEQUENCE
<220> FEATURE:
<223> OTHER INFORMATION: SYNTHETIC

<400> SEQUENCE: 205
uaaugauugu cagggcagcg 20

<210> SEQ ID NO 206
<211> LENGTH: 20
<212> TYPE: RNA
<213> ORGANISM: ARTIFICIAL SEQUENCE
<220> FEATURE:
<223> OTHER INFORMATION: SYNTHETIC

<400> SEQUENCE: 206
aaugauuguc agggcagcgu 20

<210> SEQ ID NO 207
<211> LENGTH: 20
<212> TYPE: RNA
<213> ORGANISM: ARTIFICIAL SEQUENCE
<220> FEATURE:
<223> OTHER INFORMATION: SYNTHETIC

<400> SEQUENCE: 207
augauuguca gggcagcgug 20

<210> SEQ ID NO 208
<211> LENGTH: 20
<212> TYPE: RNA
<213> ORGANISM: ARTIFICIAL SEQUENCE
<220> FEATURE:
<223> OTHER INFORMATION: SYNTHETIC

<400> SEQUENCE: 208
ugauugucag ggcagcgugc 20

<210> SEQ ID NO 209

<211> LENGTH: 20
<212> TYPE: RNA
<213> ORGANISM: ARTIFICIAL SEQUENCE
<220> FEATURE:
<223> OTHER INFORMATION: SYNTHETIC

<400> SEQUENCE: 209
gauugucagg gcagcgugcu 20

<210> SEQ ID NO 210
<211> LENGTH: 20
<212> TYPE: RNA
<213> ORGANISM: ARTIFICIAL SEQUENCE
<220> FEATURE:
<223> OTHER INFORMATION: SYNTHETIC

<400> SEQUENCE: 210
auugucaggg cagcgugcua 20

<210> SEQ ID NO 211
<211> LENGTH: 20
<212> TYPE: RNA
<213> ORGANISM: ARTIFICIAL SEQUENCE
<220> FEATURE:
<223> OTHER INFORMATION: SYNTHETIC

<400> SEQUENCE: 211
uugucagggc agcgugcuag 20

<210> SEQ ID NO 212
<211> LENGTH: 20
<212> TYPE: RNA
<213> ORGANISM: ARTIFICIAL SEQUENCE
<220> FEATURE:
<223> OTHER INFORMATION: SEQUENCE

<400> SEQUENCE: 212
ugucagggca gcgugcuagg 20

<210> SEQ ID NO 213
<211> LENGTH: 20
<212> TYPE: RNA
<213> ORGANISM: ARTIFICIAL SEQUENCE
<220> FEATURE:
<223> OTHER INFORMATION: SYNTHETIC

<400> SEQUENCE: 213
gucagggcag cgugcuagga 20

<210> SEQ ID NO 214
<211> LENGTH: 20
<212> TYPE: RNA
<213> ORGANISM: ARTIFICIAL SEQUENCE
<220> FEATURE:
<223> OTHER INFORMATION: SYNTHETIC

<400> SEQUENCE: 214
ucagggcagc gugcuaggac 20

<210> SEQ ID NO 215
<211> LENGTH: 20
<212> TYPE: RNA
<213> ORGANISM: ARTIFICIAL SEQUENCE
<220> FEATURE:
<223> OTHER INFORMATION: SYNTHETIC

<400> SEQUENCE: 215
cagggcagcg ugcuaggacc 20

<210> SEQ ID NO 216
<211> LENGTH: 20
<212> TYPE: RNA
<213> ORGANISM: ARTIFICIAL SEQUENCE
<220> FEATURE:
<223> OTHER INFORMATION: SYNTHETIC

<400> SEQUENCE: 216
agggcagcgu gcuaggaccc 20

<210> SEQ ID NO 217
<211> LENGTH: 20
<212> TYPE: RNA
<213> ORGANISM: ARTIFICIAL SEQUENCE
<220> FEATURE:
<223> OTHER INFORMATION: SYNTHETIC

<400> SEQUENCE: 217
gggcagcgug cuaggacccc 20

<210> SEQ ID NO 218
<211> LENGTH: 20
<212> TYPE: RNA
<213> ORGANISM: ARTIFICIAL SEQUENCE
<220> FEATURE:
<223> OTHER INFORMATION: SYNTHETIC

<400> SEQUENCE: 218
ggcagcgugc uaggacccca 20

<210> SEQ ID NO 219
<211> LENGTH: 20
<212> TYPE: RNA
<213> ORGANISM: ARTIFICIAL SEQUENCE
<220> FEATURE:
<223> OTHER INFORMATION: SYNTHETIC

<400> SEQUENCE: 219
gcagcgugcu aggaccccag 20

<210> SEQ ID NO 220
<211> LENGTH: 20
<212> TYPE: RNA
<213> ORGANISM: ARTIFICIAL SEQUENCE
<220> FEATURE:
<223> OTHER INFORMATION: SYNTHETIC

<400> SEQUENCE: 220
cagcgugcua ggaccccagu 20

<210> SEQ ID NO 221
<211> LENGTH: 20
<212> TYPE: RNA
<213> ORGANISM: ARTIFICIAL SEQUENCE
<220> FEATURE:
<223> OTHER INFORMATION: SYNTHETIC

<400> SEQUENCE: 221
agcgugcuag gaccccagug 20

<210> SEQ ID NO 222
<211> LENGTH: 20
<212> TYPE: RNA

<213> ORGANISM: ARTIFICIAL SEQUENCE
<220> FEATURE:
<223> OTHER INFORMATION: SYNTHETIC

<400> SEQUENCE: 222
gcgugcuagg accccagugu 20

<210> SEQ ID NO 223
<211> LENGTH: 20
<212> TYPE: RNA
<213> ORGANISM: ARTIFICIAL SEQUENCE
<220> FEATURE:
<223> OTHER INFORMATION: SYNTHETIC

<400> SEQUENCE: 223
cgugcuagga ccccaguguu 20

<210> SEQ ID NO 224
<211> LENGTH: 20
<212> TYPE: RNA
<213> ORGANISM: ARTIFICIAL SEQUENCE
<220> FEATURE:
<223> OTHER INFORMATION: SYNTHETIC

<400> SEQUENCE: 224
gugcuaggac cccaguguuc 20

<210> SEQ ID NO 225
<211> LENGTH: 20
<212> TYPE: RNA
<213> ORGANISM: ARTIFICIAL SEQUENCE
<220> FEATURE:
<223> OTHER INFORMATION: SYNTHETIC

<400> SEQUENCE: 225
ugcuaggacc ccaguguuca 20

<210> SEQ ID NO 226
<211> LENGTH: 20
<212> TYPE: RNA
<213> ORGANISM: ARTIFICIAL SEQUENCE
<220> FEATURE:
<223> OTHER INFORMATION: SYNTHETIC

<400> SEQUENCE: 226
gcuaggaccc caguguucaa 20

<210> SEQ ID NO 227
<211> LENGTH: 20
<212> TYPE: RNA
<213> ORGANISM: ARTIFICIAL SEQUENCE
<220> FEATURE:
<223> OTHER INFORMATION: SYNTHETIC

<400> SEQUENCE: 227
cuaggacccc aguguucaaa 20

<210> SEQ ID NO 228
<211> LENGTH: 20
<212> TYPE: RNA
<213> ORGANISM: ARTIFICIAL SEQUENCE
<220> FEATURE:
<223> OTHER INFORMATION: SYNTHETIC

<400> SEQUENCE: 228
uaggacccca guguucaaaa 20

<210> SEQ ID NO 229
<211> LENGTH: 20
<212> TYPE: RNA
<213> ORGANISM: ARTIFICIAL SEQUENCE
<220> FEATURE:
<223> OTHER INFORMATION: SYNTHETIC

<400> SEQUENCE: 229
aggaccccag uguucaaaau 20

<210> SEQ ID NO 230
<211> LENGTH: 20
<212> TYPE: RNA
<213> ORGANISM: ARTIFICIAL SEQUENCE
<220> FEATURE:
<223> OTHER INFORMATION: SYNTHETIC

<400> SEQUENCE: 230
ggaccccagu guucaaaaua 20

<210> SEQ ID NO 231
<211> LENGTH: 20
<212> TYPE: RNA
<213> ORGANISM: ARTIFICIAL SEQUENCE
<220> FEATURE:
<223> OTHER INFORMATION: SYNTHETIC

<400> SEQUENCE: 231
gaccccagug uucaaaauaa 20

<210> SEQ ID NO 232
<211> LENGTH: 20
<212> TYPE: RNA
<213> ORGANISM: ARTIFICIAL SEQUENCE
<220> FEATURE:
<223> OTHER INFORMATION: SYNTHETIC

<400> SEQUENCE: 232
accccagugu ucaaaauaag 20

<210> SEQ ID NO 233
<211> LENGTH: 20
<212> TYPE: RNA
<213> ORGANISM: ARTIFICIAL SEQUENCE
<220> FEATURE:
<223> OTHER INFORMATION: SYNTHETIC

<400> SEQUENCE: 233
ccccaguguu caaaauaagu 20

<210> SEQ ID NO 234
<211> LENGTH: 20
<212> TYPE: RNA
<213> ORGANISM: ARTIFICIAL SEQUENCE
<220> FEATURE:
<223> OTHER INFORMATION: SYNTHETIC

<400> SEQUENCE: 234
cccaguguuc aaaauaaguu 20

<210> SEQ ID NO 235
<211> LENGTH: 20
<212> TYPE: RNA
<213> ORGANISM: ARTIFICIAL SEQUENCE
<220> FEATURE:

<223> OTHER INFORMATION: SYNTHETIC

<400> SEQUENCE: 235
ccaguguuca aaauaaguuu 20

<210> SEQ ID NO 236
<211> LENGTH: 20
<212> TYPE: RNA
<213> ORGANISM: ARTIFICIAL SEQUENCE
<220> FEATURE:
<223> OTHER INFORMATION: SYNTHETIC

<400> SEQUENCE: 236
caguguucaa aauaaguuug 20

<210> SEQ ID NO 237
<211> LENGTH: 20
<212> TYPE: RNA
<213> ORGANISM: ARTIFICIAL SEQUENCE
<220> FEATURE:
<223> OTHER INFORMATION: SYNTHETIC

<400> SEQUENCE: 237
aguguucaaa auaaguuugu 20

<210> SEQ ID NO 238
<211> LENGTH: 20
<212> TYPE: RNA
<213> ORGANISM: ARTIFICIAL SEQUENCE
<220> FEATURE:
<223> OTHER INFORMATION: SYNTHETIC

<400> SEQUENCE: 238
guguucaaaa uaaguuuguu 20

<210> SEQ ID NO 239
<211> LENGTH: 20
<212> TYPE: RNA
<213> ORGANISM: ARTIFICIAL SEQUENCE
<220> FEATURE:
<223> OTHER INFORMATION: SYNTHETIC

<400> SEQUENCE: 239
uguucaaaau aaguuuguuu 20

<210> SEQ ID NO 240
<211> LENGTH: 20
<212> TYPE: RNA
<213> ORGANISM: ARTIFICIAL SEQUENCE
<220> FEATURE:
<223> OTHER INFORMATION: SYNTHETIC

<400> SEQUENCE: 240
guucaaaaua aguuuguuuu 20

<210> SEQ ID NO 241
<211> LENGTH: 20
<212> TYPE: RNA
<213> ORGANISM: ARTIFICIAL SEQUENCE
<220> FEATURE:
<223> OTHER INFORMATION: SYNTHETIC

<400> SEQUENCE: 241
uucaaaauaa guuuguuuug 20

<210> SEQ ID NO 242
<211> LENGTH: 20
<212> TYPE: RNA
<213> ORGANISM: ARTIFICIAL SEQUENCE
<220> FEATURE:
<223> OTHER INFORMATION: SYNTHETIC

<400> SEQUENCE: 242
ucaaaauaag uuuguuuugc 20

<210> SEQ ID NO 243
<211> LENGTH: 20
<212> TYPE: RNA
<213> ORGANISM: ARTIFICIAL SEQUENCE
<220> FEATURE:
<223> OTHER INFORMATION: SYNTHETIC

<400> SEQUENCE: 243
caaaauaagu uuguuuugcu 20

<210> SEQ ID NO 244
<211> LENGTH: 20
<212> TYPE: RNA
<213> ORGANISM: ARTIFICIAL SEQUENCE
<220> FEATURE:
<223> OTHER INFORMATION: SYNTHETIC

<400> SEQUENCE: 244
aaaauaaguu uguuuugcuu 20

<210> SEQ ID NO 245
<211> LENGTH: 20
<212> TYPE: RNA
<213> ORGANISM: ARTIFICIAL SEQUENCE
<220> FEATURE:
<223> OTHER INFORMATION: SYNTHETIC

<400> SEQUENCE: 245
aaauaaguuu guuuugcuug 20

<210> SEQ ID NO 246
<211> LENGTH: 20
<212> TYPE: RNA
<213> ORGANISM: ARTIFICIAL SEQUENCE
<220> FEATURE:
<223> OTHER INFORMATION: SYNTHETIC

<400> SEQUENCE: 246
aauaaguuug uuuugcuugu 20

<210> SEQ ID NO 247
<211> LENGTH: 20
<212> TYPE: RNA
<213> ORGANISM: ARTIFICIAL SEQUENCE
<220> FEATURE:
<223> OTHER INFORMATION: SYNTHETIC

<400> SEQUENCE: 247
auaaguuugu uuugcuugug 20

<210> SEQ ID NO 248
<211> LENGTH: 20
<212> TYPE: RNA
<213> ORGANISM: ARTIFICIAL SEQUENCE
<220> FEATURE:
<223> OTHER INFORMATION: SYNTHETIC

<400> SEQUENCE: 248
uaaguuuguu uugcuuguga 20

<210> SEQ ID NO 249
<211> LENGTH: 20
<212> TYPE: RNA
<213> ORGANISM: ARTIFICIAL SEQUENCE
<220> FEATURE:
<223> OTHER INFORMATION: SYNTHETIC

<400> SEQUENCE: 249
aaguuuguuu ugcuugugag 20

<210> SEQ ID NO 250
<211> LENGTH: 20
<212> TYPE: RNA
<213> ORGANISM: ARTIFICIAL SEQUENCE
<220> FEATURE:
<223> OTHER INFORMATION: SYNTHETIC

<400> SEQUENCE: 250
aguuuguuuu gcuugugagc 20

<210> SEQ ID NO 251
<211> LENGTH: 20
<212> TYPE: RNA
<213> ORGANISM: ARTIFICIAL SEQUENCE
<220> FEATURE:
<223> OTHER INFORMATION: SYNTHETIC

<400> SEQUENCE: 251
guuuguuuug cuugugagcu 20

<210> SEQ ID NO 252
<211> LENGTH: 20
<212> TYPE: RNA
<213> ORGANISM: ARTIFICIAL SEQUENCE
<220> FEATURE:
<223> OTHER INFORMATION: SYNTHETIC

<400> SEQUENCE: 252
uuuguuuugc uugugagcuc 20

<210> SEQ ID NO 253
<211> LENGTH: 20
<212> TYPE: RNA
<213> ORGANISM: ARTIFICIAL SEQUENCE
<220> FEATURE:
<223> OTHER INFORMATION: SYNTHETIC

<400> SEQUENCE: 253
uuguuuugcu ugugagcucu 20

<210> SEQ ID NO 254
<211> LENGTH: 20
<212> TYPE: RNA
<213> ORGANISM: ARTIFICIAL SEQUENCE
<220> FEATURE:
<223> OTHER INFORMATION: SYNTHETIC

<400> SEQUENCE: 254
uguuuugcuu gugagcucua 20

<210> SEQ ID NO 255
<211> LENGTH: 20

<212> TYPE: RNA
<213> ORGANISM: ARTIFICIAL SEQUENCE
<220> FEATURE:
<223> OTHER INFORMATION: SYNTHETIC

<400> SEQUENCE: 255
guuuugcuug ugagcucuac 20

<210> SEQ ID NO 256
<211> LENGTH: 20
<212> TYPE: RNA
<213> ORGANISM: ARTIFICIAL SEQUENCE
<220> FEATURE:
<223> OTHER INFORMATION: SYNTHETIC

<400> SEQUENCE: 256
uuuugcuugu gagcucuaca 20

<210> SEQ ID NO 257
<211> LENGTH: 20
<212> TYPE: RNA
<213> ORGANISM: ARTIFICIAL SEQUENCE
<220> FEATURE:
<223> OTHER INFORMATION: SYNTHETIC

<400> SEQUENCE: 257
uuugcuugug agcucuacac 20

<210> SEQ ID NO 258
<211> LENGTH: 20
<212> TYPE: RNA
<213> ORGANISM: ARTIFICIAL SEQUENCE
<220> FEATURE:
<223> OTHER INFORMATION: SYNTHETIC

<400> SEQUENCE: 258
uugcuuguga gcucuacaca 20

<210> SEQ ID NO 259
<211> LENGTH: 20
<212> TYPE: RNA
<213> ORGANISM: ARTIFICIAL SEQUENCE
<220> FEATURE:
<223> OTHER INFORMATION: SYNTHETIC

<400> SEQUENCE: 259
ugcuugugag cucuacacaa 20

<210> SEQ ID NO 260
<211> LENGTH: 20
<212> TYPE: RNA
<213> ORGANISM: ARTIFICIAL SEQUENCE
<220> FEATURE:
<223> OTHER INFORMATION: SYNTHETIC

<400> SEQUENCE: 260
gcuugugagc ucuacacaaa 20

<210> SEQ ID NO 261
<211> LENGTH: 20
<212> TYPE: RNA
<213> ORGANISM: ARTIFICIAL SEQUENCE
<220> FEATURE:
<223> OTHER INFORMATION: SYNTHETIC

<400> SEQUENCE: 261
cuugugagcu cuacacaaac 20

<210> SEQ ID NO 262
<211> LENGTH: 20
<212> TYPE: RNA
<213> ORGANISM: ARTIFICIAL SEQUENCE
<220> FEATURE:
<223> OTHER INFORMATION: SYNTHETIC

<400> SEQUENCE: 262
uugugagcuc uacacaaacc 20

<210> SEQ ID NO 263
<211> LENGTH: 20
<212> TYPE: RNA
<213> ORGANISM: ARTIFICIAL SEQUENCE
<220> FEATURE:
<223> OTHER INFORMATION: SYNTHETIC

<400> SEQUENCE: 263
ugugagcucu acacaaaccg 20

<210> SEQ ID NO 264
<211> LENGTH: 20
<212> TYPE: RNA
<213> ORGANISM: ARTIFICIAL SEQUENCE
<220> FEATURE:
<223> OTHER INFORMATION: SYNTHETIC

<400> SEQUENCE: 264
gugagcucua cacaaaccgu 20

<210> SEQ ID NO 265
<211> LENGTH: 20
<212> TYPE: RNA
<213> ORGANISM: ARTIFICIAL SEQUENCE
<220> FEATURE:
<223> OTHER INFORMATION: SYNTHETIC

<400> SEQUENCE: 265
ugagcucuac acaaaccgug 20

<210> SEQ ID NO 266
<211> LENGTH: 20
<212> TYPE: RNA
<213> ORGANISM: ARTIFICIAL SEQUENCE
<220> FEATURE:
<223> OTHER INFORMATION: SYNTHETIC

<400> SEQUENCE: 266
gagcucuaca caaaccgugg 20

<210> SEQ ID NO 267
<211> LENGTH: 20
<212> TYPE: RNA
<213> ORGANISM: ARTIFICIAL SEQUENCE
<220> FEATURE:
<223> OTHER INFORMATION: SYNTHETIC

<400> SEQUENCE: 267
agcucuacac aaaccguggg 20

<210> SEQ ID NO 268
<211> LENGTH: 20
<212> TYPE: RNA
<213> ORGANISM: ARTIFICIAL SEQUENCE

<220> FEATURE:
<223> OTHER INFORMATION: SYNTHETIC

<400> SEQUENCE: 268
gcucuacaca aaccgugggu 20

<210> SEQ ID NO 269
<211> LENGTH: 20
<212> TYPE: RNA
<213> ORGANISM: ARTIFICIAL SEQUENCE
<220> FEATURE:
<223> OTHER INFORMATION: SYNTHETIC

<400> SEQUENCE: 269
cucuacacaa accgugggug 20

<210> SEQ ID NO 270
<211> LENGTH: 20
<212> TYPE: RNA
<213> ORGANISM: ARTIFICIAL SEQUENCE
<220> FEATURE:
<223> OTHER INFORMATION: SYNTHETIC

<400> SEQUENCE: 270
ucuacacaaa ccgugggugg 20

<210> SEQ ID NO 271
<211> LENGTH: 20
<212> TYPE: RNA
<213> ORGANISM: ARTIFICIAL SEQUENCE
<220> FEATURE:
<223> OTHER INFORMATION: SYNTHETIC

<400> SEQUENCE: 271
cuacacaaac cgugggugga 20

<210> SEQ ID NO 272
<211> LENGTH: 20
<212> TYPE: RNA
<213> ORGANISM: ARTIFICIAL SEQUENCE
<220> FEATURE:
<223> OTHER INFORMATION: SYNTHETIC

<400> SEQUENCE: 272
uacacaaacc guggguggaa 20

<210> SEQ ID NO 273
<211> LENGTH: 20
<212> TYPE: RNA
<213> ORGANISM: ARTIFICIAL SEQUENCE
<220> FEATURE:
<223> OTHER INFORMATION: SYNTHETIC

<400> SEQUENCE: 273
acacaaaccg uggguggaag 20

<210> SEQ ID NO 274
<211> LENGTH: 20
<212> TYPE: RNA
<213> ORGANISM: ARTIFICIAL SEQUENCE
<220> FEATURE:
<223> OTHER INFORMATION: SYNTHETIC

<400> SEQUENCE: 274
cacaaaccgu ggguggaagg 20

<210> SEQ ID NO 275
<211> LENGTH: 20
<212> TYPE: RNA
<213> ORGANISM: ARTIFICIAL SEQUENCE
<220> FEATURE:
<223> OTHER INFORMATION: SYNTHETIC

<400> SEQUENCE: 275
acaaaccgug gguggaaggg 20

<210> SEQ ID NO 276
<211> LENGTH: 20
<212> TYPE: RNA
<213> ORGANISM: ARTIFICIAL SEQUENCE
<220> FEATURE:
<223> OTHER INFORMATION: SYNTHETIC

<400> SEQUENCE: 276
caaaccgugg guggaagggg 20

<210> SEQ ID NO 277
<211> LENGTH: 20
<212> TYPE: RNA
<213> ORGANISM: ARTIFICIAL SEQUENCE
<220> FEATURE:
<223> OTHER INFORMATION: SYNTHETIC

<400> SEQUENCE: 277
aaaccguggg uggaaggggg 20

<210> SEQ ID NO 278
<211> LENGTH: 20
<212> TYPE: RNA
<213> ORGANISM: ARTIFICIAL SEQUENCE
<220> FEATURE:
<223> OTHER INFORMATION: SYNTHETIC

<400> SEQUENCE: 278
aaccgugggu ggaagggggu 20

<210> SEQ ID NO 279
<211> LENGTH: 20
<212> TYPE: RNA
<213> ORGANISM: ARTIFICIAL SEQUENCE
<220> FEATURE:
<223> OTHER INFORMATION: SYNTHETIC

<400> SEQUENCE: 279
accgugggug gaagggggua 20

<210> SEQ ID NO 280
<211> LENGTH: 20
<212> TYPE: RNA
<213> ORGANISM: ARTIFICIAL SEQUENCE
<220> FEATURE:
<223> OTHER INFORMATION: SYNTHETIC

<400> SEQUENCE: 280
ccgugggugg aaggggguaa 20

<210> SEQ ID NO 281
<211> LENGTH: 20
<212> TYPE: RNA
<213> ORGANISM: ARTIFICIAL SEQUENCE
<220> FEATURE:
<223> OTHER INFORMATION: SYNTHETIC

<400> SEQUENCE: 281 cguggugga aggggguaaa 20

<210> SEQ ID NO 282
<211> LENGTH: 20
<212> TYPE: RNA
<213> ORGANISM: ARTIFICIAL SEQUENCE
<220> FEATURE:
<223> OTHER INFORMATION: SYNTHETIC

<400> SEQUENCE: 282 gugggugga gggggguaaag 20

<210> SEQ ID NO 283
<211> LENGTH: 20
<212> TYPE: RNA
<213> ORGANISM: ARTIFICIAL SEQUENCE
<220> FEATURE:
<223> OTHER INFORMATION: SYNTHETIC

<400> SEQUENCE: 283
uggguggaag ggggua aagg 20

<210> SEQ ID NO 284
<211> LENGTH: 20
<212> TYPE: RNA
<213> ORGANISM: ARTIFICIAL SEQUENCE
<220> FEATURE:
<223> OTHER INFORMATION: SYNTHETIC

<400> SEQUENCE: 284
ggguggaagg ggguaaaggg 20

<210> SEQ ID NO 285
<211> LENGTH: 20
<212> TYPE: RNA
<213> ORGANISM: ARTIFICIAL SEQUENCE
<220> FEATURE:
<223> OTHER INFORMATION: SYNTHETIC

<400> SEQUENCE: 285
gguggaaggg gguaaaggga 20

<210> SEQ ID NO 286
<211> LENGTH: 20
<212> TYPE: RNA
<213> ORGANISM: ARTIFICIAL SEQUENCE
<220> FEATURE:
<223> OTHER INFORMATION: SYNTHETIC

<400> SEQUENCE: 286
guggaagggg guaaagggau 20

<210> SEQ ID NO 287
<211> LENGTH: 20
<212> TYPE: RNA
<213> ORGANISM: ARTIFICIAL SEQUENCE
<220> FEATURE:
<223> OTHER INFORMATION: SYNTHETIC

<400> SEQUENCE: 287
uggaaggggg uaaagggauc 20

<210> SEQ ID NO 288

<211> LENGTH: 20
<212> TYPE: RNA
<213> ORGANISM: ARTIFICIAL SEQUENCE
<220> FEATURE:
<223> OTHER INFORMATION: SYNTHETIC

<400> SEQUENCE: 288
ggaagggggu aaagggauca 20

<210> SEQ ID NO 289
<211> LENGTH: 20
<212> TYPE: RNA
<213> ORGANISM: ARTIFICIAL SEQUENCE
<220> FEATURE:
<223> OTHER INFORMATION: SYNTHETIC

<400> SEQUENCE: 289
gaaggggdua aagggaucag 20

<210> SEQ ID NO 290
<211> LENGTH: 20
<212> TYPE: RNA
<213> ORGANISM: ARTIFICIAL SEQUENCE
<220> FEATURE:
<223> OTHER INFORMATION: SYNTHETIC

<400> SEQUENCE: 290 aagggggua agggaucagg 20

<210> SEQ ID NO 291
<211> LENGTH: 20
<212> TYPE: RNA
<213> ORGANISM: ARTIFICIAL SEQUENCE
<220> FEATURE:
<223> OTHER INFORMATION: SYNTHETIC

<400> SEQUENCE: 291
agggggdaaa gggaucaggu 20

<210> SEQ ID NO 292
<211> LENGTH: 20
<212> TYPE: RNA
<213> ORGANISM: ARTIFICIAL SEQUENCE
<220> FEATURE:
<223> OTHER INFORMATION: SYNTHETIC

<400> SEQUENCE: 292 gggggaaag ggaucagguu 20

<210> SEQ ID NO 293
<211> LENGTH: 20
<212> TYPE: RNA
<213> ORGANISM: ARTIFICIAL SEQUENCE
<220> FEATURE:
<223> OTHER INFORMATION: SYNTHETIC

<400> SEQUENCE: 293
ggggdaaagg gaucagguuu 20

<210> SEQ ID NO 294
<211> LENGTH: 20
<212> TYPE: RNA
<213> ORGANISM: ARTIFICIAL SEQUENCE
<220> FEATURE:
<223> OTHER INFORMATION: SYNTHETIC

<400> SEQUENCE: 294
ggguaaaggg aucagguuuu 20

<210> SEQ ID NO 295
<211> LENGTH: 20
<212> TYPE: RNA
<213> ORGANISM: ARTIFICIAL SEQUENCE
<220> FEATURE:
<223> OTHER INFORMATION: SYNTHETIC

<400> SEQUENCE: 295
gguaaaggga ucagguuuuc 20

<210> SEQ ID NO 296
<211> LENGTH: 20
<212> TYPE: RNA
<213> ORGANISM: ARTIFICIAL SEQUENCE
<220> FEATURE:
<223> OTHER INFORMATION: SYNTHETIC

<400> SEQUENCE: 296
guaaagggau cagguuuucu 20

<210> SEQ ID NO 297
<211> LENGTH: 20
<212> TYPE: RNA
<213> ORGANISM: ARTIFICIAL SEQUENCE
<220> FEATURE:
<223> OTHER INFORMATION: SYNTHETIC

<400> SEQUENCE: 297
uaaagggauc agguuuucua 20

<210> SEQ ID NO 298
<211> LENGTH: 20
<212> TYPE: RNA
<213> ORGANISM: ARTIFICIAL SEQUENCE
<220> FEATURE:
<223> OTHER INFORMATION: SYNTHETIC

<400> SEQUENCE: 298
aaagggauca gguuuucuac 20

<210> SEQ ID NO 299
<211> LENGTH: 20
<212> TYPE: RNA
<213> ORGANISM: ARTIFICIAL SEQUENCE
<220> FEATURE:
<223> OTHER INFORMATION: SYNTHETIC

<400> SEQUENCE: 299
aagggaucag guuuucuacu 20

<210> SEQ ID NO 300
<211> LENGTH: 20
<212> TYPE: RNA
<213> ORGANISM: ARTIFICIAL SEQUENCE
<220> FEATURE:
<223> OTHER INFORMATION: SYNTHETIC

<400> SEQUENCE: 300
agggaucagg uuuucuacua 20

<210> SEQ ID NO 301
<211> LENGTH: 20
<212> TYPE: RNA

<213> ORGANISM: ARTIFICIAL SEQUENCE
<220> FEATURE:
<223> OTHER INFORMATION: SYNTHETIC

<400> SEQUENCE: 301
gggaucaggu uuucuacuau 20

<210> SEQ ID NO 302
<211> LENGTH: 20
<212> TYPE: RNA
<213> ORGANISM: ARTIFICIAL SEQUENCE
<220> FEATURE:
<223> OTHER INFORMATION: SYNTHETIC

<400> SEQUENCE: 302
ggaucagguu uucuacuaug 20

<210> SEQ ID NO 303
<211> LENGTH: 20
<212> TYPE: RNA
<213> ORGANISM: ARTIFICIAL SEQUENCE
<220> FEATURE:
<223> OTHER INFORMATION: SYNTHETIC

<400> SEQUENCE: 303
gaucagguuu ucuacuaugu 20

<210> SEQ ID NO 304
<211> LENGTH: 20
<212> TYPE: RNA
<213> ORGANISM: ARTIFICIAL SEQUENCE
<220> FEATURE:
<223> OTHER INFORMATION: SYNTHETIC

<400> SEQUENCE: 304
aucagguuuu cuacuauguu 20

<210> SEQ ID NO 305
<211> LENGTH: 20
<212> TYPE: RNA
<213> ORGANISM: ARTIFICIAL SEQUENCE
<220> FEATURE:
<223> OTHER INFORMATION: SYNTHETIC

<400> SEQUENCE: 305
ucagguuuuc uacuauguuu 20

<210> SEQ ID NO 306
<211> LENGTH: 20
<212> TYPE: RNA
<213> ORGANISM: ARTIFICIAL SEQUENCE
<220> FEATURE:
<223> OTHER INFORMATION: SYNTHETIC

<400> SEQUENCE: 306
cagguuuucu acuauguuug 20

<210> SEQ ID NO 307
<211> LENGTH: 20
<212> TYPE: RNA
<213> ORGANISM: ARTIFICIAL SEQUENCE
<220> FEATURE:
<223> OTHER INFORMATION: SYNTHETIC

<400> SEQUENCE: 307
agguuuucua cuauguuugu 20

<210> SEQ ID NO 308
<211> LENGTH: 20
<212> TYPE: RNA
<213> ORGANISM: ARTIFICIAL SEQUENCE
<220> FEATURE:
<223> OTHER INFORMATION: SYNTHETIC

<400> SEQUENCE: 308
gguuuucuac uauguuuguc 20

<210> SEQ ID NO 309
<211> LENGTH: 20
<212> TYPE: RNA
<213> ORGANISM: ARTIFICIAL SEQUENCE
<220> FEATURE:
<223> OTHER INFORMATION: SYNTHETIC

<400> SEQUENCE: 309
guuuucuacu auguuugucc 20

<210> SEQ ID NO 310
<211> LENGTH: 20
<212> TYPE: RNA
<213> ORGANISM: ARTIFICIAL SEQUENCE
<220> FEATURE:
<223> OTHER INFORMATION: SYNTHETIC

<400> SEQUENCE: 310
uuuucuacua uguuuguccc 20

<210> SEQ ID NO 311
<211> LENGTH: 20
<212> TYPE: RNA
<213> ORGANISM: ARTIFICIAL SEQUENCE
<220> FEATURE:
<223> OTHER INFORMATION: SYNTHETIC

<400> SEQUENCE: 311
uuucuacuau guuugucccg 20

<210> SEQ ID NO 312
<211> LENGTH: 20
<212> TYPE: RNA
<213> ORGANISM: ARTIFICIAL SEQUENCE
<220> FEATURE:
<223> OTHER INFORMATION: SYNTHETIC

<400> SEQUENCE: 312
uucuacuaug uuugucccgu 20

<210> SEQ ID NO 313
<211> LENGTH: 20
<212> TYPE: RNA
<213> ORGANISM: ARTIFICIAL SEQUENCE
<220> FEATURE:
<223> OTHER INFORMATION: SYNTHETIC

<400> SEQUENCE: 313
ucuacuaugu uugucccgug 20

<210> SEQ ID NO 314
<211> LENGTH: 20
<212> TYPE: RNA
<213> ORGANISM: ARTIFICIAL SEQUENCE
<220> FEATURE:

<223> OTHER INFORMATION: SYNTHETIC

<400> SEQUENCE: 314
cuacuauguu ugucccgugg 20

<210> SEQ ID NO 315
<211> LENGTH: 20
<212> TYPE: RNA
<213> ORGANISM: ARTIFICIAL SEQUENCE
<220> FEATURE:
<223> OTHER INFORMATION: SYNTHETIC

<400> SEQUENCE: 315
uacuauguuu gucccguggu 20

<210> SEQ ID NO 316
<211> LENGTH: 20
<212> TYPE: RNA
<213> ORGANISM: ARTIFICIAL SEQUENCE
<220> FEATURE:
<223> OTHER INFORMATION: SYNTHETIC

<400> SEQUENCE: 316
acuauguuug ucccguggug 20

<210> SEQ ID NO 317
<211> LENGTH: 20
<212> TYPE: RNA
<213> ORGANISM: ARTIFICIAL SEQUENCE
<220> FEATURE:
<223> OTHER INFORMATION: SYNTHETIC

<400> SEQUENCE: 317
cuauguuugu cccgugguga 20

<210> SEQ ID NO 318
<211> LENGTH: 20
<212> TYPE: RNA
<213> ORGANISM: ARTIFICIAL SEQUENCE
<220> FEATURE:
<223> OTHER INFORMATION: SYNTHETIC

<400> SEQUENCE: 318
uauguuuguc ccguggugau 20

<210> SEQ ID NO 319
<211> LENGTH: 20
<212> TYPE: RNA
<213> ORGANISM: ARTIFICIAL SEQUENCE
<220> FEATURE:
<223> OTHER INFORMATION: SYNTHETIC

<400> SEQUENCE: 319
auguuugucc cguggugaug 20

<210> SEQ ID NO 320
<211> LENGTH: 20
<212> TYPE: RNA
<213> ORGANISM: ARTIFICIAL SEQUENCE
<220> FEATURE:
<223> OTHER INFORMATION: SYNTHETIC

<400> SEQUENCE: 320
uguuuguccc guggugaugg 20

<210> SEQ ID NO 321
<211> LENGTH: 20
<212> TYPE: RNA
<213> ORGANISM: ARTIFICIAL SEQUENCE
<220> FEATURE:
<223> OTHER INFORMATION: SYNTHETIC

<400> SEQUENCE: 321
guuugucccg uggugaugga 20

<210> SEQ ID NO 322
<211> LENGTH: 20
<212> TYPE: RNA
<213> ORGANISM: ARTIFICIAL SEQUENCE
<220> FEATURE:
<223> OTHER INFORMATION: SYNTHETIC

<400> SEQUENCE: 322
uuugucccgu ggugauggac 20

<210> SEQ ID NO 323
<211> LENGTH: 20
<212> TYPE: RNA
<213> ORGANISM: ARTIFICIAL SEQUENCE
<220> FEATURE:
<223> OTHER INFORMATION: SYNTHETIC

<400> SEQUENCE: 323
uugucccgug gugauggacu 20

<210> SEQ ID NO 324
<211> LENGTH: 20
<212> TYPE: RNA
<213> ORGANISM: ARTIFICIAL SEQUENCE
<220> FEATURE:
<223> OTHER INFORMATION: SYNTHETIC

<400> SEQUENCE: 324
ugucccgugg ugauggacug 20

<210> SEQ ID NO 325
<211> LENGTH: 20
<212> TYPE: RNA
<213> ORGANISM: ARTIFICIAL SEQUENCE
<220> FEATURE:
<223> OTHER INFORMATION: SYNTHETIC

<400> SEQUENCE: 325
gucccguggu gauggacugg 20

<210> SEQ ID NO 326
<211> LENGTH: 20
<212> TYPE: RNA
<213> ORGANISM: ARTIFICIAL SEQUENCE
<220> FEATURE:
<223> OTHER INFORMATION: SYNTHETIC

<400> SEQUENCE: 326
ucccguggug auggacuggg 20

<210> SEQ ID NO 327
<211> LENGTH: 20
<212> TYPE: RNA
<213> ORGANISM: ARTIFICIAL SEQUENCE
<220> FEATURE:
<223> OTHER INFORMATION: SYNTHETIC

<400> SEQUENCE: 327
cccgugguga uggacuggga 20

<210> SEQ ID NO 328
<211> LENGTH: 20
<212> TYPE: RNA
<213> ORGANISM: ARTIFICIAL SEQUENCE
<220> FEATURE:
<223> OTHER INFORMATION: SYNTHETIC

<400> SEQUENCE: 328
ccguggugau ggacugggac 20

<210> SEQ ID NO 329
<211> LENGTH: 20
<212> TYPE: RNA
<213> ORGANISM: ARTIFICIAL SEQUENCE
<220> FEATURE:
<223> OTHER INFORMATION: SYNTHETIC

<400> SEQUENCE: 329
cguggugaug gacugggaca 20

<210> SEQ ID NO 330
<211> LENGTH: 20
<212> TYPE: RNA
<213> ORGANISM: ARTIFICIAL SEQUENCE
<220> FEATURE:
<223> OTHER INFORMATION: SYNTHETIC

<400> SEQUENCE: 330
guggugaugg acugggacag 20

<210> SEQ ID NO 331
<211> LENGTH: 20
<212> TYPE: RNA
<213> ORGANISM: ARTIFICIAL SEQUENCE
<220> FEATURE:
<223> OTHER INFORMATION: SYNTHETIC

<400> SEQUENCE: 331
uggugaugga cugggacagg 20

<210> SEQ ID NO 332
<211> LENGTH: 20
<212> TYPE: RNA
<213> ORGANISM: ARTIFICIAL SEQUENCE
<220> FEATURE:
<223> OTHER INFORMATION: SYNTHETIC

<400> SEQUENCE: 332
ggugauggac ugggacagga 20

<210> SEQ ID NO 333
<211> LENGTH: 20
<212> TYPE: RNA
<213> ORGANISM: ARTIFICIAL SEQUENCE
<220> FEATURE:
<223> OTHER INFORMATION: SYNTHETIC

<400> SEQUENCE: 333
gugauggacu gggacaggag 20

<210> SEQ ID NO 334
<211> LENGTH: 20

<212> TYPE: RNA
<213> ORGANISM: ARTIFICIAL SEQUENCE
<220> FEATURE:
<223> OTHER INFORMATION: SYNTHETIC

<400> SEQUENCE: 334
ugauggacug ggacaggagc 20

<210> SEQ ID NO 335
<211> LENGTH: 20
<212> TYPE: RNA
<213> ORGANISM: ARTIFICIAL SEQUENCE
<220> FEATURE:
<223> OTHER INFORMATION: SYNTHETIC

<400> SEQUENCE: 335
gauggacugg gacaggagcu 20

<210> SEQ ID NO 336
<211> LENGTH: 20
<212> TYPE: RNA
<213> ORGANISM: ARTIFICIAL SEQUENCE
<220> FEATURE:
<223> OTHER INFORMATION: SYNTHETIC

<400> SEQUENCE: 336
auggacuggg acaggagcua 20

<210> SEQ ID NO 337
<211> LENGTH: 20
<212> TYPE: RNA
<213> ORGANISM: ARTIFICIAL SEQUENCE
<220> FEATURE:
<223> OTHER INFORMATION: SYNTHETIC

<400> SEQUENCE: 337
uggacuggga caggagcuaa 20

<210> SEQ ID NO 338
<211> LENGTH: 18
<212> TYPE: DNA
<213> ORGANISM: ARTIFICIAL SEQUENCE
<220> FEATURE:
<223> OTHER INFORMATION: SYNTHETIC

<400> SEQUENCE: 338
tcagaactca cctgttag 18

<210> SEQ ID NO 339
<211> LENGTH: 18
<212> TYPE: RNA
<213> ORGANISM: ARTIFICIAL SEQUENCE
<220> FEATURE:
<223> OTHER INFORMATION: SYNTHETIC

<400> SEQUENCE: 339
cuaacaggug aguucuga 18

<210> SEQ ID NO 340
<211> LENGTH: 15
<212> TYPE: DNA
<213> ORGANISM: ARTIFICIAL SEQUENCE
<220> FEATURE:
<223> OTHER INFORMATION: SYNTHETIC

<400> SEQUENCE: 340

-continued

```
ttcgccgtgt ccgat                                               15


<210> SEQ ID NO 341
<211> LENGTH: 79
<212> TYPE: RNA
<213> ORGANISM: ARTIFICIAL SEQUENCE
<220> FEATURE:
<223> OTHER INFORMATION: SYNTHETIC

<400> SEQUENCE: 341

gacgcgaccg aauggugaag gacgggucca gugcuucggc acuguugagu agagugugag     60

cuccguaacu ggucgcguc                                                  79


<210> SEQ ID NO 342
<211> LENGTH: 35
<212> TYPE: DNA
<213> ORGANISM: ARTIFICIAL SEQUENCE
<220> FEATURE:
<223> OTHER INFORMATION: SYNTHETIC

<400> SEQUENCE: 342

tcagaactca ggctagctac aacgactgtt agttc                                35
```

RNA ARRAY COMPOSITIONS AND METHODS

CROSS-REFERENCE TO RELATED APPLICATIONS

This patent application is divisional of U.S. application Ser. No. 14/073,350 filed on Nov. 6, 2013, which claims priority to U.S. provisional Application No. 61/723,011 filed on Nov. 6, 2012. Each of these applications is incorporated by reference herein in its entirety.

STATEMENT REGARDING FEDERALLY SPONSORED RESEARCH OR DEVELOPMENT

This invention was made with government support under DK093467 and HG004952 awarded by the National Institutes of Health. The government has certain rights in the invention.

BACKGROUND

High density DNA microarrays have been commercially available worldwide for more than a decade, but high density RNA microarrays do not exist yet due to the difficulty of equivalent high density RNA synthesis methods. The development of RNA arrays, and especially high density RNA arrays would enable a number important new applications including, for example, fabrication of RNA aptamer arrays; identification of RNA sequences that produce fluorescence from non-fluorescent small molecules; identification and characterization of novel ribozymes and RNA-binding proteins. Thus, there is an ongoing need for high density RNA arrays and methods for generating them.

BRIEF SUMMARY

Described herein are RNA and template array compositions and methods for generating such compositions. The methods and compositions are based on the finding that DNA arrays can serve as a template for RNA-polymerase-based synthesis of complementary RNA arrays.

Accordingly, in one aspect described herein is an RNA array comprising RNAs that are covalently linked at their 5' ends to a solid support.

In some embodiments, the covalently linked RNAs represent at least 10 unique RNA sequences and have a feature density of at least 20 features/cm$^2$.

In some embodiments the RNAs comprise at least about 20 unique RNA sequences. In other embodiments the RNAs represent at least about 50 unique RNA sequences.

In some embodiments the length of the at least ten unique RNA sequences is about 20 bases to about 50 bases. In some embodiments the density of single-stranded RNAs in the RNA array is about 200 features/cm$^2$.

In some embodiments the RNAs in the RNA array comprise modified ribonucleotides. In one embodiment the modified ribonucleotides are RNase resistant (e.g., 2'-fluoro ribonucleotides or 2'-methoxyribonucleotides).

In another aspect provided herein is a template array comprising: (i) an array of single-stranded template DNA oligonucleotides linked at their 3' ends to a solid support, comprising a consensus sequence, and capped by a protecting group at their 5' ends; and (ii) single-stranded RNA primers that are covalently linked at their 5' ends to the solid support, and that are complementary to the consensus sequence, wherein the single-stranded RNA primers hybridize to the single-stranded template DNA oligonucleotides.

In some embodiments the single-stranded RNA primers have a length of about 4 bases to about 20 bases. In one embodiment, the single-stranded RNA primers have a length of about 13 bases.

In some embodiments the single-stranded template DNA oligonucleotides or single-stranded RNA primers are covalently linked to the solid support through a polyethylene glycol spacer.

In some embodiments the protecting group to be added to the 5' end of the single-stranded template DNA oligonucleotides is an acetyl group or a phenoxyacetyl group.

In some embodiments a kit is provided that includes the above-mentioned template array and any of (i) an RNA polymerase; (ii) ribonucleoside triphosphates; and (iii) a DNase. In some embodiments the ribonucleoside triphosphates to be included in the kit are modified ribonucleoside triphosphates. In some embodiments, the included modified ribonucleoside triphosphates are modified ribonucleosides (e.g., 2'-fluoro ribonucleosides, 2'-methoxy ribonucleosides, 2'-amino ribonucleosides, 5-bromouridine-5'-triphosphate, 4-thiouridine-5'-triphosphate, 6-thioguanosine-5'-triphosphate).

In a further aspect disclosed herein is a method for generating a template array, which includes the steps of: (i) providing a solid support comprising a layer of protected deoxyribonucleosides that comprise a 5'-photolabile protecting group and are covalently linked at their 3' end to a spacer layer bound to the solid support; (ii) irradiating the layer of protected deoxyribonucleosides with ultraviolet energy sufficient to deprotect about half of the protected deoxyribonucleosides; (iii) coupling the deprotected deoxyribonucleosides with a ribonucleoside phosphoramidite comprising a 5' acid-labile protecting group; (iv) irradiating the remaining protected deoxyribonucleosides with ultraviolet irradiation sufficient to deprotect all of the remaining protected deoxyribonucleoside phosphoramidites; (v) extending the deprotected deoxyribonucleosides, at one or more locations, by light-directed 3' to 5' photolithographic synthesis to generate template DNA oligonucleotides;

(vi) coupling a protecting group to the 5' ends of the template DNA oligonucleotides;

(vii) removing the 5' acid-labile protecting groups on the protected ribonucleosides by acid treatment; and (viii) extending the deprotected ribonucleosides, at one or more locations, by 5' to 3' chemical synthesis of RNA primers comprising a sequence that is complementary to a sequence at the 3' end of the template DNA strands to obtain a template array.

In some embodiments of the above-mentioned method, the 5' acid-labile protecting group in step (iii) includes a 4,4'-dimethoxytrityl (DMT) group.

In some embodiments the protecting group coupled to the 5'-ends of the template DNA strands in step (vi) is a phenoxyacetyl group or an acetyl group.

In some embodiments RNase-resistant modified ribonucleoside phosphoramidites are used in the extension of the deprotected ribonucleosides to obtain RNase-resistant RNA primers in step (viii). In some embodiments, where RNase-resistant modified ribonucleoside phosphoramidites are used, the RNase-resistant modified ribonucleoside phosphoramidites are 2'-fluoro ribonucleoside phosphoramidites or 2'-methoxy ribonucleoside phosphoramidites.

In a further aspect described herein is a method for generating an RNA array, comprising the steps of (i) providing a template array of (a) single-stranded template DNAs linked at their 3' ends to a solid support and comprising a consensus sequence; and (b) single-stranded RNA primers that are covalently linked at their 5' ends to the solid support, and that are complementary to the consensus sequence of the single-stranded template DNAs; (ii) hybridizing the single-stranded RNA primers with the single-stranded template DNAs; (iii) extending the hybridized RNA primers along the single-stranded template DNAs using an RNA polymerase and ribonucleoside triphosphates to obtain double-stranded DNA-RNA hybrids; and (iv) exposing the DNA-RNA hybrids to a DNase enzyme to remove the template DNAs from the DNA-RNA hybrids to obtain an RNA array.

In some embodiments the RNA polymerase in step (iii) is T7 RNA polymerase or T3 RNA polymerase.

In some embodiments the ribonucleoside triphosphates used in step (iii) are modified ribonucleoside triphosphates. In one embodiment, the modified ribonucleoside triphosphates are RNase-resistant modified ribonucleoside triphosphates. In some embodiments the RNase-resistant modified ribonucleoside triphosphates to be used are 2'-fluoro ribonucleoside triphosphates or 2'-methoxy ribonucleoside triphosphates.

In some embodiments the method can also include a step of synthesizing the single-stranded RNA primers in the array prior to step (i).

In some embodiments the single-stranded template DNAs represent at least 20 unique sequences. In other embodiments the single-stranded template DNAs represent at least 50 unique sequences.

In yet another aspect provided herein is a method to generate an RNA bead pool, comprising: (i) providing beads comprising 5'-linked RNA primers comprising a consensus sequence; (ii) hybridizing the 5'-linked RNA primers with DNA oligonucleotides comprising a unique template sequence and a sequence complementary to the consensus sequence, wherein the DNA oligonucleotides are provided in solution; (iii) extending the hybridized RNA primers along the single-stranded template DNAs using an RNA polymerase and ribonucleoside triphosphates to obtain double-stranded DNA-RNA hybrids; and contacting the DNA-RNA hybrids with a DNase to remove the template DNAs from the DNA-RNA hybrids to obtain an RNA bead pool.

INCORPORATION BY REFERENCE

All publications, patents, and patent applications mentioned in this specification are herein incorporated by reference to the same extent as if each individual publication, patent, and patent application was specifically and individually indicated to be incorporated by reference.

BRIEF DESCRIPTION OF THE DRAWINGS

The patent or application file contains at least one drawing executed in color. Copies of this patent or patent application publication with color drawing(s) will be provided by the Office upon request and payment of the necessary fee. The present invention will be better understood and features, aspects and advantages other than those set forth above will become apparent when consideration is given to the following detailed description thereof. Such detailed description makes reference to the following drawings, wherein.

DETAILED DESCRIPTION

Figure 1A:
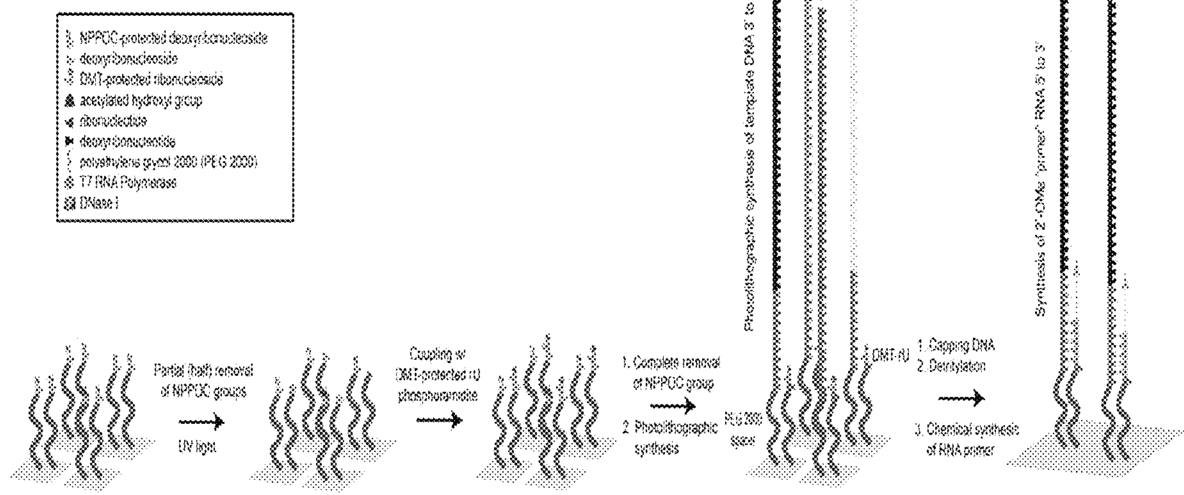
FIGS. 1A and 1B show a schematic overview of an exemplary embodiment of an RNA array synthesis method starting from a solid support coated with a PEG 2000 spacer layer linked to photolabile NPPOC-protected, deoxyribonucleosides at their 3' end. UV light irradiation is controlled so as to deprotect about half of the 3'-linked deoxyribonucleosides. The deprotected deoxyribonucleosides are then coupled to an acid-labile DMT-protected ribonucleoside phosphoramidite. UV light irradiation is then used to deprotect the remaining NPPOC-protected deoxyribonucleosides. Following this deprotection step, photolithographic 3' to 5' synthesis is used to generate an array of template DNA oligonucleotides, comprising an initial consensus sequence of approximately 12 bases that is common to most or all positions and a downstream sequence that is unique for each position or subsets of positions in the array. After template DNA oligonucleotide synthesis is completed, the DNA oligonucleotides are capped by acetylation at their 5' ends. The DMT-protected ribonucleoside phosphoramidites are then deprotected by acid treatment. Chemical synthesis, with 2-methoxy ribonucleoside phosphoramidites, is then used to generate a 5'-linked RNA primer comprising a sequence that is complementary to the template DNA consensus sequence mentioned above. Hybridization of the synthesized RNA primers with the consensus sequence in the template DNA oligonucleotides is then used to generate a cRNA copy of each unique template DNA oligonucleotide sequence using T7 RNA polymerase or in some cases, T3 RNA polymerase, in the presence of ribonucleoside triphosphates, or in some cases, RNase-resistant ribonucleoside triphosphates. After RNA polymerase synthesis of RNAs is complete, template DNA is eliminated from the array by digestion with DNase leaving behind an RNA array ready for use.

Described herein are RNA array compositions and methods for generating such compositions. The methods and compositions are based on the finding that DNA arrays, e.g., high density DNA arrays can serve as templates for RNA-polymerase-based synthesis of a complementary RNA array. Many possible applications for RNA arrays can be envisioned, including, but not limited to, deciphering the binding specificities of RNA-binding proteins, as a tool to aid in the engineering of sequence-specific RNA-binding proteins, for screening and characterizing RNA-based therapeutics, for fabricating tiling arrays of RNA viral genomes, for fabricating miRNA arrays, engineering ribozyme arrays, discovering new ribozymes, studying ribozyme function, engineering artificial siRNAs and miRNAs, fabricating mRNA tiling arrays, and searching for miRNA "sponges" (molecules that bind to and inactivate miRNAs).

It is to be understood that this invention is not limited to the particular methodology, protocols, materials, and reagents described, as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "an", and "the" include plural reference unless the context clearly dictates otherwise. As well, the terms "a" (or "an"), "one or more" and "at least one" can be used interchangeably herein. It is also to be noted that the terms "comprising", "including", and "having" can be used interchangeably.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods and materials are now described. All publications and patents specifically mentioned herein are incorporated by reference for all purposes including describing and disclosing the chemicals, cell lines, vectors, animals, instruments, statistical analysis and methodologies which are reported in the publications which might be used in connection with the invention. All references cited in this specification are to be taken as indicative of the level of skill in the art. Nothing herein is to be construed as an admission that the invention is not entitled to antedate such disclosure by virtue of prior invention.

The practice of the present invention will employ, unless otherwise indicated, conventional techniques of medicinal chemistry, pharmacology, organic chemistry, analytical chemistry, molecular biology, microbiology, and immunology, which are within the skill of the art. Such techniques are explained fully in the literature.

I. Definitions

In describing the embodiments and claiming the invention, the following terminology will be used in accordance with the definitions set out below.

As used herein, "about" means within 5% of a stated range within the relevant parameter.

As used herein, "RNase-resistant" refers to a modified RNA having reduction in susceptibility to RNase degradation or the ability of a modified ribonucleoside to confer a reduction in susceptibility of an RNA to RNase degradation by at least 10%.

II. Methods

Disclosed herein are methods for generating a template array and for generating RNA arrays using such template arrays.

In an exemplary embodiment, generating a template array starts from a solid support material such as amorphous carbon, glassy carbon, polymer or silanized glass that is coated with a layer of spacer material (e.g., PEG 2000 or PEG 4500) covalently linked to deoxyribonucleoside phosphoramidites ("bridging moieties") protected by a photolabile protecting group, e.g., 3'-nitrophenylpropyloxycarbonyl (NPPOC). In other embodiments, the solid support material is provided in the form of silica beads in the size range of 1 to 10 microns. The NPPOC-protected spacer layer is then irradiated with a suitable amount of deprotecting dose of UV light (e.g., 0.5 joule on amorphous carbon on gold, 0.75 joule on glassy carbon at about 365 nm in the working examples provided herein) to remove about half of the NPPOC protecting groups on the spacer layer, which deprotects hydroxyl groups on half of the deoxyribonucleosides covalently linked to the spacer layer. The deoxyribonucleosides with deprotected, free hydroxyl groups are then coupled with an acid-labile protecting group such as 4,4'-dimethoxytrityl (DMT)-protected ribonucleoside phosphoramidites. Afterwards, a full dose of UV light is used to remove all of the remaining photolabile protecting groups from the spacer layer, which allows the light-directed 3' to 5' photolithographic synthesis of DNA arrays starting from the newly deprotected deoxyribonucleoside phosphoramidites. Methods for 3' to 5' photolithographic synthesis of DNA oligonucleotide arrays are known in the art, as described in, e.g., Wu et al (2012), *Angewandte Chimie Int Ed Engl* 51(19):4628-4632. The initial 8 to about 15 deoxynucleotides (e.g., 9, 10, 11, 12, 13, or 14 deoxynucleotides) attained by photolithographic DNA synthesis encompass a "consensus" sequence that is common to the single-stranded template DNAs to be synthesized. For example, in one embodiment, the consensus sequence is 3'-CCTGTGCCGCTT-5 (SEQ ID NO:1). After 3' to 5' photolithographic synthesis of the consensus sequence, a variety of positionally-determined template sequences are synthesized in a desired pattern in the length range of about 20 deoxyribonucleotides to about 80 deoxyribonucleotides. After photolithographic synthesis of the template DNA strands, these are protected "capped" by a phenoxyacetyl group or an acetyl group at the 5' end to block undesired further synthesis. Finally, the acid-labile DMT protecting groups on the 5'-linked, protected ribonucleoside phosphoramidites are removed by acid treatment (e.g., with 2% trichloroacetic acid or 3% dichloroacetic acid in dichloromethane) to expose 3' hydroxyl groups of the 5'-linked ribonucleosides for chemical synthesis of an RNA primer complementary consensus sequence. The template array can be used to generate an RNA array, as described below.

In some embodiments, the spacer layer, deoxyribonucleoside or ribonucleoside is protected with an acid-labile protecting group, such as 4,4'-DMT rather than a photolabile protecting group. In this case, partial deprotection of the layer is achieved by treatment with a dilute solution of dichloro- or trichloroacetic acid, reduced exposure time to the acid, or both (e.g., with 2% trichloroacetic acid or 3% dichloroacetic acid in dichloromethane for 50 seconds or more). The deoxyribonucleosides with deprotected, free hydroxyl groups are then coupled with a photolabile protecting group such as NPPOC. Afterwards, a higher concentration of the deprotecting acid is used to remove all of the remaining acid-labile protecting groups from the spacer layer, which allows the light-directed 3' to 5' photolithographic synthesis of DNA arrays starting from the newly deprotected deoxyribonucleoside phosphoramidites. After photolithographic synthesis of the template DNA strands, these are protected "capped" by a phenoxyacetyl group or an acetyl group at the 5' end to block undesired further synthesis. Finally, the photolabile NPPOC protecting groups on the 5'-linked, protected ribonucleoside phosphoramidites are removed by irradiation with UV light to expose 3' hydroxyl groups of the 5'-linked ribonucleosides for chemical synthesis of an RNA primer complementary consensus sequence.

In some embodiments the length of the template DNA strands ranges from about 20 bases to about 80 bases, e.g., about 25 bases, 27 bases, 28 bases, 29 bases, 35 bases, 40 bases, 60 bases, 70 bases, or another length from about 20 bases to about 80 bases.

In some embodiments the template DNA strands to be synthesized can be synthesized to obtain a range of template DNA strand densities ranging from about 20 to about 1,000,000 features/cm$^2$, e.g., about 25, 30, 40, 50, 60, 65, 70, 75, 80, 100, 120, 150, 200, 300, 500, 750, 1,000, 2,000, 2,500, 3,000, 3,500, 3,750, 4,200, 4,500, 5,000, 6,000, 6,500, 7,000, 7,500, 8,000, 9,000, 20,000, 50,000, 100,000, 200,000, 400,000, 500,000, 600,000, 700,000, 800,000, 900, 000, or another feature density from about 20 features/cm$^2$ to about 1,000,000 features/cm$^2$.

In various embodiments the template DNA strands to be synthesized represent at least 20 unique sequences to about 1,000,000 unique sequences, e.g., 30, 50, 100, 130, 145, 148, 150, 155, 160, 200, 500, 1,000, 1,500, 2,000, 3,000, 5,000, 10,000, 15,000, 20,000, 50,000, 100,000, 200,000, 400,000, 500,000, 600,000, 700,000, 800,000, 900,000, or another number of unique sequences. In some embodiments the template DNA oligonucleotide sequences comprise a series of subsequences that are shifted relative to each other by a single terminal nucleotide, where the template DNA oligonucleotide sequences, in aggregate, cover a longer contiguous sequence, e.g., a genomic DNA sequence, a cDNA sequence, a vector sequence etc. In one embodiment, the template DNA oligonucleotides are synthesized in a tiling pattern that covers a source sequence, e.g., a genomic promoter sequence, in order in the 5' to 3' direction.

In various embodiments the RNA primer sequences generated in the template array are approximately the same size as the template consensus sequence in the range of about 4 ribonucleotides to about 20 ribonucleotides, e.g., about 5 ribonucleotides, 6 ribonucleotides, 7 ribonucleotides, 8 ribonucleotides, 9 ribonucleotides, 10 ribonucleotides, 11 ribonucleotides, 12 ribonucleotides, 13 ribonucleotides, 14 ribonucleotides, 16 ribonucleotides, 18 ribonucleotides, 18 ribonucleotides, or another length from about 4 ribonucleotides to about 20 ribonucleotides. In an exemplary embodiment, the RNA primer sequence comprises the complementary consensus sequence: 5'-GGACACGGCGAA-3' (SEQ ID NO:2).

In some embodiments the ribonucleoside phosphoramidites used to extend the 5'-linked ribonucleosides are RNase-resistant modified ribonucleosides. Examples of RNase-resistant modified ribonucleosides include, but are not limited to, 2-fluoro ribonucleosides, 2-amino ribonucleosides and 2-methoxy ribonucleosides.

Also described herein are methods to generate RNA arrays (including high density RNA arrays) from the above-described template arrays.

In some embodiments a method to generate an RNA array starts from a template array, which comprises an array of: (a) single-stranded template DNAs linked at their 3' ends to a solid support and comprising a consensus sequence; and (b) single-stranded RNA primers that are covalently linked at their 5' ends to the solid support, and that are complementary to the consensus sequence of the single-stranded template DNAs. The template RNA array is then incubated under hybridization conditions permissive for the 5'-covalently linked single-stranded RNA primers to hybridize with the complementary consensus sequence of the 3'-covalently linked single-stranded template DNAs. Suitable hybridization conditions are well known in the art, as described in, e.g., Tsai et al (2005), *Molecular Biotechnology,* 29(3):221-224. The hybridized RNA primers are then extended 5' to 3' along the single-stranded template DNAs using an RNA polymerase and ribonucleoside triphosphates to obtain double-stranded DNA-RNA hybrids. Afterwards, DNase treatment is used to eliminate template oligonucleotides within the DNA-RNA hybrids and unhybridized template DNA oligonucleotides, thereby yielding an RNA array.

In some embodiments, RNA primers, having a consensus sequence, are synthesized on a spacer layer first, to obtain a layer of 5'-linked RNA primers bound to a solid support surface. Afterwards, template DNA oligonucleotides comprising a consensus sequence at the 3' end, and a unique sequence at a 5' position relative to the consensus sequence, are added, in solution, to the 5'-linked RNA primer layer and hybridized. The hybridized RNA primers are then extended by an RNA polymerase to generate cRNA copies of the template DNA oligonucleotides. The DNA oligonucleotides are then removed by DNase digestion to obtain a cRNA array. In such embodiments, the unique cRNA sequence at each position is then "decoded" by sequential hybridization decoding as described in, e.g., Gunderson et al (2004), *Genome Research,* 14:870-877.

In some embodiments, RNA primers are 5'-linked primers on the surface of beads and comprising a consensus sequence. For individual pools of RNA-primer bound beads, a pool of template DNA oligonucleotides comprising a sequence complementary to the consensus sequence in the bead-bound primers and a unique sequence are then hybridized with the bead-bound RNA primers. Afterwards, an RNA polymerase is used to extend the hybridized bead-bound RNA primers to make bead-bound cRNAs of the template DNA oligonucleotides. The DNA is then removed to obtain a pool of bead-bound cRNAs (an "RNA bead pool"). One of ordinary skill in the art will appreciate that by using any of a number of known coding schemes (e.g., color-based or size based), RNA bead pools can be combined to obtain an RNA bead array, where each RNA bead pool within the array represents a unique RNA sequence.

In some embodiments the RNA polymerase used to extend the RNA primer is a T7 RNA polymerase or a T3 RNA polymerase. In one embodiment, the RNA polymerase to be used is T7 RNA polymerase. In some embodiments the ribonucleoside triphosphates to be used are modified ribonucleoside triphosphates. In one embodiment, the modified ribonucleoside triphosphates to be used in the method are RNase-resistant modified ribonucleoside triphosphates. Examples of suitable RNase-resistant modified ribonucleoside triphosphates include, but are not limited to, 2'-fluoro ribonucleosides and 2'-methoxy ribonucleosides. In some embodiments the modified ribonucleoside triphosphates are fluorescent modified ribonucleoside triphosphates. In cases where modified ribonucleosides are used for synthesis of array RNAs, modified ribonucleotides can be substituted for 1, 2, 3, or all four of the possible ribonucleoside types (A, U, G, C). In some embodiments for a given type of ribonucleoside, both modified and unmodified ribonucleosides are used for RNA synthesis with an RNA polymerase. The proportion of modified ribonucleotide used during RNA-polymerase-mediated RNA synthesis can range from 0 to 100%, e.g., from 5%, 10%, 20%, 30%, 50%, 60%, 70%, 90%, or another proportion of ribonucleosides to be used for RNA synthesis with an RNA polymerase.

III. Compositions

Described herein are RNA arrays (including high density RNA arrays) and array templates.

RNA Arrays

In some embodiments the RNA arrays described herein comprise RNAs linked at their 5' ends to a solid support. In some embodiments, the RNAs included in the high density array represent at least 20 unique RNA sequences and have a density of at least about 20 features/$cm^2$.

In some embodiments the RNAs are covalently linked at their 5' ends to the solid support, indirectly, through a bridging moiety and a spacer covalently bound to the surface of the solid support. For example, the spacer can be a polyethylene glycol with a molecular weight of about 2000 daltons (PEG 2000) or 4500 daltons (PEG 4500). The bridging moiety, in some embodiments is a photolabile or acid-labile protected deoxynucleoside phosphoramidite covalently linked to a 3' hydroxyl group of the spacer.

In some embodiments the 5' ends of the RNAs in the high density RNA array encompass a sequence of about 8 to about 15 ribonucleotides (e.g., 9, 10, 12, 14 or another number of ribonucleotides from about 8 to about 15 ribonucleotides), which are termed an "RNA primer complementary consensus sequence," herein. Typically, the RNA primer complementary consensus sequence comprises one or more 2'-methoxy ribonucleoside triphosphates, which are introduced during photolithographic synthesis of the RNA primer consensus sequence. While not wishing to be bound by theory, it is believed that the incorporation of 2-methoxy-ribonucleoside triphosphates facilitates hybridization by the RNA primer consensus sequence to its complement during synthesis of the high density RNA array, as described herein, and also confers RNase resistance.

In some embodiments the RNAs covalently linked to the solid support, comprise one or more modified ribonucleotides. In some embodiments the modified ribonucleotides confer resistance to ribonuclease. Examples of modified ribonucleotides that confer resistance to ribonucleases include, but are not limited to, 2'-methoxy ribonucleoside triphosphates, 2'-fluoro ribonucleoside triphosphates, 2'-amino ribonucleosides, 5-bromouridine-5'-triphosphates, 4-thiouridine-5'-triphosphates and 6-thioguanosine-5'-triphosphates. In other embodiments modified nucleotides include fluorescently modified ribonucleoside triphosphates (e.g., Cy5-ribonucleoside triphosphates) or hapten-modified ribonucleoside triphosphates (e.g., biotin-, or aminoallyl-modified ribonucleoside triphosphates) as known and used in the art. In some embodiments 100% of the constituent ribonucleotides in the RNAs of the high density RNA arrays are modified ribonucleotides. In other embodiments the proportion of modified ribonucleotides in the RNAs ranges from about 5% to about 95% of the ribonucleotides in the array RNAs, e.g., about 7%, 10%, 15%, 20%, 25%, 30%, 40%, 50%, 60%, 75%, or another proportion of the modified ribonucleotides ranging from about 5% to about 95% of the ribonucleotides. Where modified ribonucleotides are included in the array RNAs, 1, 2, 3, or all 4 of the ribonucleotides (i.e., A, U, G, or C) may include modified ribonucleotides.

Typically, the RNA arrays disclosed herein will represent at least 20 unique RNA sequences to about 1,000,000 unique RNA sequences, e.g., 30, 50, 100, 130, 145, 148, 150, 155, 160, 200, 500, 1,000, 1,500, 2,000, 3,000, 5,000, 10,000, 15,000, 20,000, 50,000, 100,000, 200,000, 400,000, 500,000, 600,000, 700,000, 800,000, 900,000, or another number of unique RNA sequences from at least 20 unique RNA sequences to about 1,000,000 unique RNA sequences. In one embodiment, the number of unique RNA sequences is about 50 to about 1,000 unique RNA sequences. In another embodiment, the number of unique RNA sequences is about 10 to about 200 unique RNA sequences. In another embodiment, the number of unique RNA sequences is about 100,000 sequences.

In various embodiments the length of the RNAs included in the disclosed RNA arrays ranges from at least about 20 ribonucleotides to about 80 ribonucleotides, e.g., about 25 ribonucleotides, 27 ribonucleotides, 28 ribonucleotides, 29 ribonucleotides, 35 ribonucleotides, 40 ribonucleotides, 60 ribonucleotides, 70 ribonucleotides, or another length from about 20 ribonucleotides to about 80 ribonucleotides.

In some embodiments the RNA arrays provided herein comprise a feature density of about 20 features/$cm^2$ to about 1,000,000 features/$cm^2$, e.g., about 25, 30, 40, 50, 60, 65, 70, 75, 80, 100, 120, 150, 200, 300, 500, 750, 1,000, 2,000, 2,500, 3,000, 3,500, 3,750, 4,200, 4,500, 5,000, 6,000, 6,500, 7,000, 7,500, 8,000, 9,000, 20,000, 50,000, 100,000, 200,000, 400,000, 500,000, 600,000, 700,000, 800,000, 900,000, or another feature density from about 20 features/cm$^2$ to about 1,000,000 features/cm$^2$. In some embodiments the disclosed RNA arrays have a feature density of about 50,000 features/cm$^2$ to about 1,000,000 features/cm$^2$.

Suitable solid support materials for RNA arrays include, but are not limited to, amorphous carbon, glassy carbon, and polymer or silanized glass. In some embodiments the solid support material used for RNA arrays is amorphous carbon.

Template Arrays

Also disclosed herein are template arrays that are useful intermediate compositions for generating the RNA arrays described herein. In some embodiments a template array comprises an array of (i) single-stranded template oligonucleotides linked at their 3' end to a solid support, comprising a consensus sequence, and capped by a protecting group (e.g., an phenoxyacetyl group) group at their 5' end; and (ii) single-stranded RNA primers that are covalently linked at their 5' end to the solid support, and that are complementary to the consensus sequence, wherein the single-stranded RNA primers hybridize to the single-stranded template DNAs.

In some embodiments of the template array, the 5' ends of the RNAs in the template array encompass a sequence of about 4 to about 20 ribonucleotides (e.g., 5, 6, 8, 9, 10, 12, 14, 16, 17, 18, or another number of ribonucleotides from about 4 to about 20 ribonucleotides), which are termed an "RNA primer complementary consensus sequence," herein. Typically, the RNA primer complementary consensus sequence comprises one or more modified ribonucleotides (e.g., RNase-resistant ribonucleotides such as 2'-methoxy ribonucleotides or 2'-fluoro ribonucleotides), or mixtures of unmodified and modified ribonucleotides, which are introduced during synthesis of the RNA primer consensus sequence.

In various embodiments single-stranded template DNA oligonucleotides and single-stranded RNA primers are linked at their 3' and 5' ends, respectively, to a bridging moiety (e.g., a deoxynucleotide), which in turn is linked to a spacer such as PEG 2000 or PEG 4500. The spacer provides a means of linking the single-stranded template DNA oligonucleotides and RNA primers to a solid support for the template array. Suitable solid support materials for template arrays include any materials compatible with RNA arrays, as described herein.

In some embodiments the template arrays provided herein comprise a feature density of about 20 features/cm$^2$ to about 1,000,000 features cm$^2$, e.g., about 25, 30, 40, 50, 60, 65, 70, 75, 80, 100, 120, 150, 200, 300, 500, 750, 1,000, 2,000, 2,500, 3,000, 3,500, 3,750, 4,200, 4,500, 5,000, 6,000, 6,500, 7,000, 7,500, 8,000, 9,000, 20,000, 50,000, 100,000, 200,000, 400,000, 500,000, 600,000, 700,000, 800,000, 900,000, or another feature density from about 20 features/cm$^2$ to about 1,000,000 features/cm$^2$. In some embodiments the disclosed RNA arrays have a feature density of about 5,000 features/cm$^2$ to about 1,000,000 features/cm$^2$.

In various embodiments template DNAs and RNA primers in the above-mentioned are in situ synthesized, in a base-by-base manner, using maskless array synthesizer (MAS) technology, as described in, e.g., Phillips et al (2008), *Nucleic Acids Res,* 36(1).

Kits

Also disclosed herein are kits that include a template array as described herein and any of (i) an RNA polymerase; (ii) ribonucleoside triphosphates; and (iii) a DNase. For example, in some cases the kit contains a template array and ribonucleoside triphosphates. In some embodiments the ribonucleoside triphosphates included in the kit are modified ribonucleoside triphosphates that are RNase-resistant. Such modified RNase-resistant nucleotides include, but are not limited, to 2'-methoxy ribonucleoside triphosphates, 2'-fluororibonucleoside triphosphates, 2'-amino ribonucleosides, 5-bromouridine-5'-triphosphates, 4-thiouridine-5'-triphosphates, and 6-thioguanosine-5'-triphosphates. In other embodiments the template array kit includes a template array and an RNA polymerase suitable for catalyzing primer-dependent biosynthesis of RNA using a DNA template. Examples of suitable RNA polymerases include, but are not limited to T7 RNA polymerase and T3 RNA polymerase. In some embodiments the template array kit contains a template array and a DNase, e.g., DNase I, T7 exonuclease, or Rec J exonuclease.

In one embodiment, the kits disclosed herein comprise a template array, an RNA polymerase, ribonucleoside triphosphates, and a DNase.

Optionally, any of the above-mentioned kits will also include instructions for generating an RNA array from the included template array using an RNA polymerase, ribonucleoside triphosphates, and a DNase according to the methods disclosed herein.

EXAMPLES

Example 1: Generation of an RNA Array from a Mouse Insulin-Like Growth Factor Binding Protein-1 (IGFPBP1) Promoter DNA Template In contrast to high density DNA microarrays that have been commercially available worldwide for more than a decade, a high density RNA microarray has not been generated until now due to the difficulty of synthesis. Hundred bases-long DNA microarrays have been made, owing to the mature state of the art for DNA synthesis and phosphoramidite chemistry, with high fidelity having been reported. We describe here an enzymatic method to fabricate high density RNA arrays by taking advantage of the high quality and length of DNA arrays.

FIG. 1A depicts the process of fabricating a high density DNA template array to be employed for enzymatic synthesis of a high density RNA array. In an exemplary procedure, light-directed photolithographic synthesis of DNA arrays is performed on a carbon surface that is functionalized with hydroxyl groups. A quarter of the full deprotecting dose of UV light (365 nm) is used to remove half of the photolabile protecting groups (3'-nitrophenylpropyloxycarbonyl, NPPOC) on the first layer of deoxyribonucleosides, which is covalently coupled to polyethylene glycol 2000 spacers on the carbon surface. The deoxyribonucleosides with free hydroxyl groups are then coupled with acid-labile DMT (4,4'-dimethoxytrityl) protected ribonucleoside phosphoramidites. A full dose of UV light is used to remove all of the photolabile protecting groups on the first layer and enables the light-directed photolithographic synthesis of DNA arrays using the method described in Wu et al supra. The 5' ends of DNA oligonucleotides on the surface are then capped by acetylation to block undesired synthesis from the termini. Each element of the DNA arrays includes a consensus DNA sequence at the 3' end, which later serves as a complement to the 2'-methoxy RNA primer. Finally, the acid-labile DMT protecting groups on the first layer are removed with dichloroacetic acid to reveal 3' hydroxyl groups of the ribonucleosides for the chemical synthesis of 2'-methoxy RNA primer, that includes the consensus sequence, in the 5' to 3' direction, which is then extended enzymatically by T7 RNA polymerase in a subsequent step.

Figure 1B:
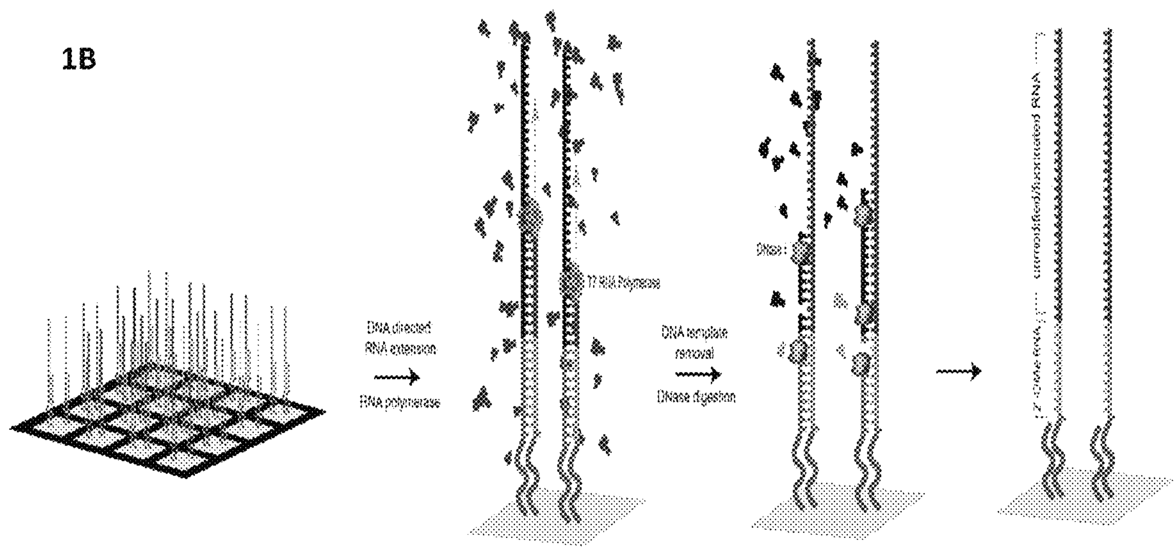

FIG. 1B lays out the process of enzymatic synthesis of a high density RNA array. The oligonucleotide array was denatured and reannealed for RNA extension by T7 or T3 RNA polymerase). Either unmodified or fluorinated ribonucleoside triphosphates can be used for the synthesis of unmodified or 2'-fluorine-modified RNA oligonucleotides for better resistance to RNase. DNA endonuclease, e.g., DNase I, is then used to remove the DNA template from the array to yield the final high density RNA array.

To demonstrate proof of concept, an RNA tiling array was fabricated to characterize the products of a T7 exonuclease (a 5' dsDNA exonuclease) digestion reaction. The RNA tiling array allowed us to optimize the generation of single-stranded DNA for sequence-specific capture on the RNA array. We fabricated an RNA tiling array containing all possible 20mer complements, thereby spanning the entire 180 base long IGFBP1 promoter DNA in 161 single-base increments (see Text 1 for the target sequence, Table 1 for design of the "DNA template array", and Table 2 for the copied "tiling RNA array").

The DNA fragment corresponding to positions −205 to −25 of the mouse IGFBP1 promoter was amplified by PCR from NIH 3T3 (mouse embryonic fibroblast cell line) genomic DNA (purchased from New England Biolabs, Mass., USA):

```
                                         (SEQ ID NO: 3)
  1 TTAGCTCCTG TCCCAGTCCA TCACCACGGG ACAAACATAG TAGAAAACCT

 61 GATCCCTTTA CCCCCTTCCA CCCACGGTTT GTGTAGAGCT CACAAGCAAA

101 ACAAACTTAT TTTGAACACT GGGGTCCTAG CACGCTGCCC TGACAATCAT

161 TAACCTGTGC CGCACAGCCA GCCCTTCATA
```

The primer sequences used to amplify the IGFBP1 promoter amplicon are: 5'-TTA GCT CCT GTC CCA GTC CAT-3' (SEQ ID NO:4) and 5'-TAT GAA GGG CTG GCT GTG C-3' (SEQ ID NO:5). A 5' phosphorothioate protected oligonucleotide with 6-carboxyfluorescein (FAM) tag (5'-T*/iFluorT/A GCT CCT GTC CCA GTC CAT-3') (SEQ ID NO:6) was used to produce a 180 bp fluorescently tagged IGFBP1 promoter DNA amplicon.

A DNA template array was generated by first synthesizing a template consensus sequence (5'-TTCGCCGTGTCC-3') (SEQ ID NO:1) in array format. The template consensus sequence, which is complementary to an RNA primer consensus sequence, was synthesized from 3' to 5' at all positions on the array prior to the synthesis of the sequences in Table 1 at various positions from 3' to 5' using 5'-NPPOC-protected deoxyribonucleoside phosphoramidites. Afterwards, the position-specific sequences were also synthesized 3' to 5'. So, for example, at locations in the array, where the sequence position is listed as "1-20" in Table 1, the actual complete sequence at those locations on the array, is

```
                                   (SEQ ID NO: 7)
3'-CCTGTGCCGCTT-ACCTGACCCTGTCCTCGATT-5'
```

(where the underlining indicates the complement of the RNA consensus sequence).

The sequences listed in Table 1 served as the DNA templates for an RNA polymerase extension reaction to produce the RNA array that could be used to capture IGFBP1 promoter DNA.

DNA quality control probe 1 (DNA QC1) is the complementary sequence to the fluorescently labeled ssDNA called "ApoE" for quality control purposes. DNA quality probe 2 (DNA QC2) is the complementary sequence to the fluorescently labeled ssDNA called "w1282" for quality control purposes. DNA quality probe 3 (DNA QC3) is the same probe sequence as the fluorescently labeled ssDNA called "ApoE" for quality control purposes. DNA quality probe 4 (DNA QC4) is the same probe sequence as the fluorescently labeled ssDNA called "w1282" for quality control purposes.

The fluorescently labeled "ApoE" ssDNA is capturable to QC1 but not QC3 in the template array. The fluorescently labeled "w1282" ssDNA is capturable to QC2 but not QC4 in the "template DNA array.

TABLE 1

IGFBP1 promoter template DNA array oligonucleotide sequences.

| Name/Position | DNA Sequence (3'-->5') |
|---|---|
| Blank | |
| DNA QC1 | CGGCTACTGGACGTTCTCA (SEQ ID NO: 8) |
| DNA QC2 | TATTGAAACGTTGTCACC (SEQ ID NO: 9) |
| DNA QC3 | TGAGAACGTCCAGTAGCCG (SEQ ID NO: 10) |
| DNA QC4 | GGTGACAACGTTTCAATA (SEQ ID NO: 11) |
| 161 to 180 | 3'-ATACTTCCCGACCGACACGC-5' (SEQ ID NO: 12) |
| 160 to 179 | TACTTCCCGACCGACACGCC (SEQ ID NO: 13) |
| 159 to 178 | ACTTCCCGACCGACACGCCG (SEQ ID NO: 14) |
| 158 to 177 | CTTCCCGACCGACACGCCGT (SEQ ID NO: 15) |
| 157 to 176 | TTCCCGACCGACACGCCGTG (SEQ ID NO: 16) |
| 156 to 175 | TCCCGACCGACACGCCGTGT (SEQ ID NO: 17) |
| 155 to 174 | CCCGACCGACACGCCGTGTC (SEQ ID NO: 18) |
| 154 to 173 | CCGACCGACACGCCGTGTCC (SEQ ID NO: 19) |

TABLE 1 -continued

| IGFBP1 promoter template DNA array oligonucleotide sequences. | |
|---|---|
| Name/Position | DNA Sequence (3'-->5') |
| 153 to 172 | CGACCGACACGCCGTGTCCA (SEQ ID NO: 20) |
| 152 to 171 | GACCGACACGCCGTGTCCAA (SEQ ID NO: 21) |
| 151 to 170 | ACCGACACGCCGTGTCCAAT (SEQ ID NO: 22) |
| 150 to 169 | CCGACACGCCGTGTCCAATT (SEQ ID NO: 23) |
| 149 to 168 | CGACACGCCGTGTCCAATTA (SEQ ID NO: 24) |
| 148 to 167 | GACACGCCGTGTCCAATTAC (SEQ ID NO: 25) |
| 147 to 166 | ACACGCCGTGTCCAATTACT (SEQ ID NO: 26) |
| 146 to 165 | CACGCCGTGTCCAATTACTA (SEQ ID NO: 27) |
| 145 to 164 | ACGCCGTGTCCAATTACTAA (SEQ ID NO: 28) |
| 144 to 163 | CGCCGTGTCCAATTACTAAC (SEQ ID NO: 29) |
| 143 to 162 | GCCGTGTCCAATTACTAACA (SEQ ID NO: 30) |
| 142 to 161 | CCGTGTCCAATTACTAACAG (SEQ ID NO: 31) |
| 141 to 160 | CGTGTCCAATTACTAACAGT (SEQ ID NO: 32) |
| 140 to 159 | GTGTCCAATTACTAACAGTC (SEQ ID NO: 33) |
| 139 to 158 | TGTCCAATTACTAACAGTCC (SEQ ID NO: 34) |
| 138 to 157 | GTCCAATTACTAACAGTCCC (SEQ ID NO: 35) |
| 137 to 156 | TCCAATTACTAACAGTCCCG (SEQ ID NO: 36) |
| 136 to 155 | CCAATTACTAACAGTCCCGT (SEQ ID NO: 37) |
| 135 to 154 | CAATTACTAACAGTCCCGTC (SEQ ID NO: 38) |
| 134 to 153 | AATTACTAACAGTCCCGTCG (SEQ ID NO: 39) |
| 133 to 152 | ATTACTAACAGTCCCGTCGC (SEQ ID NO: 40) |
| 132 to 151 | TTACTAACAGTCCCGTCGCA (SEQ ID NO: 41) |
| 131 to 150 | TACTAACAGTCCCGTCGCAC (SEQ ID NO: 42) |
| 130 to 149 | ACTAACAGTCCCGTCGCACG (SEQ ID NO: 43) |
| 129 to 148 | CTAACAGTCCCGTCGCACGA (SEQ ID NO: 44) |

TABLE 1 -continued

| IGFBP1 promoter template DNA array oligonucleotide sequences. | |
|---|---|
| Name/Position | DNA Sequence (3'-->5') |
| 128 to 147 | TAACAGTCCCGTCGCACGAT (SEQ ID NO: 45) |
| 127 to 146 | AACAGTCCCGTCGCACGATC (SEQ ID NO: 46) |
| 126 to 145 | ACAGTCCCGTCGCACGATCC (SEQ ID NO: 47) |
| 125 to 144 | CAGTCCCGTCGCACGATCCT (SEQ ID NO: 48) |
| 124 to 143 | AGTCCCGTCGCACGATCCTG (SEQ ID NO: 49) |
| 123 to 142 | GTCCCGTCGCACGATCCTGG (SEQ ID NO: 50) |
| 122 to 141 | TCCCGTCGCACGATCCTGGG (SEQ ID NO: 51) |
| 121 to 140 | CCCGTCGCACGATCCTGGGG (SEQ ID NO: 52) |
| 120 to 139 | CCGTCGCACGATCCTGGGGT (SEQ ID NO: 53) |
| 119 to 138 | CGTCGCACGATCCTGGGGTC (SEQ ID NO: 54) |
| 118 to 137 | GTCGCACGATCCTGGGGTCA (SEQ ID NO: 55) |
| 117 to 136 | TCGCACGATCCTGGGGTCAC (SEQ ID NO: 56) |
| 116 to 135 | CGCACGATCCTGGGGTCACA (SEQ ID NO: 57) |
| 115 to 134 | GCACGATCCTGGGGTCACAA (SEQ ID NO: 58) |
| 114 to 133 | CACGATCCTGGGGTCACAAG (SEQ ID NO: 59) |
| 113 to 132 | ACGATCCTGGGGTCACAAGT (SEQ ID NO: 60) |
| 112 to 131 | CGATCCTGGGGTCACAAGTT (SEQ ID NO: 61) |
| 111 to 130 | GATCCTGGGGTCACAAGTTT (SEQ ID NO: 62) |
| 110 to 129 | ATCCTGGGGTCACAAGTTTT (SEQ ID NO: 63) |
| 109 to 128 | TCCTGGGGTCACAAGTTTTA (SEQ ID NO: 64) |
| 108 to 127 | CCTGGGGTCACAAGTTTTAT (SEQ ID NO: 65) |
| 107 to 126 | CTGGGGTCACAAGTTTTATT (SEQ ID NO: 66) |
| 106 to 125 | TGGGGTCACAAGTTTTATTC (SEQ ID NO: 67) |
| 105 to 124 | GGGGTCACAAGTTTTATTCA (SEQ ID NO: 68) |
| 104 to 123 | GGGTCACAAGTTTTATTCAA (SEQ ID NO: 69) |

TABLE 1 -continued

IGFBP1 promoter template DNA array oligonucleotide sequences.

| Name/Position | DNA Sequence (3'-->5') |
|---|---|
| 103 to 122 | GGTCACAAGTTTTATTCAAA (SEQ ID NO: 70) |
| 102 to 121 | GTCACAAGTTTTATTCAAAC (SEQ ID NO: 71) |
| 101 to 120 | TCACAAGTTTTATTCAAACA (SEQ ID NO: 72) |
| 100 to 119 | CACAAGTTTTATTCAAACAA (SEQ ID NO: 73) |
| 99 to 118 | ACAAGTTTTATTCAAACAAA (SEQ ID NO: 74) |
| 98 to 117 | CAAGTTTTATTCAAACAAAA (SEQ ID NO: 75) |
| 97 to 116 | AAGTTTTATTCAAACAAAAC (SEQ ID NO: 76) |
| 96 to 115 | AGTTTTATTCAAACAAAACG (SEQ ID NO: 77) |
| 95 to 114 | GTTTTATTCAAACAAAACGA (SEQ ID NO: 78) |
| 94 to 113 | TTTTATTCAAACAAAACGAA (SEQ ID NO: 79) |
| 93 to 112 | TTTATTCAAACAAAACGAAC (SEQ ID NO: 80) |
| 92 to 111 | TTATTCAAACAAAACGAACA (SEQ ID NO: 81) |
| 91 to 110 | TATTCAAACAAAACGAACAC (SEQ ID NO: 82) |
| 90 to 109 | ATTCAAACAAAACGAACACT (SEQ ID NO: 83) |
| 89 to 108 | TTCAAACAAAACGAACACTC (SEQ ID NO: 84) |
| 88 to 107 | TCAAACAAAACGAACACTCG (SEQ ID NO: 85) |
| 87 to 106 | CAAACAAAACGAACACTCGA (SEQ ID NO: 86) |
| 86 to 105 | AAACAAAACGAACACTCGAG (SEQ ID NO: 87) |
| 85 to 104 | AACAAAACGAACACTCGAGA (SEQ ID NO: 88) |
| 84 to 103 | ACAAAACGAACACTCGAGAT (SEQ ID NO: 89) |
| 83 to 102 | CAAAACGAAC ACTCGAGATG (SEQ ID NO: 90) |
| 82 to 101 | AAAACGAACA CTCGAGATGT (SEQ ID NO: 91) |
| 81 to 100 | AAACGAACAC TCGAGATGTG (SEQ ID NO: 92) |

TABLE 1 -continued

IGFBP1 promoter template DNA array oligonucleotide sequences.

| Name/Position | DNA Sequence (3'-->5') |
|---|---|
| 80 to 99 | AACGAACACT CGAGATGTGT (SEQ ID NO: 93) |
| 79 to 98 | ACGAACACTC GAGATGTGTT (SEQ ID NO: 94) |
| 78 to 97 | CGAACACTCG AGATGTGTTT (SEQ ID NO: 95) |
| 77 to 96 | GAACACTCGA GATGTGTTTG (SEQ ID NO: 96) |
| 76 to 95 | AACACTCGAG ATGTGTTTGG (SEQ ID NO: 97) |
| 75 to 94 | ACACTCGAGA TGTGTTTGGC (SEQ ID NO: 98) |
| 74 to 93 | CACTCGAGAT GTGTTTGGCA (SEQ ID NO: 99) |
| 73 to 92 | ACTCGAGATG TGTTTGGCAC (SEQ ID NO: 100) |
| 72 to 91 | CTCGAGATGT GTTTGGCACC (SEQ ID NO: 101) |
| 71 to 90 | TCGAGATGTG TTTGGCACCC (SEQ ID NO: 102) |
| 70 to 89 | CGAGATGTGT TTGGCACCCA (SEQ ID NO: 103) |
| 69 to 88 | GAGATGTGTTT GGCACCCAC (SEQ ID NO: 104) |
| 68 to 87 | AGATGTGTTTG GCACCCACC (SEQ ID NO: 105) |
| 67 to 86 | GATGTGTTTGG CACCCACCT (SEQ ID NO: 106) |
| 66 to 85 | ATGTGTTTGGC ACCCACCTT (SEQ ID NO: 107) |
| 65 to 84 | TGTGTTTGGCA CCCACCTTC (SEQ ID NO: 108) |
| 64 to 83 | GTGTTTGGCAC CCACCTTCC (SEQ ID NO: 109) |
| 63 to 82 | TGTTTGGCACC CACCTTCCC (SEQ ID NO: 110) |

TABLE 1 -continued

| IGFBP1 promoter template DNA array oligonucleotide sequences. | |
|---|---|
| Name/Position | DNA Sequence (3'-->5') |
| 62 to 81 | GTTTGGCACCC ACCTTCCCC (SEQ ID NO: 111) |
| 61 to 80 | TTTGGCACCCA CCTTCCCCC (SEQ ID NO: 112) |
| 60 to 79 | TTGGCACCCA CCTTCCCCCA (SEQ ID NO: 113) |
| 59 to 78 | TGGCACCCAC CTTCCCCCAT (SEQ ID NO: 114) |
| 58 to 77 | GGCACCCACC TTCCCCCATT (SEQ ID NO: 115) |
| 57 to 76 | GCACCCACCTT CCCCCATTT (SEQ ID NO: 116) |
| 56 to 75 | CACCCACCTTC CCCCATTTC (SEQ ID NO: 117) |
| 55 to 74 | ACCCACCTTCC CCCATTTCC (SEQ ID NO: 118) |
| 54 to 73 | CCCACCTTCCC CCATTTCCC (SEQ ID NO: 119) |
| 53 to 72 | CCACCTTCCCC CATTTCCCT (SEQ ID NO: 120) |
| 52 to 71 | CACCTTCCCCC ATTTCCCTA (SEQ ID NO: 121) |
| 51 to 70 | ACCTTCCCCCA TTTCCCTAG (SEQ ID NO: 122) |
| 50 to 69 | CCTTCCCCCAT TTCCCTAGT (SEQ ID NO: 123) |
| 49 to 68 | CTTCCCCCATT TCCCTAGTC |
| 48 to 67 | TTCCCCCATTT CCCTAGTCC (SEQ ID NO: 124) |
| 47 to 66 | TCCCCCATTTC CCTAGTCCA (SEQ ID NO: 125) |
| 46 to 65 | CCCCCATTTCC CTAGTCCAA (SEQ ID NO: 126) |
| 45 to 64 | CCCCATTTCCC TAGTCCAAA (SEQ ID NO: 127) |
| 44 to 63 | CCCATTTCCCT AGTCCAAAA (SEQ ID NO: 128) |

TABLE 1 -continued

| IGFBP1 promoter template DNA array oligonucleotide sequences. | |
|---|---|
| Name/Position | DNA Sequence (3'-->5') |
| 43 to 62 | CCATTTCCCTA GTCCAAAAG |
| 42 to 61 | CATTTCCCTAG TCCAAAAGA (SEQ ID NO: 129) |
| 41 to 60 | ATTTCCCTAGT CCAAAAGAT (SEQ ID NO: 130) |
| 40 to 59 | TTTCCCTAGTC CAAAAGATG |
| 39 to 58 | TTCCCTAGTCC AAAAGATGA (SEQ ID NO: 131) |
| 38 to 57 | TCCCTAGTCCA AAAGATGAT (SEQ ID NO: 132) |
| 37 to 56 | CCCTAGTCCA AAAGATGATA (SEQ ID NO: 133) |
| 36 to 55 | CCTAGTCCAA AAGATGATAC (SEQ ID NO: 134) |
| 35 to 54 | CTAGTCCAAA AGATGATACA |
| 34 to 53 | TAGTCCAAAA GATGATACAA (SEQ ID NO: 135) |
| 33 to 52 | AGTCCAAAAG ATGATACAAA (SEQ ID NO: 136) |
| 32 to 51 | GTCCAAAAGA TGATACAAAC (SEQ ID NO: 137) |
| 31 to 50 | TCCAAAAGAT GATACAAACA (SEQ ID NO: 138) |
| 30 to 49 | CCAAAAGATG ATACAAACAG (SEQ ID NO: 139) |
| 29 to 48 | CAAAAGATGA TACAAACAGG (SEQ ID NO: 140) |
| 28 to 47 | AAAAGATGAT ACAAACAGGG (SEQ ID NO: 141) |
| 27 to 46 | AAAGATGATA CAAACAGGGC (SEQ ID NO: 142) |
| 26 to 45 | AAGATGATAC AAACAGGGCA (SEQ ID NO: 143) |
| 25 to 44 | AGATGATACA AACAGGGCAC (SEQ ID NO: 144) |

TABLE 1 -continued

IGFBP1 promoter template DNA array oligonucleotide sequences.

| Name/Position | DNA Sequence (3'-->5') |
|---|---|
| 24 to 43 | GATGATACAA ACAGGGCACC (SEQ ID NO: 145) |
| 23 to 42 | ATGATACAAA CAGGGCACCA (SEQ ID NO: 146) |
| 22 to 41 | TGATACAAAC AGGGCACCAC (SEQ ID NO: 147) |
| 21 to 40 | GATACAAACA GGGCACCACT (SEQ ID NO: 148) |
| 20 to 39 | ATACAAACAG GGCACCACTA (SEQ ID NO: 149) |
| 19 to 38 | TACAAACAGG GCACCACTAC (SEQ ID NO: 150) |
| 18 to 37 | ACAAACAGGG CACCACTACC (SEQ ID NO: 151) |
| 17 to 36 | CAAACAGGGC ACCACTACCT (SEQ ID NO: 152) |
| 16 to 35 | AAACAGGGCA CCACTACCTG (SEQ ID NO: 153) |
| 15 to 34 | AACAGGGCAC CACTACCTGA (SEQ ID NO: 154) |
| 14 to 33 | ACAGGGCACC ACTACCTGAC (SEQ ID NO: 155) |
| 13 to 32 | CAGGGCACCA CTACCTGACC (SEQ ID NO: 156) |
| 12 to 31 | AGGGCACCAC TACCTGACCC (SEQ ID NO: 157) |
| 11 to 30 | GGGCACCACT ACCTGACCCT (SEQ ID NO: 158) |
| 10 to 29 | GGCACCACTA CCTGACCCTG (SEQ ID NO: 159) |
| 9 to 28 | GCACCACTAC CTGACCCTGT (SEQ ID NO: 160) |
| 8 to 27 | CACCACTACCT GACCCTGTC (SEQ ID NO: 161) |
| 7 to 26 | ACCACTACCT GACCCTGTCC (SEQ ID NO: 162) |
| 6 to 25 | CCACTACCTG ACCCTGTCCT (SEQ ID NO: 163) |
| 5 to 24 | CACTACCTGA CCCTGTCCTC (SEQ ID NO: 164) |
| 4 to 23 | ACTACCTGAC CCTGTCCTCG (SEQ ID NO: 165) |
| 3 to 22 | CTACCTGACCC TGTCCTCGA (SEQ ID NO: 166) |
| 2 to 21 | TACCTGACCCT GTCCTCGAT (SEQ ID NO: 167) |
| 1 to 20 | ACCTGACCCT GTCCTCGATT (SEQ ID NO: 168) |

After completion of" the DNA template sequence array, the RNA primer consensus sequence (5'-GGACACGGCGAA-3') (SEQ ID NO:2) was synthesized in close proximity to positions occupied by the previously synthesized DNA template sequences. The RNA primer consensus sequence was synthesized from 5' to 3' using 3'-O-DMT-protected 2'-OMe-ribonucleoside phosphoramidites at multiple locations within the array. The newly synthesized RNA primers then hybridized to the DNA template consensus sequence, and served to prime RNA synthesis with T7 RNA polymerase and a DNA sequence template, as shown in FIG. 1. DNA endonuclease, e.g., DNase I, was then used to remove the DNA template from the array to yield the final high density RNA array. The RNA sequences synthesized in array format are shown in Table 2.

The sequences listed below are the RNA sequences enzymatically synthesized on the RNA array. RNA quality control probe 1 (RNA QC1) is the same probe sequence as the fluorescently labeled ssDNA called "ApoE" for quality control purposes. RNA quality control probe 2 (RNA QC2) is the same probe sequence as the fluorescently labeled ssDNA called "w1282" for quality control purposes. RNA quality control probe 3 (RNA QC3) is the complementary sequence to the fluorescently labeled ssDNA called "ApoE" for quality control purposes. RNA quality control probe 4 (RNA QC4) is the complementary sequence to the fluorescently labeled ssDNA called "w1282" for quality control purposes.

The fluorescently labeled "ApoE" ssDNA is capturable to QC3 but not QC1 in the "tiling RNA array." The fluorescently labeled "w1282" ssDNA is capturable to QC4 but not QC2 in the "tiling RNA array."

TABLE 2

IGFBP1 promoter tiling RNA array oligonucleotide sequences.

| Name/Position | RNA Sequence (5'-->3') |
|---|---|
| Blank | |
| RNA QC1 | GCCGAUGACCUGCAAGAGU (SEQ ID NO: 169) |

TABLE 2-continued

IGFBP1 promoter tiling RNA array oligonucleotide sequences.

| Name/Position | RNA Sequence (5'-->3') |
| --- | --- |
| RNA QC2 | AUAACUUUGCAACAGUGG (SEQ ID NO: 170) |
| RNA QC3 | ACUCUUGCAGGUCAUCGGC (SEQ ID NO: 171) |
| RNA QC4 | CCACUGUUGCAAAGUUAU (SEQ ID NO: 172) |
| 180 to 161 | UAUGAAGGGCUGGCUGUGCG (SEQ ID NO: 173) |
| 179 to 160 | AUGAAGGGCUGGCUGUGCGG (SEQ ID NO: 174) |
| 178 to 159 | UGAAGGGCUGGCUGUGCGGC (SEQ ID NO: 175) |
| 177 to 158 | GAAGGGCUGGCUGUGCGGCA (SEQ ID NO: 176) |
| 176 to 157 | AAGGGCUGGCUGUGCGGCAC (SEQ ID NO: 177) |
| 175 to 156 | AGGGCUGGCUGUGCGGCACA (SEQ ID NO: 178) |
| 174 to 155 | GGGCUGGCUGUGCGGCACAG (SEQ ID NO: 179) |
| 173 to 154 | GGCUGGCUGUGCGGCACAGG (SEQ ID NO: 180) |
| 172 to 153 | GCUGGCUGUGCGGCACAGGU (SEQ ID NO: 181) |
| 171 to 152 | CUGGCUGUGCGGCACAGGUU (SEQ ID NO: 182) |
| 170 to 151 | UGGCUGUGCGGCACAGGUUA (SEQ ID NO: 183) |
| 169 to 150 | GGCUGUGCGGCACAGGUUAA (SEQ ID NO: 184) |
| 168 to 149 | GCUGUGCGGCACAGGUUAAU (SEQ ID NO: 185) |
| 167 to 148 | CUGUGCGGCACAGGUUAAUG (SEQ ID NO: 186) |
| 166 to 147 | UGUGCGGCACAGGUUAAUGA (SEQ ID NO: 187) |
| 165 to 146 | GUGCGGCACAGGUUAAUGAU (SEQ ID NO: 188) |
| 164 to 145 | UGCGGCACAGGUUAAUGAUU (SEQ ID NO: 189) |
| 163 to 144 | GCGGCACAGGUUAAUGAUUG (SEQ ID NO: 190) |
| 162 to 143 | CGGCACAGGUUAAUGAUUGU (SEQ ID NO: 191) |
| 161 to 142 | GGCACAGGUUAAUGAUUGUC (SEQ ID NO: 192) |
| 160 to 141 | GCACAGGUUAAUGAUUGUCA (SEQ ID NO: 193) |
| 159 to 140 | CACAGGUUAAUGAUUGUCAG (SEQ ID NO: 194) |

TABLE 2-continued

IGFBP1 promoter tiling RNA array oligonucleotide sequences.

| Name/Position | RNA Sequence (5'-->3') |
| --- | --- |
| 158 to 139 | ACAGGUUAAUGAUUGUCAGG (SEQ ID NO: 195) |
| 157 to 138 | CAGGUUAAUGAUUGUCAGGG (SEQ ID NO: 196) |
| 156 to 137 | AGGUUAAUGAUUGUCAGGGC (SEQ ID NO: 197) |
| 155 to 136 | GGUUAAUGAUUGUCAGGGCA (SEQ ID NO: 198) |
| 154 to 135 | GUUAAUGAUUGUCAGGGCAG (SEQ ID NO: 199) |
| 153 to 134 | UUAAUGAUUGUCAGGGCAGC (SEQ ID NO: 200) |
| 152 to 133 | UAAUGAUUGUCAGGGCAGCG (SEQ ID NO: 201) |
| 151 to 132 | AAUGAUUGUCAGGGCAGCGU (SEQ ID NO: 202) |
| 150 to 131 | AUGAUUGUCAGGGCAGCGUG (SEQ ID NO: 203) |
| 149 to 130 | UGAUUGUCAGGGCAGCGUGC (SEQ ID NO: 204) |
| 148 to 129 | GAUUGUCAGGGCAGCGUGCU (SEQ ID NO: 205) |
| 147 to 128 | AUUGUCAGGGCAGCGUGCUA (SEQ ID NO: 206) |
| 146 to 127 | UUGUCAGGGCAGCGUGCUAG (SEQ ID NO: 207) |
| 145 to 126 | UGUCAGGGCAGCGUGCUAGG (SEQ ID NO: 208) |
| 144 to 125 | GUCAGGGCAGCGUGCUAGGA (SEQ ID NO: 209) |
| 143 to 124 | UCAGGGCAGCGUGCUAGGAC (SEQ ID NO: 210) |
| 142 to 123 | CAGGGCAGCGUGCUAGGACC (SEQ ID NO: 211) |
| 141 to 122 | AGGGCAGCGUGCUAGGACCC (SEQ ID NO: 212) |
| 140 to 121 | GGGCAGCGUGCUAGGACCCC (SEQ ID NO: 213) |
| 139 to 120 | GGCAGCGUGCUAGGACCCCA (SEQ ID NO: 214) |
| 138 to 119 | GCAGCGUGCUAGGACCCCAG (SEQ ID NO: 215) |
| 137 to 118 | CAGCGUGCUAGGACCCCAGU (SEQ ID NO: 216) |
| 136 to 117 | AGCGUGCUAGGACCCCAGUG (SEQ ID NO: 217) |
| 135 to 116 | GCGUGCUAGGACCCCAGUGU (SEQ ID NO: 218) |
| 134 to 115 | CGUGCUAGGACCCCAGUGUU (SEQ ID NO: 219) |

TABLE 2-continued

IGFBP1 promoter tiling RNA array oligonucleotide sequences.

| Name/Position | RNA Sequence (5'-->3') |
|---|---|
| 133 to 114 | GUGCUAGGACCCCAGUGUUC (SEQ ID NO: 220) |
| 132 to 113 | UGCUAGGACCCCAGUGUUCA (SEQ ID NO: 221) |
| 131 to 112 | GCUAGGACCCCAGUGUUCAA (SEQ ID NO: 222) |
| 130 to 111 | CUAGGACCCCAGUGUUCAAA (SEQ ID NO: 223) |
| 129 to 110 | UAGGACCCCAGUGUUCAAAA (SEQ ID NO: 224) |
| 128 to 109 | AGGACCCCAGUGUUCAAAAU (SEQ ID NO: 225) |
| 127 to 108 | GGACCCCAGUGUUCAAAAUA (SEQ ID NO: 226) |
| 126 to 107 | GACCCCAGUGUUCAAAAUAA (SEQ ID NO: 227) |
| 125 to 106 | ACCCCAGUGUUCAAAAUAAG (SEQ ID NO: 228) |
| 124 to 105 | CCCCAGUGUUCAAAAUAAGU (SEQ ID NO: 229) |
| 123 to 104 | CCCAGUGUUCAAAAUAAGUU (SEQ ID NO: 230) |
| 122 to 103 | CCAGUGUUCAAAAUAAGUUU (SEQ ID NO: 231) |
| 121 to 102 | CAGUGUUCAAAAUAAGUUUG (SEQ ID NO: 232) |
| 120 to 101 | AGUGUUCAAAAUAAGUUUGU (SEQ ID NO: 233) |
| 119 to 100 | GUGUUCAAAAUAAGUUUGUU (SEQ ID NO: 234) |
| 118 to 99 | UGUUCAAAAUAAGUUUGUUU (SEQ ID NO: 235) |
| 117 to 98 | GUUCAAAAUAAGUUUGUUUU (SEQ ID NO: 236) |
| 116 to 97 | UUCAAAAUAAGUUUGUUUUG (SEQ ID NO: 237) |
| 115 to 96 | UCAAAAUAAGUUUGUUUUGC (SEQ ID NO: 238) |
| 114 to 95 | CAAAAUAAGUUUGUUUUGCU (SEQ ID NO: 239) |
| 113 to 94 | AAAAUAAGUUUGUUUUGCUU (SEQ ID NO: 240) |
| 112 to 93 | AAAUAAGUUUGUUUUGCUUG (SEQ ID NO: 241) |
| 111 to 92 | AAUAAGUUUGUUUUGCUUGU (SEQ ID NO: 252) |
| 110 to 91 | AUAAGUUUGUUUUGCUUGUG (SEQ ID NO: 243) |
| 109 to 90 | UAAGUUUGUUUUGCUUGUGA (SEQ ID NO: 244) |

TABLE 2-continued

IGFBP1 promoter tiling RNA array oligonucleotide sequences.

| Name/Position | RNA Sequence (5'-->3') |
|---|---|
| 108 to 89 | AAGUUUGUUUUGCUUGUGAG (SEQ ID NO: 245) |
| 107 to 88 | AGUUUGUUUUGCUUGUGAGC (SEQ ID NO: 246) |
| 106 to 87 | GUUUGUUUUGCUUGUGAGCU (SEQ ID NO: 247) |
| 105 to 86 | UUUGUUUUGCUUGUGAGCUC (SEQ ID NO: 248) |
| 104 to 85 | UUGUUUUGCUUGUGAGCUCU (SEQ ID NO: 249) |
| 103 to 84 | UGUUUUGCUUGUGAGCUCUA (SEQ ID NO: 250) |
| 102 to 83 | GUUUUGCUUGUGAG CUCUAC (SEQ ID NO: 250) |
| 101 to 82 | UUUUGCUUGUGAGC UCUACA (SEQ ID NO: 252) |
| 100 to 81 | UUUGCUUGUGAGCU CUACAC (SEQ ID NO: 253) |
| 99 to 80 | UUGCUUGUGAGCUC UACACA (SEQ ID NO: 254) |
| 98 to 79 | UGCUUGUGAGCUCU ACACAA |
| 97 to 78 | GCUUGUGAGCUCUAC ACAAA (SEQ ID NO: 255) |
| 96 to 77 | CUUGUGAGCUCUACA CAAAC (SEQ ID NO: 256) |
| 95 to 76 | UUGUGAGCUCUACAC AAACC (SEQ ID NO: 257) |
| 94 to 75 | UGUGAGCUCUACACA AACCG (SEQ ID NO: 258) |
| 93 to 74 | GUGAGCUCUACACAA ACCGU (SEQ ID NO: 259) |
| 92 to 73 | UGAGCUCUACACAAA CCGUG |
| 91 to 72 | GAGCUCUACACAAAC CGUGG (SEQ ID NO: 260) |
| 90 to 71 | AGCUCUACACAAACC GUGGG (SEQ ID NO: 261) |
| 89 to 70 | GCUCUACACAAACCG UGGGU (SEQ ID NO: 262) |

TABLE 2-continued

IGFBP1 promoter tiling RNA array oligonucleotide sequences.

| Name/Position | RNA Sequence (5'-->3') |
|---|---|
| 88 to 69 | CUCUACACAAACCGU GGGUG (SEQ ID NO: 263) |
| 87 to 68 | UCUACACAAACCGUG GGUGG (SEQ ID NO: 264) |
| 86 to 67 | CUACACAAACCGUGG GUGGA (SEQ ID NO: 265) |
| 85 to 66 | UACACAAACCGUGGG UGGAA (SEQ ID NO: 266) |
| 84 to 65 | ACACAAACCGUGGGU GGAAG (SEQ ID NO: 267) |
| 83 to 64 | CACAAACCGUGGGUG GAAGG (SEQ ID NO: 268) |
| 82 to 63 | ACAAACCGUGGGUG GAAGGG (SEQ ID NO: 269) |
| 81 to 62 | CAAACCGUGGGUGG AAGGGG (SEQ ID NO: 270) |
| 80 to 61 | AAACCGUGGGUGGA AGGGGG (SEQ ID NO: 271) |
| 79 to 60 | AACCGUGGGUGGAA GGGGGU (SEQ ID NO: 272) |
| 78 to 59 | ACCGUGGGUGGAAG GGGGUA (SEQ ID NO: 273) |
| 77 to 58 | CCGUGGGUGGAAGG GGGUAA (SEQ ID NO: 274) |
| 76 to 57 | CGUGGGUGGAAGGG GGUAAA (SEQ ID NO: 275) |
| 75 to 56 | GUGGGUGGAAGGGG GUAAAG (SEQ ID NO: 276) |
| 74 to 55 | UGGGUGGAAGGGGG UAAAGG (SEQ ID NO: 277) |
| 73 to 54 | GGGUGGAAGGGGGU AAAGGG (SEQ ID NO: 278) |
| 72 to 53 | GGUGGAAGGGGGUA AAGGGA |
| 71 to 52 | GUGGAAGGGGGUAA AGGGAU (SEQ ID NO: 279) |
| 70 to 51 | UGGAAGGGGGUAAA GGGAUC (SEQ ID NO: 280) |

TABLE 2-continued

IGFBP1 promoter tiling RNA array oligonucleotide sequences.

| Name/Position | RNA Sequence (5'-->3') |
|---|---|
| 69 to 50 | GGAAGGGGGUAAAG GGAUCA (SEQ ID NO: 281) |
| 68 to 49 | GAAGGGGGUAAAGG GAUCAG (SEQ ID NO: 282) |
| 67 to 48 | AAGGGGGUAAAGGG AUCAGG (SEQ ID NO: 283) |
| 66 to 47 | AGGGGGUAAAGGGA UCAGGU (SEQ ID NO: 284) |
| 65 to 46 | GGGGGUAAAGGGAU CAGGUU (SEQ ID NO: 285) |
| 64 to 45 | GGGGUAAAGGGAUC AGGUUU (SEQ ID NO: 286) |
| 63 to 44 | GGGUAAAGGGAUCA GGUUUU (SEQ ID NO: 287) |
| 62 to 43 | GGUAAAGGGAUCAG GUUUUC (SEQ ID NO: 288) |
| 61 to 42 | GUAAAGGGAUCAGG UUUUCU (SEQ ID NO: 289) |
| 60 to 41 | UAAAGGGAUCAGGU UUUCUAC (SEQ ID NO: 290) |
| 59 to 40 | AAAGGGAUCAGGUU UUCUAC (SEQ ID NO: 291) |
| 58 to 39 | AAGGGAUCAGGUUU UCUACU (SEQ ID NO: 292) |
| 57 to 38 | AGGGAUCAGGUUUU CUACUA (SEQ ID NO: 293) |
| 56 to 37 | GGGAUCAGGUUUUC UACUAU (SEQ ID NO: 294) |
| 55 to 36 | GGAUCAGGUUUUCU ACUAUG (SEQ ID NO: 295) |
| 54 to 35 | GAUCAGGUUUUCUA CUAUGU (SEQ ID NO: 296) |
| 53 to 34 | AUCAGGUUUUCUAC UAUGUU (SEQ ID NO: 297) |
| 52 to 33 | UCAGGUUUUCUACU AUGUUU (SEQ ID NO: 298) |

TABLE 2-continued

IGFBP1 promoter tiling RNA array oligonucleotide sequences.

| Name/Position | RNA Sequence (5'-->3') |
|---|---|
| 51 to 32 | CAGGUUUUCUACUAUGUUUG (SEQ ID NO: 299) |
| 50 to 31 | AGGUUUUCUACUAUGUUUGU |
| 49 to 30 | GGUUUUCUACUAUGUUUGUC (SEQ ID NO: 300) |
| 48 to 29 | GUUUUCUACUAUGUUUGUCC (SEQ ID NO: 301) |
| 47 to 28 | UUUUCUACUAUGUUUGUCCC (SEQ ID NO: 302) |
| 46 to 27 | UUUCUACUAUGUUUGUCCCG (SEQ ID NO: 303) |
| 45 to 26 | UUCUACUAUGUUUGUCCCGU (SEQ ID NO: 304) |
| 44 to 25 | UCUACUAUGUUUGUCCCGUG (SEQ ID NO: 305) |
| 43 to 24 | CUACUAUGUUUGUCCCGUGG (SEQ ID NO: 306) |
| 42 to 23 | UACUAUGUUUGUCCCGUGGU (SEQ ID NO: 307) |
| 41 to 22 | ACUAUGUUUGUCCCGUGGUG (SEQ ID NO: 308) |
| 40 to 21 | CUAUGUUUGUCCCGUGGUGA (SEQ ID NO: 309) |
| 39 to 20 | UAUGUUUGUCCCGUGGUGAU (SEQ ID NO: 310) |
| 38 to 19 | AUGUUUGUCCCGUGGUGAUG (SEQ ID NO: 311) |
| 37 to 18 | UGUUUGUCCCGUGGUGAUGG (SEQ ID NO: 312) |
| 36 to 17 | GUUUGUCCCGUGGUGAUGGA (SEQ ID NO: 313) |
| 35 to 16 | UUUGUCCCGUGGUGAUGGAC (SEQ ID NO: 314) |
| 34 to 15 | UUGUCCCGUGGUGAUGGACU (SEQ ID NO: 315) |
| 33 to 14 | UGUCCCGUGGUGAUGGACUG (SEQ ID NO: 316) |

TABLE 2-continued

IGFBP1 promoter tiling RNA array oligonucleotide sequences.

| Name/Position | RNA Sequence (5'-->3') |
|---|---|
| 32 to 13 | GUCCCGUGGUGAUGGACUGG (SEQ ID NO: 317) |
| 31 to 12 | UCCCGUGGUGAUGGACUGGG (SEQ ID NO: 318) |
| 30 to 11 | CCCGUGGUGAUGGACUGGGA (SEQ ID NO: 319) |
| 29 to 10 | CCGUGGUGAUGGACUGGGAC (SEQ ID NO: 320) |
| 28 to 9 | CGUGGUGAUGGACUGGGACA (SEQ ID NO: 321) |
| 27 to 8 | GUGGUGAUGGACUGGGACAG (SEQ ID NO: 322) |
| 26 to 7 | UGGUGAUGGACUGGGACAGG (SEQ ID NO: 323) |
| 25 to 6 | GGUGAUGGACUGGGACAGGA (SEQ ID NO: 324) |
| 24 to 5 | GUGAUGGACUGGGACAGGAG (SEQ ID NO: 325) |
| 23 to 4 | UGAUGGACUGGGACAGGAGC (SEQ ID NO: 326) |
| 22 to 3 | GAUGGACUGGGACAGGAGCU (SEQ ID NO: 327) |
| 21 to 2 | AUGGACUGGGACAGGAGCUA (SEQ ID NO: 328) |
| 20 to 1 | UGGACUGGGACAGGAGCUAA (SEQ ID NO: 329) |

(Note: The oligonucleotides were sequentially arranged on the tiling array in a clockwise order beginning at the center. The duplicate was arranged into the tiling array afterward.)

Figure 2A:
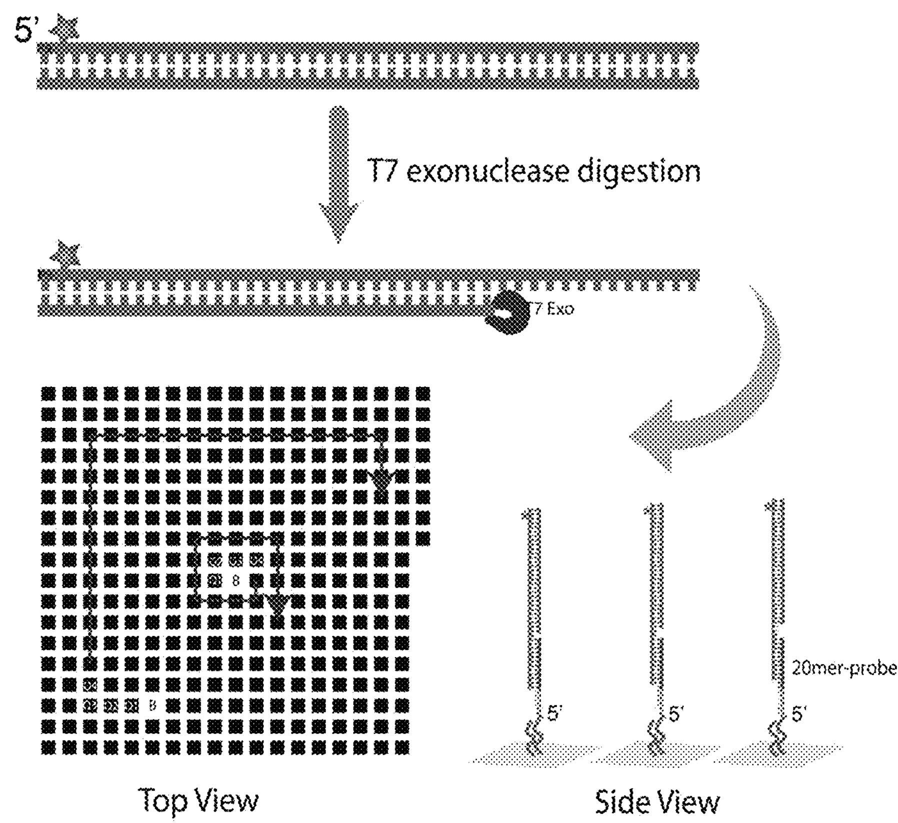
FIG. 2A shows a schematic illustration of how 5'-fluorescent labeled IGFBP1 DNA probe amplicons are generated to test an RNA array. After generation of IGFBP1 amplicons, these double-stranded products were partially digested with T7 exonuclease to yield double-stranded products with single-stranded overhangs capable of hybridizing with RNAs present in the RNA array. As shown, the ability of the fluorescently labeled, exonuclease-digested probe to hybridize with RNAs on the array depends on the amount of sequence overlap between the single-stranded probe overhang and the RNA in question.

The oligonucleotides were sequentially arranged on the tiling array in a clockwise order beginning at the center (FIG. 2). The duplicate was arranged into the tiling array afterward.

In order to generate a probe to test the presence of RNA sequences in the array, two units of T7 exonuclease were used to digest 100 ng of one end FAM-labeled and 5' phosphorothioate-protected IGFBP1 DNA for 1 min at room temperature. T7 exonuclease digestion was stopped by addition of EDTA to a final concentration of 25 mM. The product was applied onto the RNA array for hybridization at 37° C. for 1 hr.

The fluorescence signal that is observed arises from a sequence-specific capture of partial duplex DNA that was fluorescently tagged (6-carboxyfluorescein, FAM) and protected by phosphorothioate DNA bases at its 5' end (FIG.

Figure 2B:
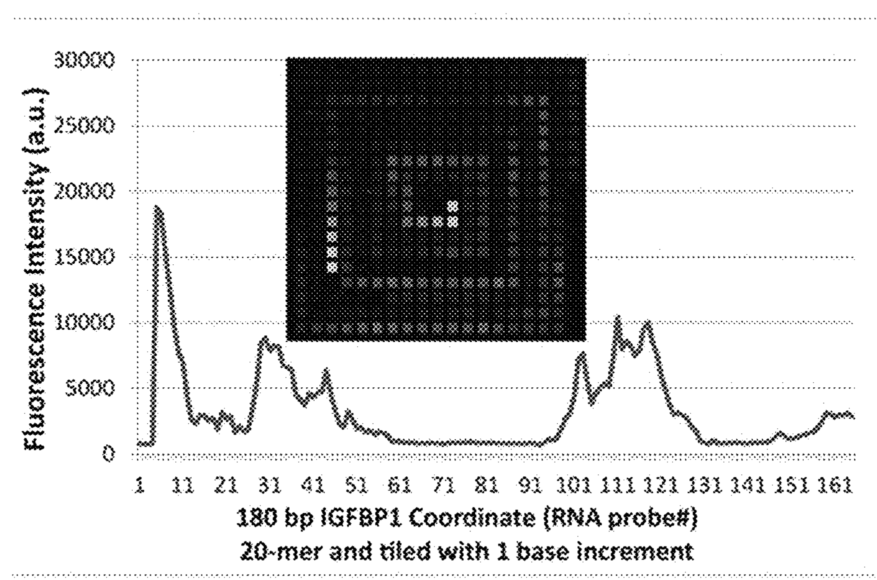
FIG. 2B shows an RNA array fluorescent hybridization signal consistent with the 5' to 3' tiled pattern of the RNAs in the array, where stronger hybridization signal indicates more complementary overlap with the single-stranded overhang in the DNA probe, and less or no signal where less or no overlap occurred.

2A). Fluorescence signal from each array element provides a measurement of the amount of digested duplex capturable by specific complementary oligonucleotides and was expected to vary with the degree of digestion. We profiled the digestion characteristics of T7 exonuclease on FAM labeled 180 bp long IGFBP1 DNA in a control condition (2 units of T7 exonuclease on 100 ng IGFBP1 DNA at room temperature for 1 min) by using the RNA tiling arrays (FIG. 2B). The target DNA was captured in a sequence-specific manner. It is noted that the digestion activity of T7 exonuclease is similar to the activity of Exonuclease 3 (3' DNA exonuclease) that was reported previously Wu et al (2011), *PLoS One* 6, e26217. The result suggests the desired RNA sequences were synthesized accurately on the surface and are accessible for sequence-specific capture of nucleic acids.

In summary, we demonstrated here a strategy for making high density RNA arrays by taking advantage of well-developed DNA array technology. Using this method, millions of RNA oligonucleotides can be copied from high density DNA microarray templates simultaneously with this method. The enzymatically synthesized RNAs on the surface are free from undesired chemical modifications that are inevitable during chemical syntheses resulting from long time exposures to strong acidic and oxidizing reagents. Also, this method is not constrained by the relatively lower coupling yield of RNA phosphoramidites (compared to DNA), and the laborious process for chemical RNA synthesis. Furthermore, modified ribonucleoside triphosphates (e.g., 2'-fluorine-CTP or 2'-fluorine-UTP) can be used to fabricate desired RNA arrays for various applications. High density RNA arrays provide a new avenue for high throughput RNA biomolecular interaction analyses and RNA research.

Figure 3:
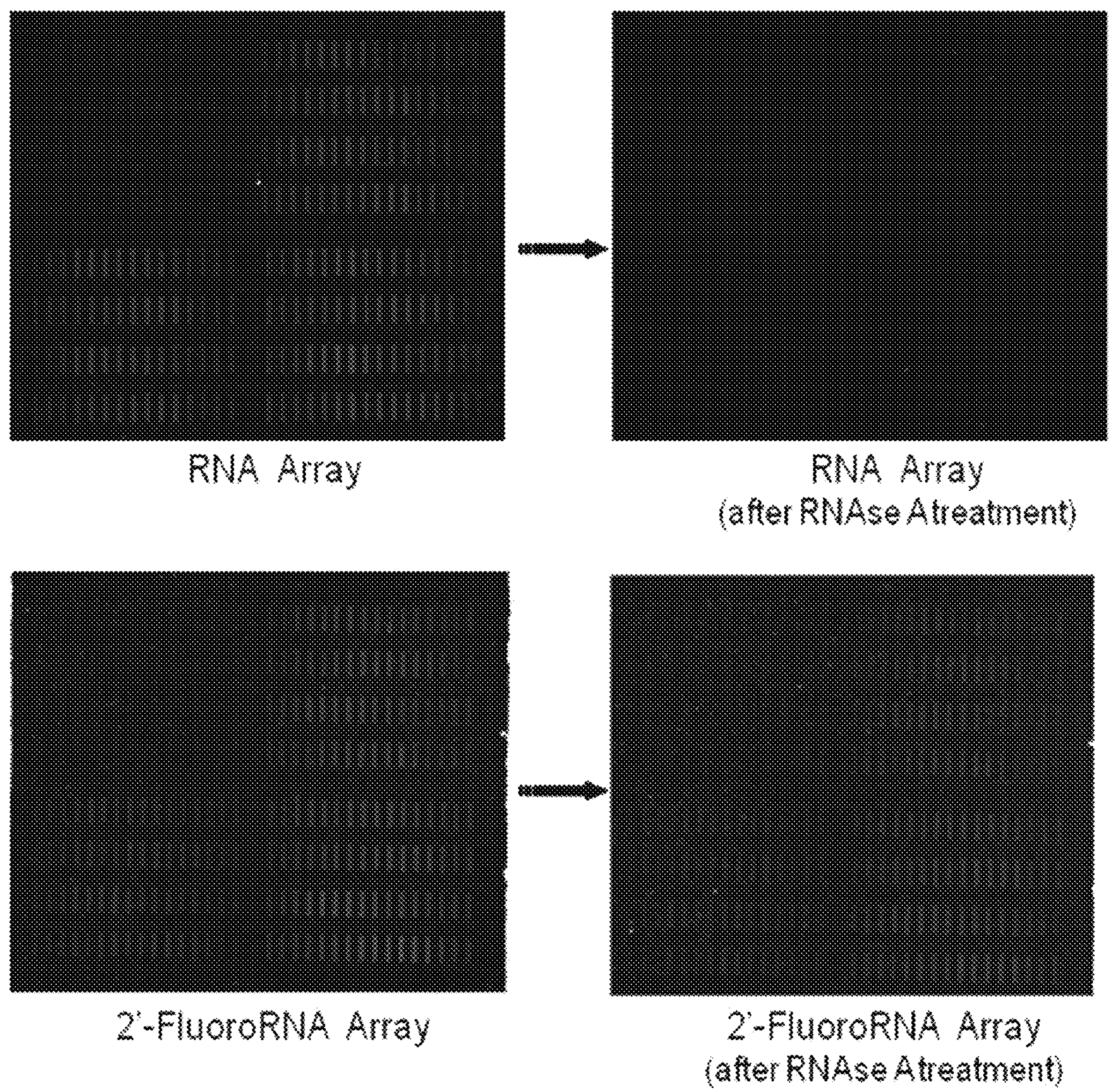
FIG. 3. Top panels are images of fluorescent DNA probes hybridized to an RNA array enzymatically synthesized using unmodified ribonucleosides (top left panel), and the same type of RNA array after RNase A treatment (top right panel), which resulted in complete degradation of the RNA array as indicated by the total loss of hybridization signal. In the bottom panels are images of 2'-fluoro RNA arrays that were enzymatically synthesized using a 2'-fluorine-modified nucleoside triphosphate mix (left bottom panel) and the same type of RNA array and 2'-fluoro RNA array after RNase A treatment (bottom right panel), which shows only a partial loss of hybridization signal indicating that 2'-fluoro RNA arrays are relatively resistant to RNase.

Example 2 RNA Arrays Synthesized with 2'-Fluoro Ribonucleosides are RNase-Resistant In order to determine if RNA arrays could be generated that were RNase resistant, an RNA array and a 2'-fluoro-RNA array were enzymatically synthesized as described previously using natural nucleoside triphosphates (i.e., adenosine triphosphate [ATP], guanosine triphosphate [GTP], cytidine triphosphate [CTP], and uridine triphosphate [UTP] and 2' fluorine modified nucleoside triphosphate mix (i.e. adenosine triphosphate [ATP], guanosine triphosphate [GTP], 2'-fluoro-2'deoxycytidine triphosphate [2'-F-dCTP], 2'-fluoro-2'deoxyuridine triphosphate [2'-F-dUTP]), respectively. Both RNA arrays were then treated with DNase I (20 units) at 37° C. for four hours to eliminate template DNA oligonucleotides, followed by RNase A treatment (>4 units) at 37° C. for 30 minutes. The arrays were then hybridized with their fluorescently labeled cDNAs. As shown in FIG. 3, the RNA arrays generated with unmodified ribonucleotides (upper panels) showed persistent hybridization signal after DNase I treatment, indicating hybridization of the cDNA probe to the RNA array. However, after RNase A treatment, a complete loss of hybridization signal was observed indicating complete degradation of the RNA array. In contrast, the 2'-fluoro-RNA arrays, showed hybridization signal after DNase treatment and RNase A treatment. These data show that the use of RNase-resistant ribonucleosides such as 2'-fluoro ribonucleotides is useful in generating RNase-resistant RNA arrays.

Example 3 Generation of Patterned RNA Arrays Having Functional Properties

We describe here a simple yet powerful new strategy for the enzymatic synthesis of high-density RNA arrays. The key idea is to use RNA polymerase to copy surface-attached DNA molecules on a high-density DNA array into their RNA complements (FIG. 1). The surface is first partially deprotected (e.g. light is used to effect removal of 50% of the NPPOC photolabile protecting groups covering the surface), an array of the DNA complements to the eventual desired RNA sequences is synthesized by standard light-directed synthesis on the exposed sites, and the remaining surface sites are then deprotected, followed by synthesis of RNA primer sequences. These primer sequences on the second group of sites are hybridized to their complements on the first group, whereupon they may be extended with T7 RNA polymerase to yield RNA:DNA duplexes. The DNAs are removed with DNase I, leaving behind the desired single stranded RNAs. The strategy is compatible with either natural unmodified ribonucleoside triphosphates (rNTPs), or alternatively, 2' fluoro-modified (2'F) rNTPs may be included in the polymerase extension reaction to impart nuclease resistance and other desirable characteristics to the synthesized RNAs. We note that the use of a very long, flexible, hydrophilic spacer (we employed a PEG 2000 moiety) between the substrate and the oligonucleotides is critical—this is not surprising, as it is necessary for the DNA complement and RNA primer sequences to anneal while both are still attached to the surface. A second key to this strategy is the ability to fabricate two different nucleic acid sequences within individual DNA features—in this case, both a primer sequence, and a template sequence.

Methods

Array Substrate Preparation

Standard glass slides coated with 50 Å chromium and 1,000 Å of gold (EMF corp., NY, USA) were extensively rinsed with hexane and ethanol and dried under a nitrogen stream. A 7.5 nm layer of amorphous carbon was then DC magnetron sputtered on the gold surface (Denton Vacuum, N.J., USA). The carbon-on-gold surface was hydrogen-terminated in a 13.56 MHz inductively coupled hydrogen plasma for 12 minutes (30 Torr $H_2$, room temperature). Next, 40 μl of 9-Decene-1-ol (Sigma Aldrich, Mo., USA) was placed directly onto the newly hydrogen-terminated surface and covered with a quartz coverslip. The surfaces were irradiated under nitrogen purge with a low-pressure mercury vapor quartz grid lamp ($\lambda$=254 nm, 0.35 mW/cm$^2$) for 16 h. After the photoreaction, the surfaces were rinsed extensively with ethanol and deionized water and dried under a nitrogen stream.

In Situ Oligonucleotide Array Synthesis

Light-directed photolithographic synthesis of DNA template arrays was performed on a 9-Decen-1-ol modified carbon-on-gold surface with a digital micromirror-based Maskless Array Synthesis (MAS) system connected to an ABI Expedite™ 8909 Nucleic Acid Synthesis System (Applied Biosystems, Calif., USA) as described previously. All the 5'-NPPOC-protected phosphoramidite nucleosides underwent a single 80 sec coupling step. All the 3'-dimethoxytrityl (DMT)-protected phosphoramidite nucleosides underwent a single 360 sec coupling step. The 5'-DMT-protected polyethyleneglycol 2000 phosphoramidite underwent two 900 sec coupling steps in a row. While the NPPOC protecting groups were removed by exposure to UV light, all the DMT protecting groups were removed by flowing through a deblocking mix (3% dichloroacetic acid in toluene). The light dose to remove full or a half of the photolabile NPPOC (nitrophenylpropyloxycarbonyl) protecting groups was determined prior to DNA template array fabrication. A series of incremental doses of 365 nm light (Joule/cm$^2$) was used for a 30 nt quality control (QC)

oligonucleotide synthesis. The optimal dose was chosen to yield the highest level of fluorescence (for a full deprotection) or a half of it (for a half deprotection) from hybridization of a fluorescently tagged QC complement. A total dose of 3 Joule/cm$^2$ 365 nm light was used to remove all NPPOCs during each cycle. A total dose of 0.32 Joule/cm$^2$ 365 nm light was used to remove a half of NPPOCs for RNA primer synthesis. After half-deprotection of the first layer of NPPOC-protected phosphoramidite nucleosides, the exposed hydroxyl moieties were reacted with the DMT-protected phosphoramidite nucleosides at the first base of the RNA primer. Afterward, the other half of the NPPOC protecting groups were removed by a full dose of UV light prior to the light-directed oligonucleotide synthesis on the surface. After the light-directed oligonucleotide synthesis of DNA template was completed, the 5' end of the oligodeoxyribonucleotides were capped three times with a 1:1 v/v mixture of capping reagents A and B (A:B solution; see below) for 90 sec (~320 μl). The DMT protecting groups on the first base of RNA primer were removed using a deblocking mix, and the RNA primer sequence was synthesized using a standard nucleic acid synthesis protocol. DCI Activator (0.25 M dicyanoimidazole in acetonitrile) and all NPPOC (3'-nitrophenylpropyloxycarbonyl) protected phosphoramidite nucleosides [5'-NPPOC-dAdenosine (tac) 3'-β-cyanoethylphosphoramidite (NPPOC-dA), 5'-NPPOC-dThymidine 3'-β-cyanoethylphosphoramidite (NPPOC-dT), 5'-NPPOC-dCytidine (ib) 3'-β-cyanoethylphosphoramidite (NPPOC-dC), 5'-NPPOC-dGuanosine (ipac) 3'-β-cyanoethylphosphoramidite (NPPOC-dG)], N-methylimidazole, acetonitrile, and tetrahydrofuran (THF) were purchased from Sigma Aldrich (MO, USA). Capping reagent A (THF/PAc2O) and deblocking mix were purchased from Glen Research (VA, USA). Oxidation solution (0.02 M iodine/pyridine/$H_2O$/THF), acetonitrile anhydrous, 5'-DMT-polyethyleneglycol 2000 phosphoramidite, all 3'-DMT-5'-cyanoethylphosphoramite 2'-O-methyl or 2'-fluoro nucleosides were purchased from ChemGenes (MA, USA). Capping reagent B (6.5% 2-dimethylaminopyridine, 2% N-methylimidazole and 10% 2,6-lutidine in THF) and exposure solvent (1% imidazole in DMSO) were mixed in-house. Anhydrous reagents were kept over molecular sieves (AldraSORB™ water trapping packets, Sigma Aldrich).

Enzymatic Fabrication of RNA Arrays

A gasket, Gene Frame—1×1 cm internal (Abgene, Epsom, UK), was attached so that it surrounds the DNA features. A 50 μl annealing buffer consisting of 4×SSPE buffer (Sigma Aldrich), 1× RNasecure™ reagent (Ambion, Tex., USA), 9% polyethylene glycol 6000, was applied onto the array and incubated at 60° C. for 20 min, then slowly cooled down to 37° C. for 4 hr. The prolonged incubation time allows the RNA primers to anneal adequately to their DNA complements. The polyethylene glycol accelerated RNA:DNA hybridization while RNasecure™ was included to irreversibly inactivate possible RNases on the surface. The surface was rinsed with 1× transcription buffer (40 mM Tris-HCl, pH 7.9, 6 mM $MgCl_2$, 10 mM DTT, 20 mM NaCl, 2 mM spermidine) prior to RNA extension reaction. For 2'-fluoro RNA extension, a mutant T7 RNA polymerase was used while wild-type T7 RNA polymerase was used for natural RNA extension. A 50 μl RNA extension reaction mixture was added to the surface and incubated at 37° C. for 6-8 h in a humid chamber. A natural RNA extension reaction mixture consists of 40 mM Tris-HCl, pH 7.9, 6 mM $MgCl_2$, 10 mM DTT, 20 mM NaCl, 2 mM spermidine, 0.5 mM each NTP, 2 U/μl T7 RNA polymerase (Thermo Scientific, USA), and 1 U/μl RNase inhibitor (New England Biolabs, USA). A 2'-fluoro RNA extension reaction mixture consists of 40 mM Tris-HCl, pH 7.9, 2 mM $MgCl_2$, 2 mM $MnCl_2$, 10 mM DTT, 20 mM NaCl, 0.05% Triton X-100, 012 mg/μl BSA, 2 mM spermidine, 0.5 mM adenosine triphosphate, 0.5 mM guanosine triphosphate, 0.5 mM 2'-fluoro-uridine triphosphate (TriLink, Calif., USA), 0.5 mM 2'-fluoro-cytidine triphosphate (TriLink), 0.015 U/μl pyrophosphatase, 2 U/μl T7 R&DNA polymerase (Epicentre, Wis., USA) and 1 U/μl RNase inhibitor (New England Biolabs, USA). After extension reaction, $CaCl_2$ was added to a final concentration of 0.5 mM, and Turbo DNase (Ambion, Tex., USA) was added to a final concentration of 0.1 U/μl. The reaction mixture was incubated at 37° C. for another 6~8 h to completely remove the DNA templates in a humid chamber. The resulting array was immersed in TE buffer, pH 7.0 at 75° C. for 10 min to inactivate DNase I and T7 RNA polymerase. The array was rinsed extensively with TE buffer and deionized water and dried under a nitrogen stream.

Capture and Detection of Fluorescently Labeled DNA on High Density RNA Arrays

The fluorescein labeled DNA fragment corresponding to positions −205 to −25 of the mouse IGFBP1 promoter was amplified by PCR from NIH 3T3 (mouse embryonic fibroblast cell line) genomic DNA (NEB, Mass., USA) using the primers (5'-T*T*A GC/iFluorT/CCT GTC CCA GTC CAT-3' (SEQ ID NO:4) and 5'-TAT GAA GGG CTG GCT GTG C-3' (SEQ ID NO:5). [*] represents a phosphorothioate DNA base and [/iFluorT/] represents a fluorescein-labeled thymidine. All primers were custom synthesized by IDT (Integrated DNA Technologies, Iowa, USA). AmpliTaq DNA polymerase (Applied Biosystems, Calif., USA) was used in the PCR reaction. The PCR cycling consisted of 3 min at 94° C.; then 40 cycles of 30 sec at 95° C., 30 sec at 59° C., and 30 sec at 72° C.; and final elongation 6 min at 72° C. The amplicon was purified using the Promega Wizard SV Gel and PCR Clean-up System (Promega, Wis., USA). A total of 720 ng of purified PCR amplicion was partially digested with 15 units of T7 exonuclease (T7 Gene 6 Exonuclease; Affymetrix, Calif., USA) at 25° C. for 1 min and right away quenched with EDTA at a final concentration of 25 mM. Following inactivation of the T7 exonuclease at 75° C. for 10 min, the reaction buffer was exchanged to 1×SSPE buffer at a concentration of 0.2 μM before application to the RNA arrays. The hybridization reaction was performed in a humid chamber at 25° C. for 30 min, followed by a thorough rinse and incubation with 1×SSPE buffer at 37° C. for 15 min to remove nonspecifically bound DNA. Fluorescence images were obtained with a 488 nm laser and 512 nm filter using a GeneTac UC 4×4 microarray scanner (Genomic Solutions, Mich., USA). Table 1 contains the probe sequences synthesized on the surface. Each of the tiling arrays was composed of 332 features with each feature measuring 280 μm×280 μm, and separated by 140 μm gaps.

Nuclease Susceptibility Test

DNase I (Turbo DNase; Ambion) and RNase A (Ribonuclease A; Sigma Aldrich) were used to interrogate the nature of DNA, RNA and 2'-fluoro RNA "Badger Chemist" arrays. All arrays were first hybridized with a mixture of three fluorescently labeled DNA probes and visualized using a GeneTac UC 4×4 microarray scanner. The hybridization reaction mixture consisted of 0.2 μM of each probe in 4×SSPE buffer and was incubated in a humid chamber at 37° C. for 30 min, followed by a thorough rinse and incubation with 1×SSPE buffer at 37° C. for 15 min to remove nonspecifically bound DNA. Table 3 contains the sequences of a "Badger Chemist" array, as well as the fluorescently labeled detection probes. The RNA and 2'-fluoro RNA arrays were first treated with a total of 2.5 units of DNase I at 37° C. for 7 hr and then a total of 1 μg of RNase A. Conversely, the DNA arrays were first treated with RNase A and then with DNase I. The arrays were heat treated at 75° C. for 10 min before again being subjected to fluorescence imaging.

TABLE 3

Figure 4:
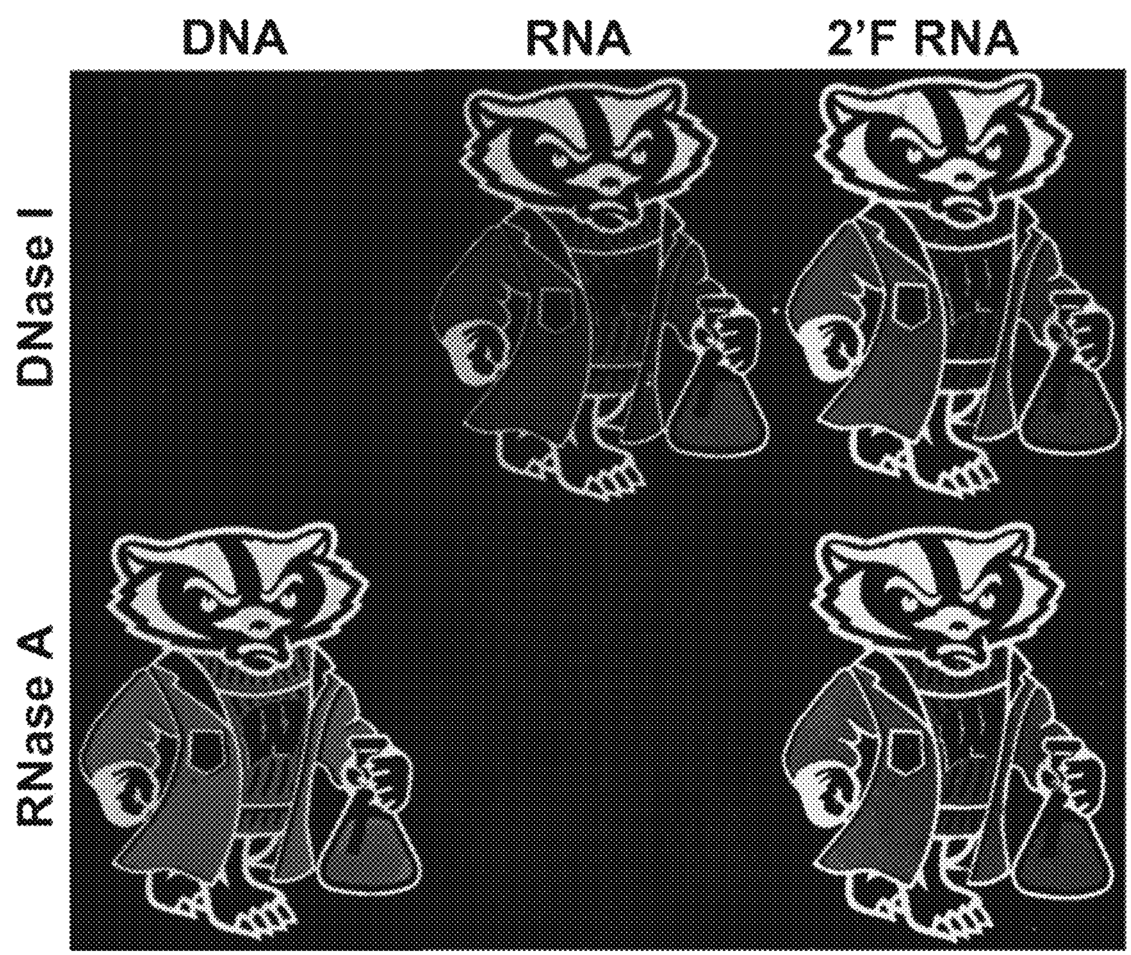
FIG. 4 shows a fluorescence image of a patterned array of DNAs, RNAs, and modified RNAs after various treatment conditions and hybridization to complementary probe sequences labeled with distinct fluorophores. The dimensions of the "Badger Chemist" array are about 6 mm×5 mm, which consists of the "body", the "sweater/flask" and the "lab coat" sequences (Table 3). The natural RNA and 2'-fluoro RNA array were treated with DNase I and RNase A, sequentially, while the DNA array was treated with RNase A and then DNase I. The arrays were visualized by hybridization with their DNA complements labeled with FAM (sweater/flask), Texas Red (body), and Cy5 (lab coat).

Badger Chemist DNA and RNA Array Sequences (see FIG. 4)

| Badger Chemist DNA template array sequences | | Expected Badger Chemist RNA array Sequences | |
|---|---|---|---|
| Name | Sequence (3' to 5') | Name | Sequence (5' to 3') |
| body | TGAGAACGTCCAGTAGCCG (SEQ ID NO: 10) | body | ACUCUUGCAGGUCAUCGGC (SEQ ID NO: 171) |
| lab coat | GATTGTCCACTCAAGACT (SEQ ID NO: 330) | lab coat | CUAACAGGUGAGUUCUGA (SEQ ID NO: 331) |
| sweater/flask | GGTGACAACGTTTCAATA (SEQ ID NO: 11) | sweater/flask | CCACUGUUGCAAAGUUAU (SEQ ID NO: 172) |

The sequence initiated from the surface for the Badger Chemist template DNA array is 3'-T/PEG2K/A GCC TGT GCC GCT T-5' (SEQ ID NO:332); and the sequence initiated from the surface for the Badger Chemist RNA tiling array is 5'-T/PEG2K/A fCmG mG mAfCmAfC mGmGfC mGmAmA-3,' which served as an RNA primer for extension reaction. Italic letters represent RNA bases. /PEG2K/represents a polyethylene glycol linker of an approximate molecular weight of 2,000 Da. mG and mA are 2'-methoxy RNA bases. fC is a 2'-fluoro RNA base.

24-2-Min Aptamer Binding Assay

An RNA array consisting of the 24-2-min sequence (5'-mGmAfC mGfCmG mAfCfC mGmAmA AUG GUG AAG GAC GGG UCC AGU GCU UCG GCA CUG UUG AGU AGA GUG UGA GCU CCG UAA CUG GUC GCG UC-3' (SEQ ID NO:333) in the pattern of the University Wisconsin logo was used for a functional assay. [m] represents a "2'-methoxy" RNA base, while [f] represents "2'-fluoro" RNA base. The underscored sequence is the RNA primer sequence synthesized using DMT-protected phosphoramidite nucleosides. The array was heat denatured at 75° C. for 5 min and quickly chilled on ice in a binding buffer containing 40 mM HEPES pH 7.4, 125 mM KCl, 5 mM $MgCl_2$, and 5% DMSO. The array was then incubated with DFHBI at a final concentration of 20 μM for 30 min at room temperature. The image was visualized under a 488 nm laser with a 512 nm filter using a GeneTac UC 4×4 microarray scanner.

Cleavage Tests with 10-23 DNAZyme

Table 3 contains the sequences of a "Badger Chemist" array. The 10-23 DNAZyme (5'-TCA GAA CTC AGG CTA GCT ACA ACG ACT GTT AGT TC-3') (SEQ ID NO:334) is designed to cleave the "lab coat" RNA sequence in the "Badger Chemist" array). The underscored sequences are the substrate-binding domains. The arrays were first annealed with the 10-23 DNAzyme at a final concentration of 1 μM in a 50 μl annealing buffer (5 mM Tris, pH 7.5, 15 mM NaCl, 0.1 mM EDTA). After application of the mixture to the array, the surface was incubated on a heating block at 95° C. for 3 min following by chilling on ice. The cleavage reaction was initiated by addition of 10× cleavage buffer followed by $10\times Mn^{2+}$ to give a final incubation condition of 50 mM Tris, pH 7.5, 10 mM $MnCl_2$, and 150 mM NaCl. The sample was placed in a humid chamber at 37° C. for 5 hr for DNAZyme cleavage and immersed in 8 M urea solution to stop the reaction. Both before and after DNAZyme treatment, the arrays were hybridized with a mixture of three fluorescently labeled DNA probes and visualized using a GeneTac UC 4×4 microarray scanner.

Several approaches were employed to evaluate the fidelity and utility of the arrays: these include nuclease sensitivity, DNA hybridization, DNAzyme cleavage, and RNA aptamer binding experiments. FIG. 4 shows the results of nuclease digestion experiments on DNA, RNA, and 2'F RNA arrays. Each array contains three 30-32mer sequences corresponding to the body, sweater/flask, or lab coat of a "Badger Chemist" (Table 3). The arrays were visualized after nuclease treatment by hybridizing them with a mixture of the three corresponding oligodeoxynucleotide complements, tagged respectively with the fluorophores fluorescein (sweater and bag), Texas Red (head; hands; and feet), and Cy 5 (labcoat), followed by washing and fluorescence imaging. It is evident from the figure that while the DNA arrays are completely destroyed by DNase treatment but impervious to RNase treatment, the RNA arrays show the opposite result, in that they are completely destroyed by RNase treatment but impervious to DNase treatment. As expected, the 2'F RNA arrays are resistant to both DNase and RNase treatment. These results confirm in each case the nature of the nucleic acid comprising the array elements. In addition, the experiments also show that for each array, the nucleic acid molecules on the surface hybridize specifically to fluorescently tagged solution complements, as illustrated by the correct localization of the green, yellow, and red features in the image.

The hybridization and exonuclease sensitivity results presented in Example 1 above and in this example provide strong evidence that the normal and modified RNA arrays have the correct nucleic acid compositions, and exhibit normal base-pairing functionality. We sought to further confirm the functionality of the sequences with two additional experiments: the ability of the RNA sequences to serve as substrates for a RNA-specific DNAzyme, and their ability to fold correctly into RNA aptamers and exhibit specific binding to a target molecule.

Figure 5A:
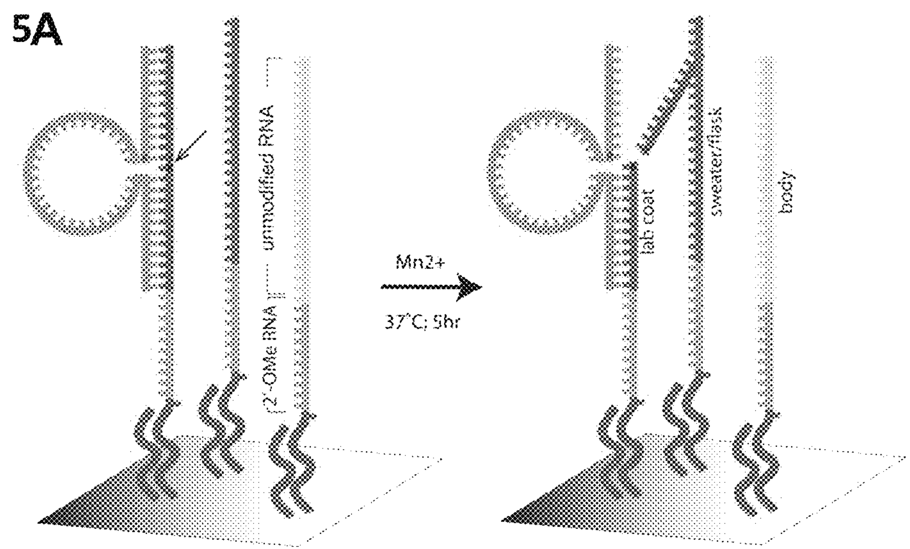
FIGS. 5A and 5B shows a fluorescence image of a patterned array of DNAs, RNAs, and modified RNAs before and after DNase treatment, and followed by hybridization to complementary probe sequences labeled with distinct fluorophores. 5A) The schematic diagram of 10-23 DNAZyme cleavage test on RNA array. 5B) The dimensions of "Badger Chemist" array are about 6 mm×5 mm, which consists of the "body," the "sweater/flask" and the "lab coat" sequences (Table 3). The arrays were visualized by hybridization with the three corresponding oligodeoxynucleotide complements, tagged respectively with the fluorophores fluorescein (sweater/flask), Texas Red (body), and Cy 5 (lab coat). The "lab coat" sequences were intact on the DNA array, whereas 70% were cleaved on the natural RNA array and 55% were cleaved on the 2'-fluoro RNA array. It is noted there were fewer cleavage events on the 2'-fluoro RNA array than on the natural RNA array. Although the purine nucleobases, which participated in cleavage events, were not 2'-fluoro modified, we speculate the halogenated groups in the ribose rings of pyrimidine nucleobases would interfere with RNA:DNA duplex formation and result in different efficiency. This is the first report showing the different cleavage activities of 10-23 DNAzyme on natural RNA and 2'-fluoro RNA molecules.
Figure 5B:
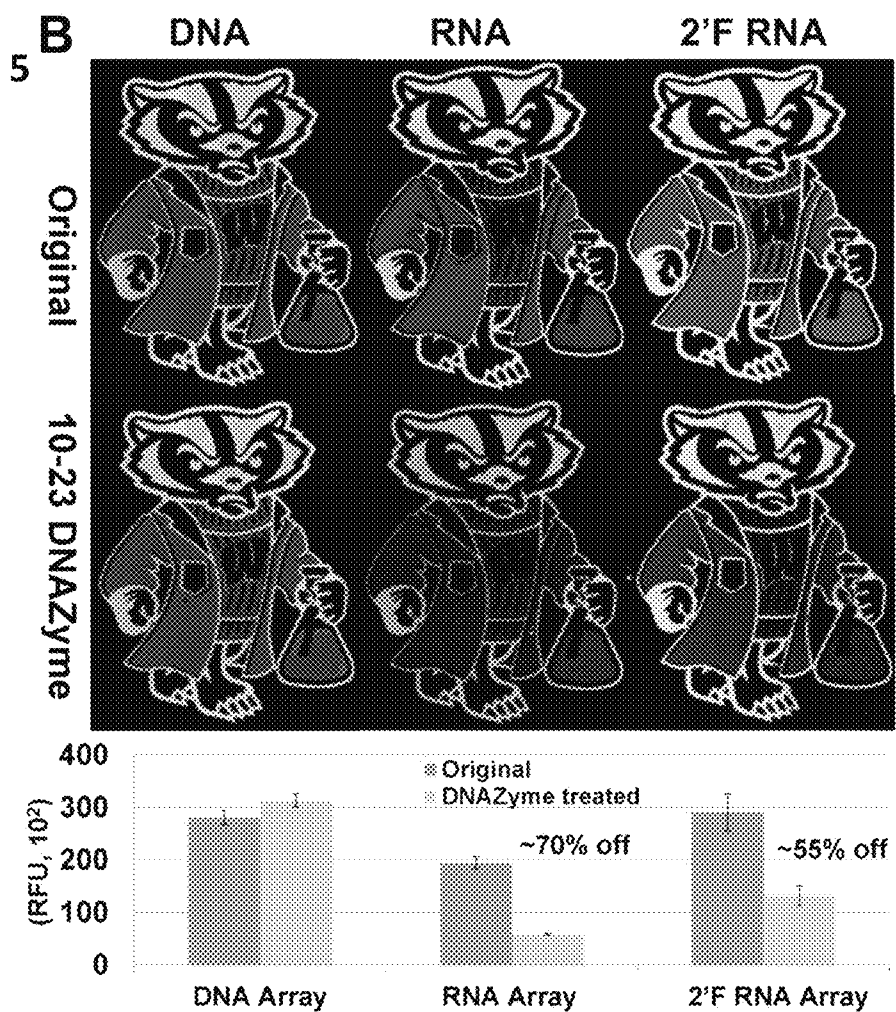

The 10-23 DNAzyme (having RNase activity), first described by Joyce and colleagues in 1997 (Santoro et al, 1997, *Proc Natl Acad Sci USA.* 94(9):4262-4266), consists of a catalytic core of 15 deoxynucleotides flanked by substrate-binding domains. Any RNA substrate that is accessible to Watson-Crick pairing with the 10-23 DNAzyme substrate-binding domains can be cleaved at the phosphodiester linkage between purine and pyrimidine nucleobases that separate the complementary regions on the substrate (FIG. 5A). We designed a 10-23 DNAzyme to cleave the RNA sequences on the "Badger Chemist" array that correspond to the lab coat. The arrays were incubated with the 10-23 DNAzyme in a $Mn^{+2}$ containing buffer for 5 hr at 37° C. As shown in FIG. 5B, the "lab coat" sequences remained intact on the DNA array, whereas 70% were cleaved on the RNA array and 55% were cleaved on the 2'-fluoro RNA array. These results show that the surface-bound natural and modified RNA molecules are recognized as RNA by the DNAzyme.

One important application of RNA arrays is likely to be their use for the discovery, characterization, and evolution of aptamer sequences. The term "aptamer" refers to nucleic acid molecules that fold into conformations that impart them with specific binding affinity for a molecular target. Although nucleic acid aptamers can be composed of either DNA or RNA, RNA aptamers have the intriguing advantage of being possible to generate in vivo, and in fact naturally occurring RNA aptamers known as "riboswitches" have been described and shown to play critical roles in gene regulation. We wished to determine if the surface-bound RNAs in RNA arrays were able to fold properly to yield functional aptamer sequences. We chose to evaluate the "24-2" aptamer recently developed by Jaffrey and co-workers (Paige et al 2011, *Science:* 333:642-646). This aptamer imparts fluorescent properties similar to those of green fluorescent protein (GFP) to RNA molecules. It does this by binding the chromophore DFHBI (3,5-difluoro-4-hydroxybenzylidene imidazolinone); although in solution this chromophore is non-fluorescent, when immobilized by binding to the 24-2 aptamer its dihedral freedom is restricted and it becomes fluorescent. As described by Jaffrey and colleagues, if the aptamer sequence is fused with a naturally occurring RNA of interest, addition of DFHBI renders it visible by fluorescence imaging, making it possible to visualize the tagged RNA molecules in living cells. "24-2 min" is a shorter version of the original 24-2 aptamer.

Figure 6:
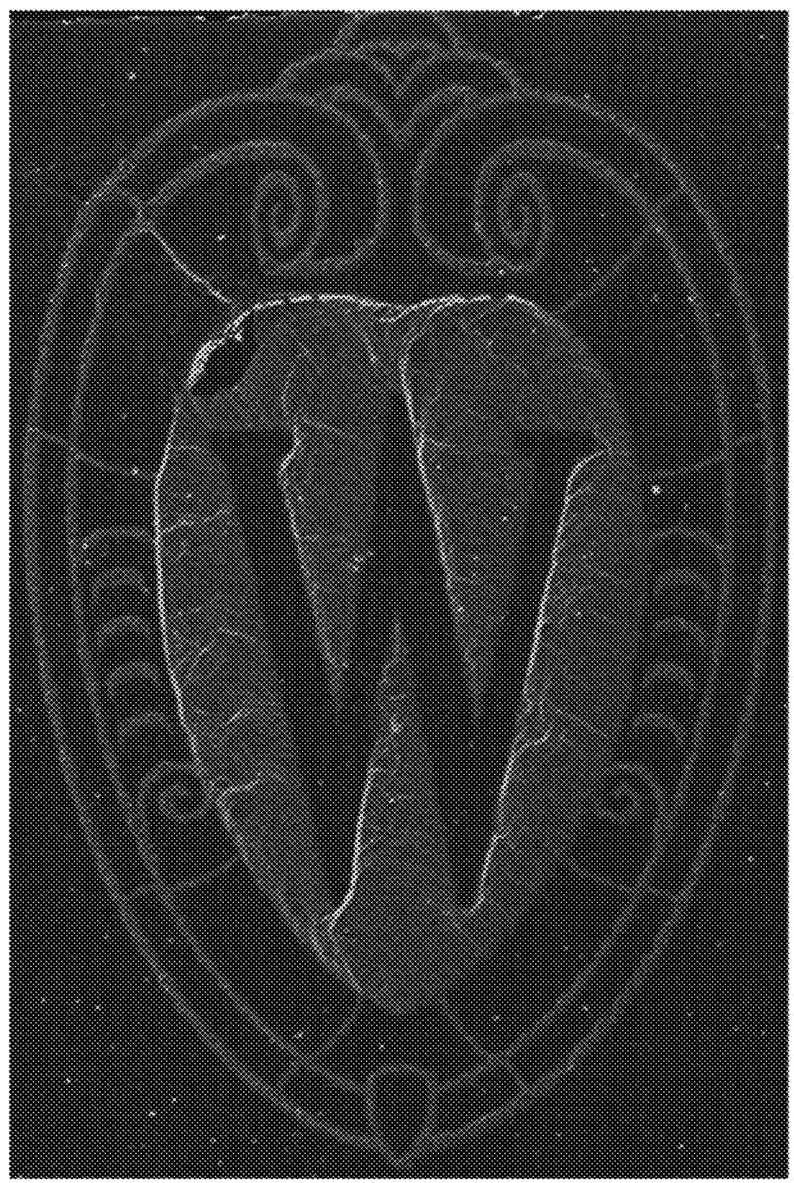
FIG. 6 shows a fluorescence image of a 24-2-min RNA aptamer array. The array was incubated with the chromophore 3,5-difluoro-4-hydroxybenzylidene imidazolinone (DFHBI) (24-2), which fluoresces upon binding to the RNA aptamer sequence. After incubation with DFHBI, the array was visualized using a GeneTac UC 4×4 microarray scanner with a 488 nm blue excitation laser and a 512 nm emission filter.

We fabricated an RNA array consisting of the 24-2-min aptamer sequence in the pattern of the University of Wisconsin logo. The array was incubated with DFHBI followed by fluorescence imaging. The fluorescence image in FIG. 6 shows a pattern of green fluorescence corresponding to the logo, demonstrating that the aptamer sequences are properly folded and functional. This result suggests the possibility of synthesizing hundreds of thousands of variant 24-2 sequences on the array, and screening them all in parallel to identify aptamers with improved fluorescence characteristics such as increased brightness or red-shifted fluorescence emission.

In summary, we have described a novel strategy for the fabrication of high-density RNA arrays. The fidelity and functionality of the RNA elements is demonstrated in hybridization, DNAzyme cleavage, nuclease digestion, and RNA aptamer binding experiments.

What is claimed is:

1. A method for generating a template array, comprising (i) providing a solid support comprising a layer of protected deoxyribonucleosides that comprise a 5'-photolabile protecting group and are covalently linked at their 3' end to a spacer layer bound to the solid support;

(ii) irradiating the layer of protected deoxyribonucleosides with ultraviolet energy sufficient to deprotect about half of the protected deoxyribonucleosides;

(iii) coupling the deprotected deoxyribonucleosides with a ribonucleoside phosphoramidite comprising a 5'acid-labile protecting group;

(iv) irradiating the remaining protected deoxyribonucleosides with ultraviolet irradiation sufficient to deprotect all of the remaining protected deoxyribonucleosides;

(v) extending the deprotected deoxyribonucleosides, at one or more locations, by light-directed 3' to 5' photolithographic synthesis to generate template DNA oligonucleotides of the deprotected deoxyribonucleosides;

(vi) coupling a protecting group to the 5' ends of the template DNA oligonucleotides;

(vii) removing the 5' acid-labile protecting group on the protected ribonucleosides by acid treatment; and (viii) extending the deprotected ribonucleosides at one or more locations, by 5' to 3' chemical synthesis of RNA primers comprising a sequence that is complementary to a sequence at the 3' end of the template DNA strands to obtain a template array.

2. The method of claim 1, wherein in step (iii) the 5' acid-labile protecting group comprises a 4,4'-dimethoxytrityl (DMT) group.

3. The method of claim 1, wherein in step (vi) the protecting group coupled to the 5'-ends of the template DNA strands is an acetyl group or phenoxyacetyl group.

4. The method of claim 1, wherein in step (viii) RNase-resistant modified ribonucleoside phosphoramidites are used in the extension of the deprotected phosphoramidites to obtain RNase-resistant RNA primers.

5. The method of claim 4, wherein the RNase-resistant modified ribonucleoside phosphoramidites are 2'-fluoro ribonucleoside phosphoramidites or 2'-methoxy ribonucleoside phosphoramidites.

* * * * *